United States Patent [19]

Ohno et al.

[11] Patent Number: 5,202,447
[45] Date of Patent: Apr. 13, 1993

[54] PROCESS OF PRODUCING 5,6,7-TRINOR-4,8-INTER-M-PHENYLENE PGI2 DERIVATIVES

[75] Inventors: Kiyotaka Ohno, Fujisawa; Hiroshi Nagase, Kamakura; Yutaka Hosono, Yokohama; Hisanori Wakita; Koji Kawai, both of Kamakura; Hideo Yoshiwara, Nagoya, all of Japan

[73] Assignee: Toray Industries, Inc., Japan

[21] Appl. No.: 601,783

[22] PCT Filed: Feb. 27, 1990

[86] PCT No.: PCT/JP90/00237

§ 371 Date: Jan. 2, 1991

§ 102(e) Date: Jan. 2, 1991

[87] PCT Pub. No.: WO90/10003

PCT Pub. Date: Sep. 7, 1990

[30] Foreign Application Priority Data

Feb. 27, 1989 [JP] Japan .................... 1-46873
Feb. 27, 1989 [JP] Japan .................... 1-46874

[51] Int. Cl.⁵ ......................... A61K 307/93
[52] U.S. Cl. .................................. 549/458
[58] Field of Search ......................... 549/458

[56] References Cited

FOREIGN PATENT DOCUMENTS 0060640 9/1982 European Pat. Off.
0084856 8/1983 European Pat. Off.
0274064 7/1988 European Pat. Off.

OTHER PUBLICATIONS

Ohno et al. II. Adv. in Prostaglandin, Thromboxane and Leukotriene Res., vol. 15, Raven Press, N.Y., pp. 279-281 (1985).

*Primary Examiner*—Bernard Dentz
*Attorney, Agent, or Firm*—Austin R. Miller

[57] ABSTRACT

The present invention provides a process for preparing 5,6,7-trinor-4,8-inter-m-phenylene PGI₂ derivative [VII] using 3a,8b-cis-dihydro-3H-5,7-dibromocyclopenta[b]benzofuran (1) as a starting material, as well as compounds of the formulae (8) and (11) which are intermediates for the preparation of the compound of the formula (1).

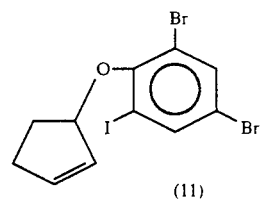

(11)

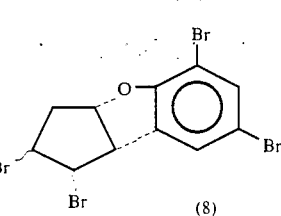

(8)

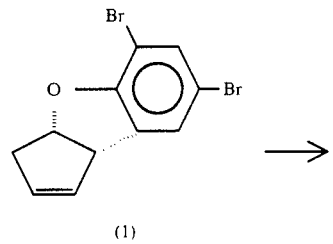

(1)

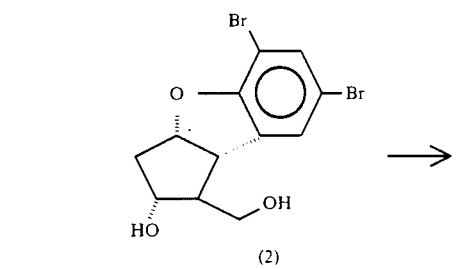

(2)

(Abstract continued on next page.)

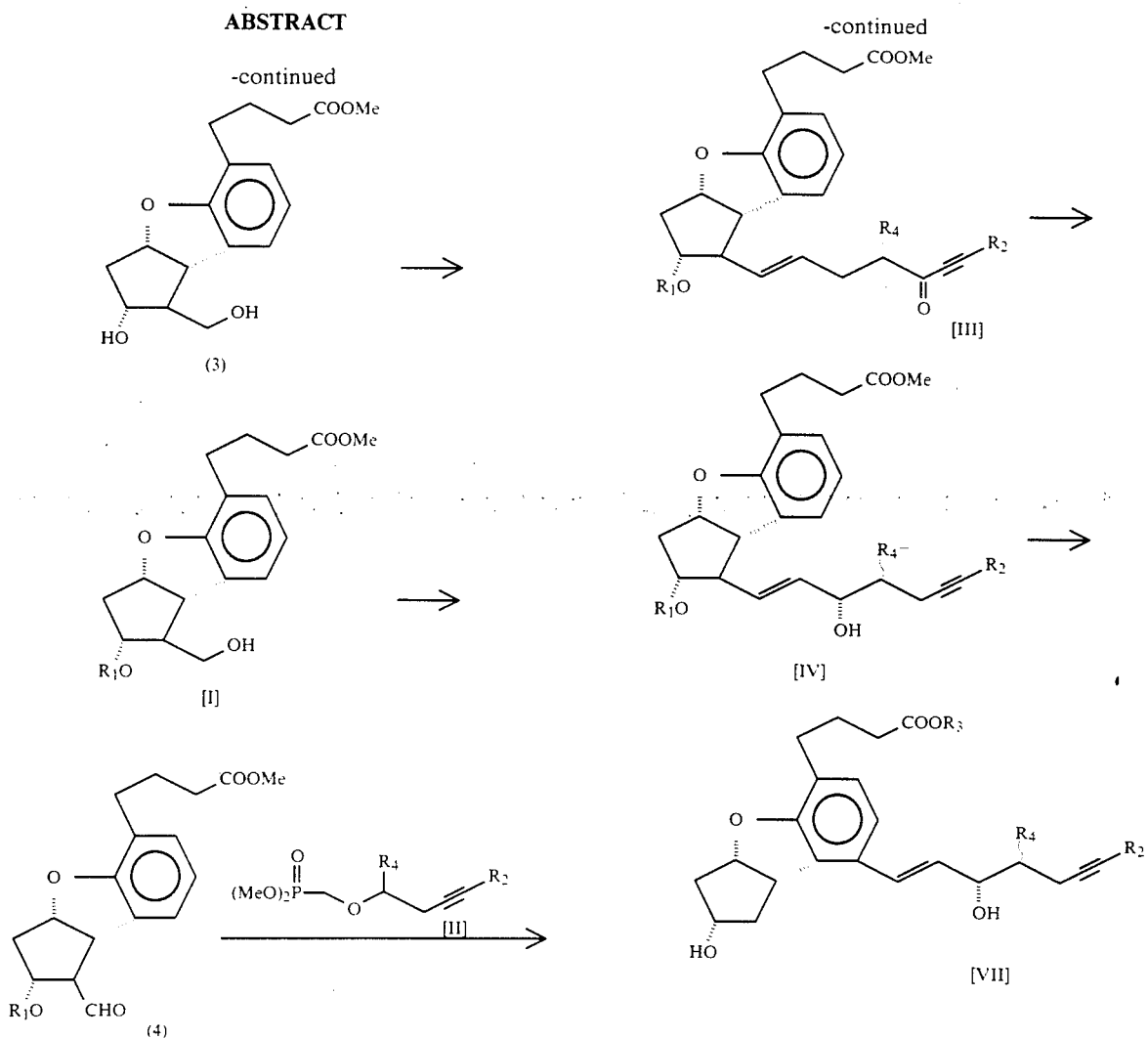
6 Claims, No Drawings

PROCESS OF PRODUCING 5,6,7-TRINOR-4,8-INTER-M-PHENYLENE PGI2 DERIVATIVES

TECHNICAL FIELD

This invention relates to a manufacturing process of PGI₂ derivatives having m-phenylene structure, i.e., a compound represented by the formula [VII]:

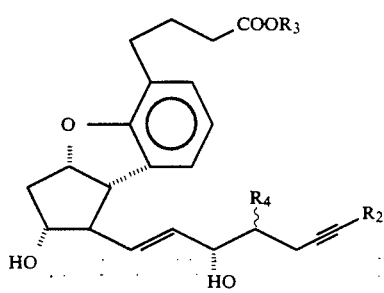

[VII]

(wherein $R_2$ represents methyl or ethyl; $R_3$ and $R_4$ represent hydrogen atom or methyl) which is useful as an anti-thrombus agent.

BACKGROUND ART

As a process for manufacturing m-phenylene type PGI₂ derivatives which have an α-side chain containing 4 carbon atoms, processes shown in Charts 1 and 2 (disclosed in Japanese Laid Open Patent Application (Kokai) Nos. 36477/81 and 124778/83, respectively) and shown in the literature ("Advances in Prostaglandin, Thromboxane and Leukotriene Research", vol.15, p.279) are known.

CHART 1

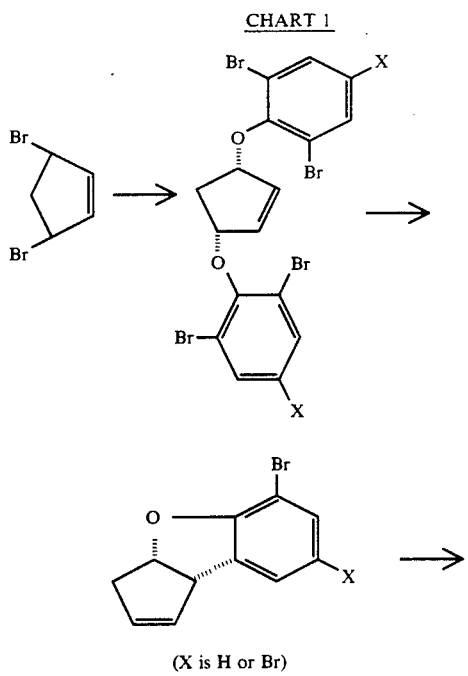

(X is H or Br)

-continued
CHART 1

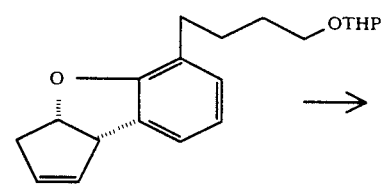

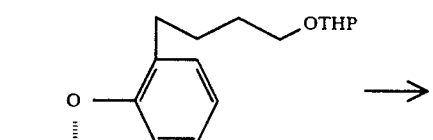

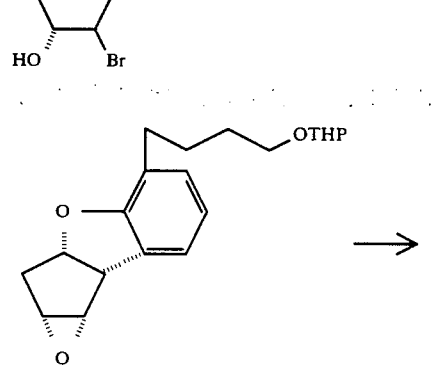

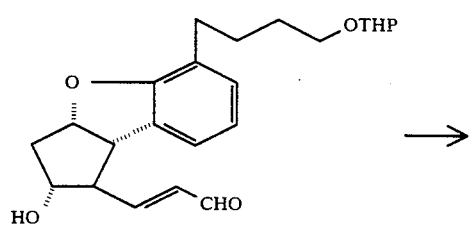

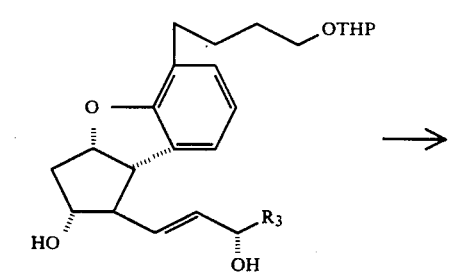

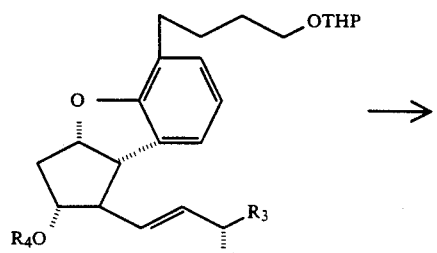

CHART 1
-continued
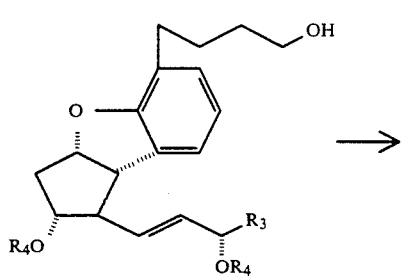
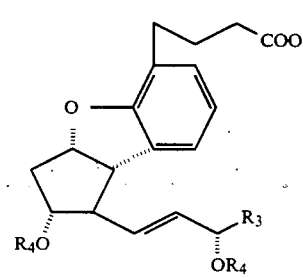
CHART 2
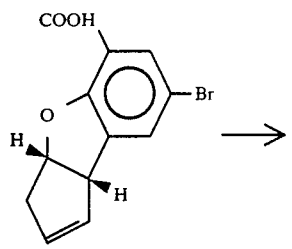
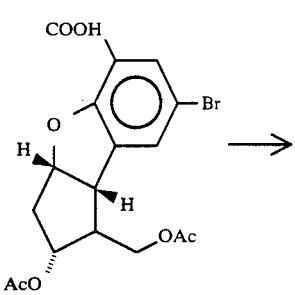
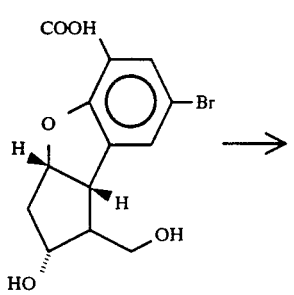
CHART 2
-continued
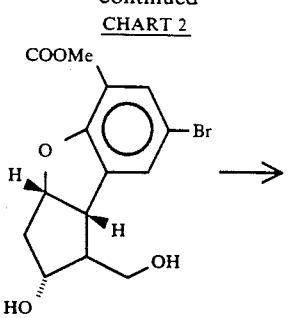
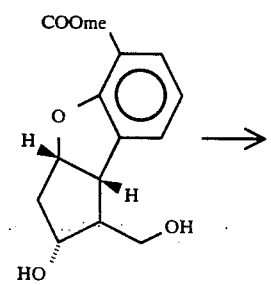
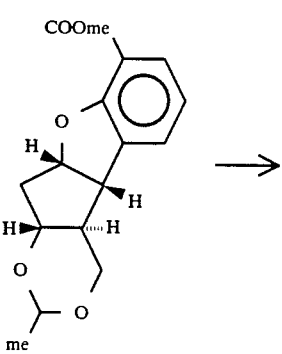
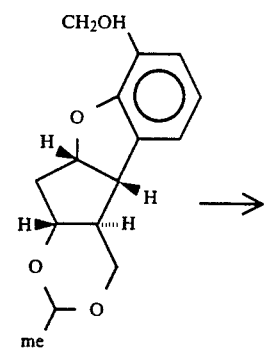
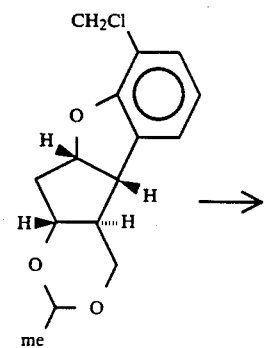

-continued
CHART 2
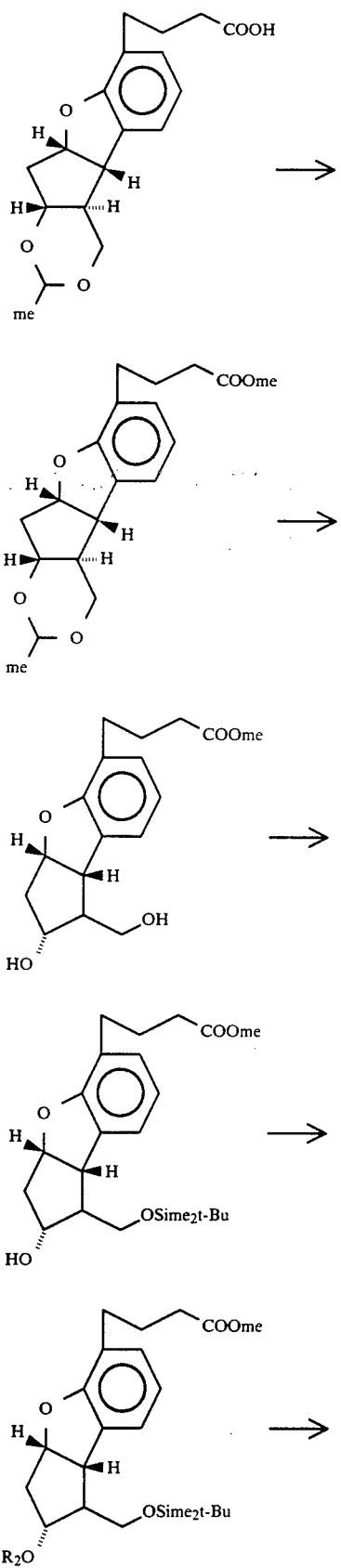
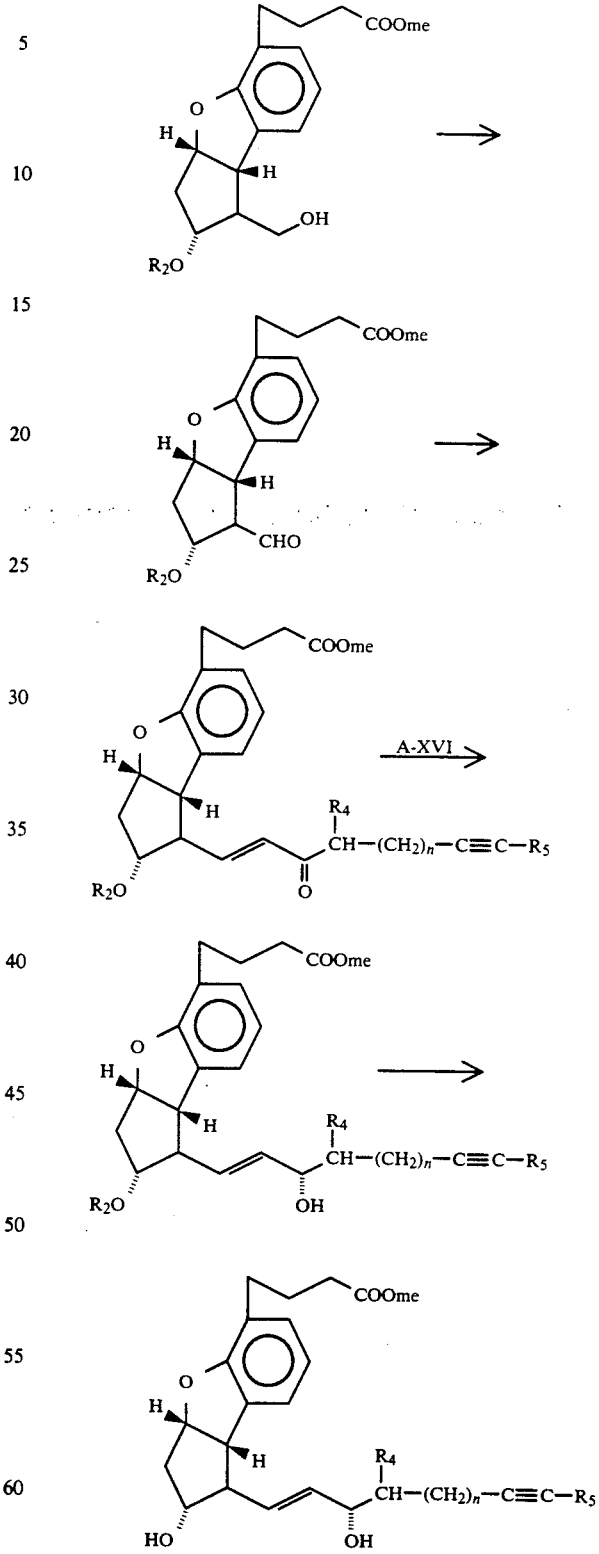
However, the conventional manufacturing processes described above have a variety of drawbacks which are disadvantageous in the industrial production in large scale, i.e., in that the reproducibility is poor, a large number of steps need to employ column chromatography, the stereoselectivity and the regiospecificity are poor, reactions which are carried out at low temperature are necessary, operation is troublesome, yield is low and so on.

DISCLOSURE OF THE INVENTION

Accordingly, the object of the present invention is to provide a novel manufacturing process of PGI$_2$ derivatives having m-phenylene structure which is excellent in the stereoselectivity, the regiospecificity, ease of operation and reproducibility.

The present inventors investigated intensively to find a novel process for synthesizing m-phenylene PGI$_2$ derivatives to accomplish this invention.

The present invention relates to a process for manufacturing 5,6,7-trinor-4,8-inter-m-phenylene PGI$_2$ derivatives represented by the formula [VII] as shown in Step A.

PGI$_2$ derivatives obtained by the method of the present invention are named based on the rules of nomenclature for prostaglandins and prostacycline analogues which is defined by N. A. Nelson et al. [N. A. Nelson, J. Med. Chem., 17, 911 (1974), and R. A. Johson, D. R. Morton, N. A. Nelson, Prostaglandins, 15, 787 (1978)]. The fundamental compound which has inter-m-phenylene structure in place of exo-enol ether structure of PGI$_2$ is represented by the following formula. The position numbers are assigned as shown in the following formula, and the compound is named 5,6,7-trinor-4,8-inter-m-phenylene PGI$_2$.

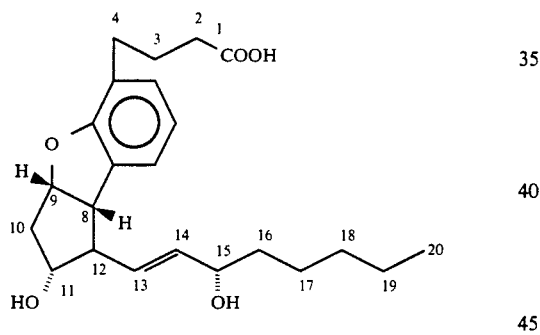

In accordance with this nomenclature, the compound represented by the following formula is named 16-methyl-18,19-tetradehydro-5,6,7-trinor-4,8-inter-m-phenylene PGI$_2$.

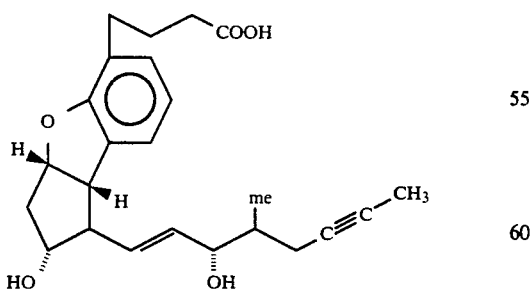

If this compound is named in accordance with the formal rule of nomenclature, it is named as a butyric acid derivative. In this case, the moiety of the condensed rings is named based on the 1H-cyclopenta[b]benzofuran of the formula:

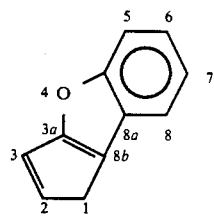

Thus, it is named 4-[2-endo-hydroxy-1-exo-(3-hydroxy-4-methyl-6,7-tetradehydro-1-octenyl)-3a,8b-cis-2,3,3a,8b-tetrahydro-1H-5-cyclopenta[b]benzofuranyl] butyric acid. In the present specification, the structural formula of the compound is shown to represent only one of the optical isomers. However, it is intended that these structural formulae include the d-, l- and dl-optical isomers and indication of the absolute configuration, i.e., the indication of R- and S- is omitted in the naming.

BEST MODE FOR CARRYING OUT THE INVENTION

The method of the present invention may be carried out in accordance with the following process shown in Step A.

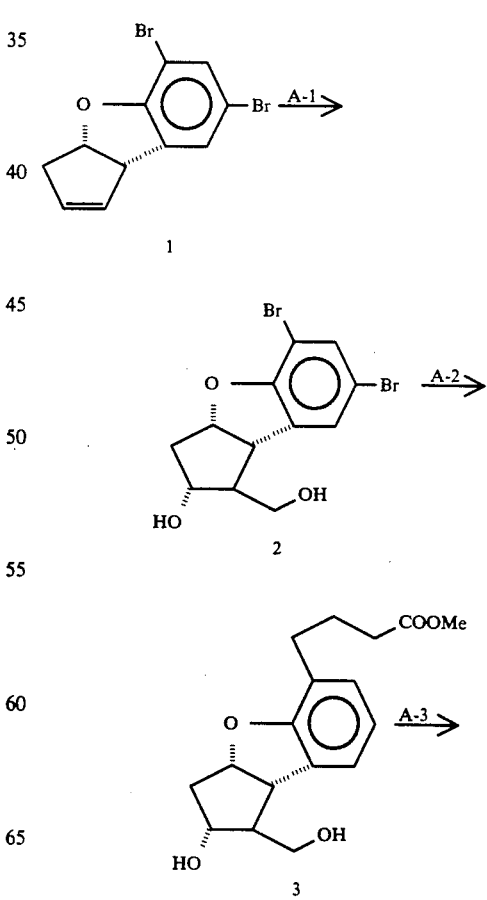

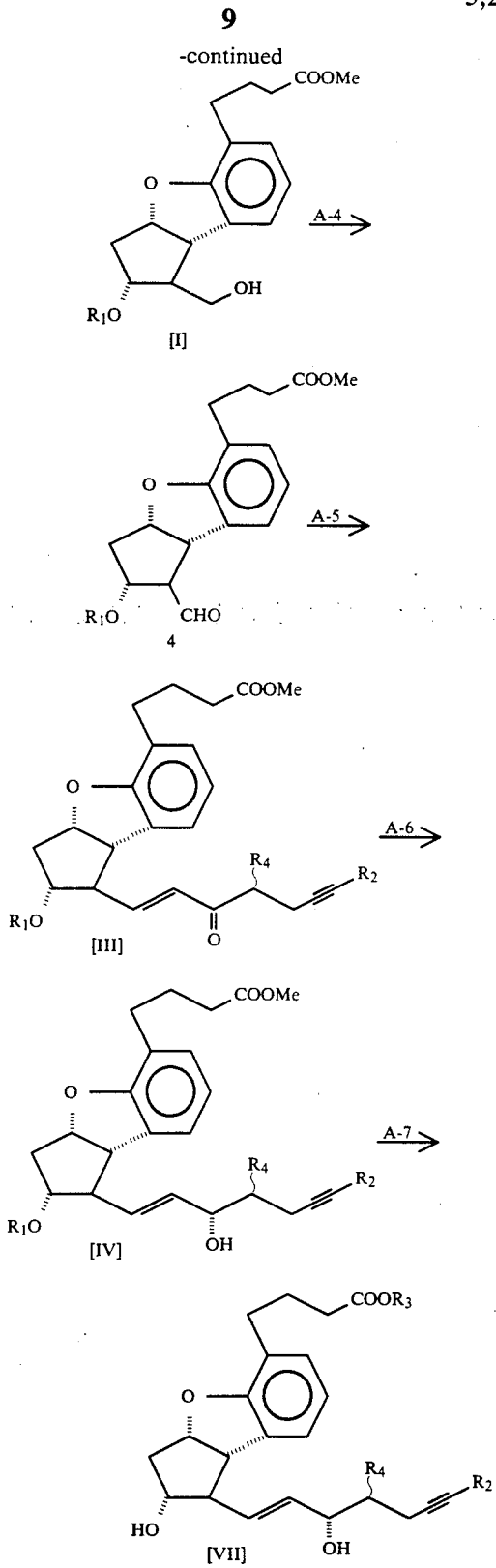

Each of the steps will now be described in detail.

Step A-1 is a process in which the dibromide (Compound 1) is converted to transdiacetate by so-called Prins reaction and then the reaction product is hydrolyzed to give a diol (Compound 2). Usually, Prins reaction is carried out by heating the dibromide and formalin or a compound equivalent to formalin in acetic acid solvent in the presence of an acid. Examples of the compound equivalent to formalin include paraformaldehyde and 1,3,5-trioxane. As a catalyst, sulfuric acid, chlorosulfonic acid, trichloroacetic acid, trifluoroacetic acid, tribromoacetic acid, perchloric acid, phosphoric acid and the like may be employed. Usually, sulfuric acid may be preferably employed. This reaction may be carried out at a temperature ranging from room temperature to 200° C. Usually, preferred reaction rate may be obtained at a temperature ranging from 60° to 90° C. After removing the solvent and solids originated from formaldehyde, the reaction product may be hydrolyzed with an alkali without purification. The hydrolysis may easily be conducted by dissolving the obtained product in a solvent such as methanol or ethanol and by adding thereto not less than 8 equivalents of an aqueous solution of sodium hydroxide, potassium hydroxide, sodium carbonate or potassium carbonate. The reaction product may be purified by column chromatography on silica gel.

Step A-2 is a process in which the dioldibromide (Compound 2) reacted with a Grignard reagent to exchange the bromine only on the 5th position of Compound 2 for magnesium halide, then this organometallic reagent reacted with methyl formylpropionate, and the resulting product is hydrolyzed so as to introduce an α-side chain. As the Grignard reagent, ethyl magnesium bromide, n-propyl magnesium bromide, isopropyl magnesium bromide, cyclohexyl magnesium bromide, ethyl magnesium chloride, n-propyl magnesium chloride, isopropyl magnesium chloride and cyclohexyl magnesium chloride may be employed. Among these, isopropyl magnesium bromide, cyclohexyl magnesium bromide and cyclohexyl magnesium chloride may preferably be employed. Preferred examples of the solvent employed in the Grignard exchange reaction include ethereal solvents such as ether, tetrahydrofuran (THF), 1,2-dimethoxyethane (DME) and dioxane. Among these, THF is especially preferred. The reaction may be carried out at a temperature ranging from −40° to 30° C., preferably −20° to 0° C. After removal of the solvent, the compound obtained by this reaction is dissolved in methanol and is subjected to hydrogenolysis in the presence of palladium-carbon as a catalyst and an acid. Examples of the acid may include mineral acids such as hydrochloric acid, hydrobromic acid, sulfuric acid and phosphoric acid, or organic acids such as oxalic acid and acetic acid. Usually, preferred results are obtained by using hydrochloric acid. Although the reaction may be carried out at a temperature ranging from −20° to 50° C., preferred results are obtained at room temperature. The purification may be conducted by silica gel column chromatography.

The step A-3 is a process of conducting the following three processes in one pot.
1) selective protection of the primary hydroxyl group,
2) esterification of the secondary hydroxyl group and
3) regeneration of the primary hydroxyl group The reagent employed for protection of the primary hydroxyl group may include t-butyldimethylsilyl chloride, trityl chloride, triphenylsilyl chloride, di-t-dibutylsilyl chloride, diphenylmethylsilyl chloride and the like. Among these, trityl chloride may be most preferably employed. As a solvent, ethereal solvents such as ether, THF, DME and dioxane; and aprotic solvents such as N,N-dimethylformamide (DMF) and the like may be preferably employed. Among these, although not limited, DMF may be preferably employed for silylation, and THF may be preferably employed for tritylation. This reaction may be preferably carried out in the presence of a base. Preferred examples of the base include triethylamine, pyridine and imidazole. Although not limited, imidazole may be preferably employed for silylation and triethylamine may be preferably employed for tritylation. The reagents employed for protection of the secondary hydroxyl group may include acetic anhydride, o-toluoyl chloride, p-toluoyl chloride, benzoyl chloride, m-toluoyl chloride, p-t-butylbenzoyl chloride, p-phenylbenzoyl chloride, 3,5-dinitrobenzoyl, N-phenylcarbamoyl, α-naphthoyl chloride, β-naphthoyl chloride and the like. Among these, p-toluoyl chloride may be most preferably employed. The removal of the protective group of the primary alcohol may be attained by using an acid catalyst. Examples of the acid may include mineral acids such as hydrochloric acid, sulfuric acid and nitric acid; sulfonic acids such as p-toluene sulfonic acid, methane sulfonic acid and d-10-camphor sulfonic acid; acetic acid, chloroacetic acid, bromoacetic acid, trifluoroacetic acid and the like. In general 1-6N hydrochloric acid-methanol may be preferably employed. The removal of the silyl group may be attained by using tetrabutylammonium fluoride in addition to the above-described acids. These reactions 1), 2) and 3) may be carried out at a temperature ranging from −20° to 100° C. However, the tritylation may be preferably conducted at a temperature of 50° to 90° C. In the other reactions, sufficient reaction rate may be obtained at room temperature. The product obtained by conducting the three reactions (one pot) may be purified by recrystallization after removing the reagents by short column chromatography or by a usual column chromatography. Especially, the compound represented by the formula [I] in which $R_1$ is p-toluoyl group may be easily purified by recrystallization.

Step A-4 is a process of oxidation of the alcohol to an aldehyde (Compound 4). The reagent employed in this reaction include, although not limited, anhydrous chromic acid-pyridine complex (Collins' reagent), dimethylsulfoxide/dicyclohexylcarbodiimides, dimethylsulfide/N-bromosuccinimides, dimethylsulfide/chlorine/base. The obtained aldehyde may be employed in the next reaction without further purification.

Step A-5 is a process of condensing the aldehyde and the lithium salt of the dimethylphosphonate represented by the following formula:

[II]

(wherein $R_2$ represents methyl or ethyl; and $R_4$ represents hydrogen atom or methyl) so as to obtain an α,β-unsaturated ketone (Compound [III]). The solvent employed in the reaction may include ethereal solvents such as ether, THF, DME and the like. Further, solvents other than the above-described solvents, which are employed in Wittig reaction, for example, DMSO and dialkylformamides may be preferably employed. The dimethylphosphonate may be synthesized in accordance with the following reaction (E. J. Corey et al. J. Am. Chem. Soc., 88, 5654 (1966)).

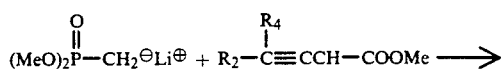

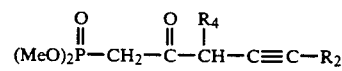

This reaction may be carried out at a temperature ranging from −78° to 80° C., preferably −20° to 30° C. The product (Compound [III]) obtained by this reaction may be purified easily by recrystallization after removal of the reagent by column chromatography on silica gel, or by a column chromatography usually employed in the art. Especially, Compound [III] having p-toluoyl group as $R_1$ may easily be purified by recrystallization.

Step A-6 is a process of reduction of the α,β-unsaturated ketone to an allyl alcohol. The preferred examples of the reducing agent employed in this reaction may include, although not limited, $Zn(BH_4)_2$, $LiAlH_4/α,α'$-binaphthol, diisopropyl aluminum (2,6-dimethylphenoxide), aluminum triisopropoxide, and $NaBH_4$-cerium chloride. When this reaction is carried out using $Zn(BH_4)_2$, $LiAlH_4/α,α'$-binaphthol or diisopropyl aluminum (2,6-dimethylphenoxide), ethereal solvents such as ether, THF, DME, dioxane and the like may be preferably employed as a solvent. Among these, THF is especially preferred. Further, when this reaction is carried out by using aluminum triisopropoxide, aromatic hydrocarbons such as benzene, toluene, xylene and the like may be preferably employed as a solvent. Among these, benzene may be most preferably employed. When the reaction is carried out using sodium borohydride-cerium chloride, although not limited, alcoholic solvents such as methanol, ethanol and the like may be preferably employed. Although the alcohol obtained in this reaction is the mixture of 15α and 15β epimers, only 15α epimer having high pharmacological activity may be employed in next step A-7. The pure 15α isomer may be obtained by silica gel column chromatography.

Step A-7 is a process of removing $R_1$ group of Compound [IV] by hydrolysis or methanolysis. In cases where the methanolysis is conducted, $R_3$ group of Compound [VII] is converted to methyl group. On the other hand, in cases where the hydrolysis is conducted, $R_3$ of Compound [VII] is converted to hydrogen atom. In the case of methanolysis, the reaction may be carried out easily by dissolution of Compound [IV] in methanol and followed by treatment with a base such as anhydrous potassium carbonate, anhydrous sodium carbonate or sodium methoxide. In the case of hydrolysis, the reaction may be carried out easily by dissolution of Compound [IV] in an alcoholic solvent such as methanol, ethanol or the like and followed by treatment with a base such as sodium hydroxide, potassium hydroxide, sodium carbonate, potassium carbonate or the like. However, the examples of solvent or base in the case of hydrolysis are by no means limited thereto. This reaction may be carried out at a temperature of ranging from 0° to 150° C., preferably 20° to 60° C. Usually, this reaction may be carried out easily at room temperature. Further, when hydrolysis is carried out, water-containing THF, water-containing dioxane, water-containing DME, water-containing DMSO or the like may be employed in addition to the above-described solvents.

In the present invention, the 15β isomer produced as a byproduct in the above-described Step A-6 has poor pharmacological activities. In view of improvement of the yield of the 15α isomer and reduction of the production cost, it is advantageous to efficiently convert the 15β isomer to the 15α one.

In the present invention, 15β isomer may be converted to 15α one efficiently by using the Mitsunobu reagent.

That is, this method comprises the two steps shown in Step B. In Step B, $R_1$, $R_2$ and $R_4$ represent the same meanings as mentioned above.

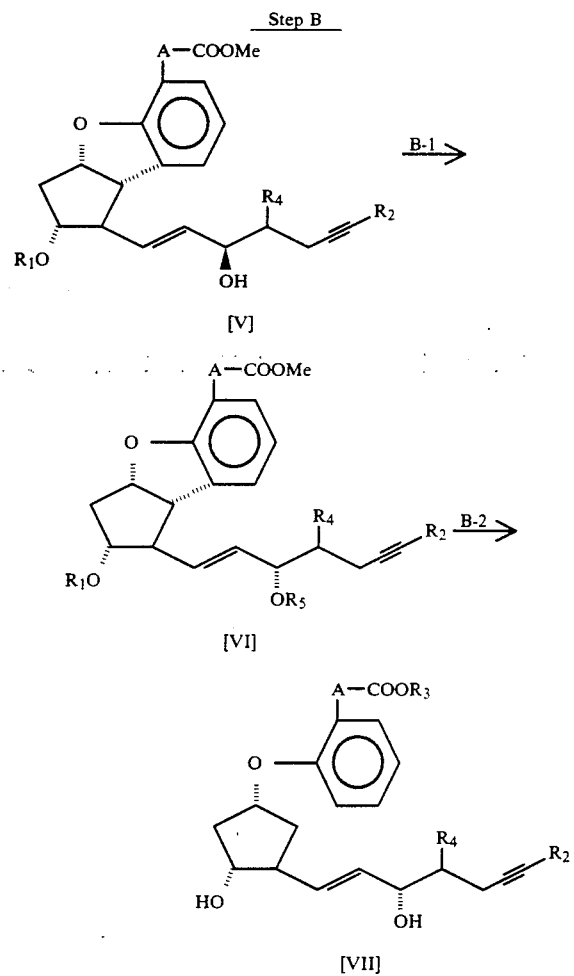

Step B-1 the Mitsunobu reaction in which the 15β hydroxyl is converted to the 15α one by $S_N2$ reaction using a carboxylic acid (O. Mitsunobu, M. Yamada, Bull. Chem. Soc. Jpn. 40, 2380 (1967)). The preferred examples of the carboxylic acid employed in this reaction may include, although not limited, acetic acid, propionic acid, butyric acid, isobutyric acid, valeric acid, hexanoic acid, nonanoic acid, decanoic acid, benzoic acid, p-methylbenzoic acid and p-phenylbenzoic acid. Among these, benzoic acid, valeric acid and butyric acid are especially preferred. The reaction may be carried out at a temperature of ranging from −40° to 100° C. Usually, this reaction may be carried out sufficiently at room temperature. As a solvent, ethereal solvents such as diethylether, tetrahydrofuran, dimethoxyethane and dioxane may be preferably employed. Among these, diethylether and THF are especially preferred. As the reagent employed in this reaction, a trialkyl or triaryl phosphine and a dialkylazodicarboxylate may be employed. Usually, triphenylphosphine and diethylazodicarboxylate may be preferably employed.

The reagent is used in an amount of 1–10 equivalents, and satisfactory results may be obtained by using 1.2 equivalents of the reagent. The obtained compound (Compound [VI]) may be employed in the next step without purification. In the formula [VI], $R_5$ represents $C_2$-$C_{10}$ acyl group or $C_7$-$C_{11}$ aroyl group.

Step B-2 is a process of conversion of Compound [VI] to Compound [VII] by hydrolysis or solvolysis. In the case where $R_1$ is ester, Step B-2 may be conducted easily by dissolution of Compound [VI] in a solvent and by using a base. Examples of the base may include hydroxides of alkali metals and alkaline earth metals such as potassium hydroxide, sodium hydroxide, barium hydroxide and calcium hydroxide; carbonates of alkali metals and alkaline earth metals such as calcium carbonate, barium carbonate, sodium carbonate and potassium carbonate; and $C_1$-$C_{12}$ alkoxides such as sodium alkoxide and potassium alkoxide. As the solvent, aqueous or anhydrous alcoholic solvents such as methanol, ethanol and the like may be employed. In the case where $R_1$ is alkylsilyl or arylsilyl group, after conduction of the above-described process, hydrolysis is carried out by use of an acid or a quaternary ammonium salt. Preferred examples of the acid employed in this reaction may include acetic acid, hydrochloric acid, sulfuric acid, hydrogen fluoride and the like. Preferred examples of the quaternary ammonium salt may include tetra-n-butylammonium fluoride, tetra-n-butylammonium chloride, pyridium hydrofluoride and the like. When acetic acid, hydrochloric acid or sulfuric acid is used, water-containing THF, diethylether, acetonitrile, methylene chloride, dimethylsulfoxide, methanol, ethanol or the like may preferably be employed as the solvent. When hydrogen fluoride, tetra-n-butylammonium fluoride, tetra-n-butylammonium chloride, pyridium hydrofluoride is employed, anhydrous THF, acetonitrile, methylene chloride, dioxane or the like may be employed as the solvent. Among these, desired results may be obtained by using acetic acid/water/THF solvent system. The obtained Compound VII hardly contains by-product such as 15β isomer and the like, and may be purified easily by column chromatography.

The above-described method for converting the 15β isomer to 15α one can be applied generally to inversion of the hydroxyl group on the 15th position in the compound represented by the following formula:

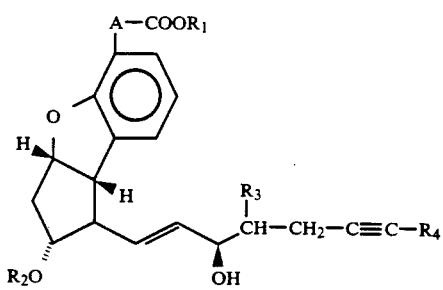

(wherein $R_1$ represents hydrogen atom or $C_1$-$C_{12}$ straight alkyl group; R2 represents $C_2$-$C_{10}$ acyl group, $C_7$-$C_{18}$ aloyl group, $C_3$-$C_{18}$ alkylsilyl group or $C_7$-$C_{18}$ arylsilyl group; $R_3$ represents hydrogen atom, methyl or ethyl group; R4 represents $C_1$-$C_5$ straight alkyl group; A represents
1) —CH₂—CH₂—CH2—
2) —CH₂—CH₂— or

3) —O—CH₂—)

by use of the Mitsunobu reagent, followed by solvolysis or hydrolysis to obtain 4,8-inter-m-phenylene PGI₂ derivative represented by the formula:

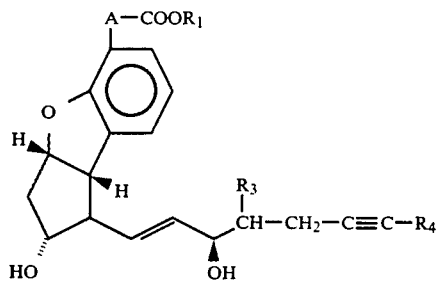

(wherein R₁, R₃, R₄ and A represent the same meanings as described above).

As to the above-described compound, preferred examples of R₂ which is $C_2$-$C_{10}$ acyl group include, although not limited, acetyl, propionyl, butyroyl, octanoyl, decanoyl and valeroyl groups. Although preferred examples of R₂ which is $C_7$-$C_{13}$ aroyl group may include benzoyl, α-naphthoyl, β-naphthoyl, p-toluoyl, o-toluoyl, m-toluoyl, p-phenylbenzoyl, the examples are by no means limited thereto. Although preferred examples of R₂ which is $C_3$-$C_{18}$ silyl group may include trimethylsilyl, t-butyldimethylsilyl, t-butyldiphenylsilyl, diphenylmethylsilyl, di-t-butylsilyl, triphenylsilyl and the like, the examples are by no means limited thereto.

By this method, the 15β isomer having poor activity may be converted efficiently to the 15α one having high activity in high yield. Further, when compared with the conventional method in which hydroxyl group on the 15th position is oxidized by using an oxidant such as manganese dioxide, chromic acid or the like to form a ketone and then the ketone on the 15th position is reduced by using a reductant such as sodium borohydride, the above-described method is excellent in that it produces less impurities and gives higher yield, and the use of a heavy metal which brings about an industrial problem of disposition is eliminated.

In the present invention, although the method for preparing the starting material 3a,8b-cis-dihydro-3H-5,7-dibromocyclopenta[b]benzofuran (Compound I) is not restricted, it is preferred to prepare it by the following two methods:

A firstly method can be carried out by the process shown in Step C.

Firstly, step C-1 is a process of reacting 3,5-cis-dibromocyclopentene (Compound 5) (W. G. Young. et al., J. Am. Chem. Soc., 78, 4338 (1956)) and alkali metal salt of o-halophenol in the presence of a phase transfer catalyst to obtain 3,5-cis-bis(2-halophenoxy)cyclopentene (Compound 6). Preferred examples of alkali metal include sodium, potassium and the like. Among these, potassium is especially preferred. Examples of the halophenol include 2-chlorophenol, 2-bromophenol and 2-iodophenol. Preferred examples of the solvent may include ethereal solvents such as diethylether, THF, DME and dioxane; aromatic hydrocarbons such as toluene and benzene; aprotic solvents such as dimethylformamide and acetonitrile. Among these, THF is especially preferred. Preferred examples of the phase transfer catalyst may include those described in the literature "Phase transfer catalyst" (W. P. Weber and G. W. Kokel, translated by I. Tafushi and T. Nishitani, p.309, Kagakudojin). Among these, tetrabutyl ammonium bromide, 18-crown-6 may be preferably employed in this reaction. However, the examples of the phase transfer catalyst are by no means limited thereto. This reaction may be carried out at a temperature of −78°–50° C., preferably −30°–30° C. Usually, satisfactory results may be obtained by carrying out the reaction at room temperature. The reaction time may be 1–60 hours, usually 2–40 hours. The Compound 6 is obtained as precipitates because the solubility thereof is small.

Step C-2 is a process of converting Compound 6 to 3a,8b-cis-dihydro-3H-cyclopenta[b]benzofuran (Compound 7) by intramolecular cyclization. That is, Compound 6 (in the formula, X represents chlorine, bromine or iodine) dissolved in a solvent is added to dry magnesium metal in a solvent to form a di-Grignard reagent. Examples of Compound 6 include 3,5-bis(2-bromophenoxy)cyclopentene, 3,5-bis(2-chlorophenoxy)cyclopentene and 3,5-bis(2-iodophenoxy)cyclopentene. Examples of the solvent include ethereal solvents such as diethylether, THF, DME and diglyme; and aromatic hydrocarbons such as benzene, toluene and xylene. Among these, ethereal solvents are usually employed and THF is especially preferred. Magnesium is used in an amount of 1–5 equivalents, preferably 2–2.2 equivalents. This reaction may be carried out at a temperature of ranging from −20° to 100° C., preferably 20°–60° C.

A catalytic amount of a metal compound is then added to the solution of di-Grignard reagent so as to attain the intramolecular cyclization to give 3a,8b-cis-dihydro-3H-cyclopenta[b]benzofuran (Compound 7). As the metal catalyst, nickel chloride, cuprous chloride, cuprous bromide, cuprous iodide, cuprous cyanide, palladium chloride or the like may be employed. Among these, cuprous compounds, especially cuprous iodide, may be preferably employed. However, the examples of metal catalyst are by no means limited thereto. This reaction may preferably be carried out at a temperature of ranging from −20° to 100° C., more preferably 30° to 50° C. Compound 7 may be isolated by distillation or silica gel column chromatography. In case of treating a large amount of the compound, isolation by distillation is preferred. In step C-2, the reaction can be carried out at room temperature using cheap and easy to handle magnesium in comparison with the conventional method which necessitates the use of expensive and troublesome n-BuLi at a low temperature, so that synthetic operation is easy and the cost is low.

Step C-3 is a process of converting Compound 7 to tetrabromide by bromination. That is, Compound 8 may be prepared by dissolving Compound 7 in a solvent and adding bromine to this solution. As the solvent employed in this reaction, halogenated solvents such as dichloromethane, chloroform, carbon tetrachloride; carbon disulfide; acetic acid; and cyclohexane may be employed. Among these, dichloromethane and chloroform may be preferably employed. The amount of bromine to be used varies depending on whether a Friedel-Crafts catalyst is employed or not. That is, in case of use of no catalyst, 3–10 equivalents, preferably 4–6 equivalents of the bromine may be employed. In case of use of the catalyst, 3–6 equivalents, preferably 3–3.2 equivalents of bromine may be employed. Preferred examples of the Friedel-Crafts catalyst employed in this reaction may include iron, ferric chloride, ferric bromide, aluminum chloride, aluminum bromide, zinc chloride, antimony (III) chloride and the like. Among these, iron and aluminum bromide are especially preferred. The catalyst may be used in an amount of 0.001–0.5 equivalent, more preferably 0.007–0.015 equivalent. When no catalyst is used, the reaction may be carried out at a temperature of ranging from −20° to 100° C., preferably 20° to 60° C. When the catalyst is used, the reaction may preferably be carried out at a temperature of 0° to 30° C. In cases where the catalyst is not employed, the reaction may be carried out for 10 minutes to one week. In particular, when 4 equivalents of bromine is used, the reaction time may be 12 hours to one day, and when not less than 5 equivalents of bromine is used, the reaction may preferably be carried out for 10 minutes to 3 hours. In cases where the catalyst is employed, the reaction may be carried out for 1 minute to one week, preferably 30 minutes to one day. As to other reaction conditions, although not restricted, the reaction may be preferably carried out in the absence of a light. Compound 8 may be isolated by recrystallization or silica gel column chromatography. However, since the reaction proceeds quantitatively, the obtained product may be employed in the next reaction without purification. By this step, Compound 8 may be prepared easily in high yield and with good reproducibility.

Step C-4 is a process of regenerating a double bond by reductively removing the bromine in the five-membered ring moiety of the tetrabromide (Compound 8). This reaction may be conducted by one of three methods each of which employs 1) zinc, 2) sodium thiosulfate or 3) sodium sulfide as a reductant. When zinc is used, this reaction may be conducted in accordance with the following conditions: That is, tetrabromocyclopenta[b]benzofuran is dissolved in a solvent and zinc is added thereto so as to obtain 3a,8b-cis-dihydro-3H-5,7-dibromocyclopenta[b]benzofuran (Compound 1). Usually, zinc may be used in an amount of 1–10 equivalents, preferably 1–4 equivalents. Preferred examples of the solvent employed in the reaction include methanol, ethanol, acetic acid, THF, DMF, dimethylether and diglyme, as well as mixed solvents such as acetic acid-THF, acetic acid-diethylether. Among these, acetic acid and the mixed solvent of acetic acid-THF may be preferably employed. This reaction may be carried out at a temperature of ranging from 0° to 150° C. for 10 minutes to one day, more preferably at a temperature of ranging from 20° to 60° C. for 10 minutes to 3 hours.

In cases where the method using sodium thiosulfate is employed, the reaction may be conducted in accordance with the method described in a literature (K. M. IbneRasa, A. R. Tahir, A Rahman, Chem. Ind., 1973, 232). In this reaction, 1–10 equivalents, preferably 2–4 equivalents of sodium thiosulfate may be employed. As the solvent, dipolar aprotic solvents such as DMF, DMSO and the like may be employed. Among these, DMSO may be more preferably employed. This reaction may be carried out at a temperature of ranging from 0° to 150° C. for 10 minutes to 3 days, preferably at a temperature of ranging from 80° to 100° C. for 30 minutes to 2 hours.

In cases where the method using sodium sulfide is employed, the reaction may be conducted in accordance with the process described in a literature (K. Fukunaga, H. Yamaguchi, Synthesis, 1981, 897, D. Landini, L. Milesi, M. L. Quardri, and F. Rolla, J. Org. Chem., 49, 157 (1984), J. Nakayama, H. Machida and M. Hoshino, Tetrahedron Lett., 1983, 3001). As the solvent, dipolar aprotic solvents such as DMSO, DMF and the like may be used alone or a mixed solvent of dichloromethane, hexane, benzene or toluene/water/a phase transfer catalyst may be employed. Among these, dipolar aprotic solvents such as DMSO, DMF and the like may preferably be employed individually. Preferred examples of the phase transfer catalyst include tetra-n-butyl ammonium bromide, hexadecyltributylphosphonium bromide, trioctylmethyl ammonium chloride, 15-crown-5 and the like. Among these, trioctylmethyl ammonium chloride is especially preferred. This reaction may be carried out at a temperature of ranging from 20° to 150° C. for one minute to 3 days. When DMSO or DMF is used, this reaction may be preferably carried out at a temperature of ranging from 20° to 40° C. for one minute to one hour. Compound 1 may be isolated by recrystallization or silica gel column chromatography irrespective of the debrominating agent used.

Compound 1 employed in the present invention as a starting material may be synthesized by another method shown in Step D.

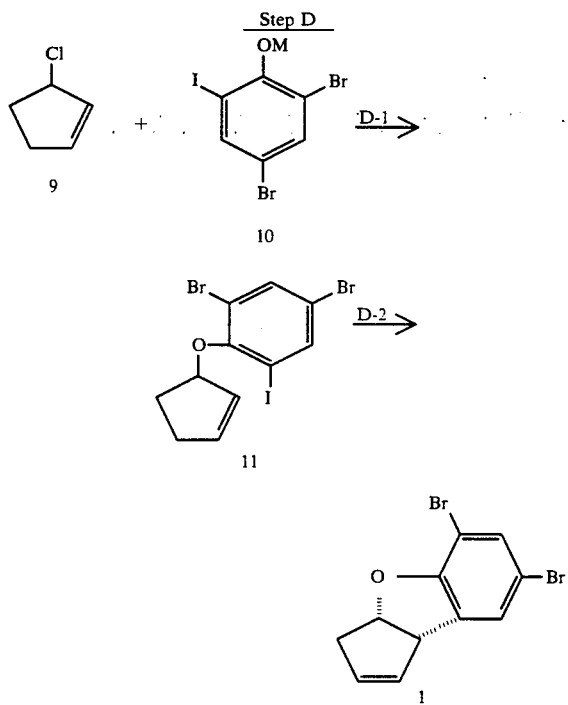

Step D-1 is a process of preparing 3-(2,4-dibromo-6-iodophenoxy)cyclopentene (Compound 11) by reacting 3-chlorocyclopentene (Compound 9) with 2,4-dibromo-6-iodophenyl (Compound 10) (in the formulae, M represents sodium or potassium). Compound 9 is easy to prepare (R. B. Moffett, Org. Syn., coll. vol. IV, 238). Preferred examples of a solvent employed in this reaction include ethereal solvents such as diethylether, THF and 1,2-dimethoxyethane dioxane; aromatic hydrocarbon solvents such as toluene and benzene; dipolar aprotic solvents such as dimethylformamide and acetonitrile. Among these, dimethylformamide is especially preferred. Preferred examples of the phase transfer catalyst include those described in the literature "W. P. Weber and G. W. Kokel, translated by Iwao TABUSHI and Takako NISHITANI, "Phase Transfer Catalyst", p309, Kagakudojin). Among these, tetrabutyl ammonium bromide, 18-crown-6 and the like are especially preferred. However, the examples of phase transfer catalyst are by no means limited thereto. This reaction may preferably be carried out at a temperature of ranging from −78° to 50° C., more preferably ranging from −30° to 30° C. Usually, the satisfactory results may be obtained by carrying out the reaction at room temperature. This reaction may be carried out for 1–60 hours, usually 2–40 hours. Compound 11 may be purified by recrystallization, distillation or column chromatography on silica gel to a pure compound.

Step D-2 is a process of preparing cyclopenta[b]benzofuran derivative (Compound 1) by reacting Compound 11 with a palladium complex and phosphorus ligand in the presence of a base. In this reaction, Compound 11 is suspended in a solvent together with the palladium complex, phosphorus ligand and an appropriate base and this mixture is sufficiently stirred so as to allow the reaction.

Examples of the solvent employed in this reaction include amines such as triethylamine, diisopropylethylamine; ethereal solvents such as ether, THF and 1,2-dimethoxyethane; aromatic hydrocarbonsolvents such as toluene and benzene; dipolar aprotic solvents such as dimethylformamide and acetonitrile. Among these, acetonitrile is especially preferred. Examples of the palladium complex include those described in the literature (R. F. Heck, "Palladium Reagents in Organic Synthesis"; Acad. Press; New York (1985)). Among these, Pd(0) complex such as tetrakistriphenylphosphine palladium, bisdibenzylideneaceto palladium; and Pd(II) complexes such as palladium acetate and palladium chloride may be employed. Usually, palladium acetate is employed. However, the examples of the palladium complexes are by no means limited thereto. The preferred examples of phosphorus ligand employed in this reaction may include monodentate alkylphosphines such as trimethylphosphine and triethylphosphine; monodentate arylphosphines such as triphenylphosphine and tris-o-toluphosphine; bidentate phosphines such as bis(diphenylphosphino)methane, 1,2-bis(diphenylphosphino)ethane and 1,3-bis(diphenylphosphino)propane; and phosphites such as trimethylphosphite and triethylphosphite. In general, triphenylphosphine is employed. As the base employed in this reaction, amines such as triethylamine and diisopropylamine; basic acetates such as sodium acetate, potassium acetate and silver acetate; basic carbonates such as sodium hydrogen carbonate and silver carbonate may be preferably employed. Among these, silver carbonate is especially preferred. However, the examples of the base are by no means limited thereto.

The reaction may be carried out at a temperature ranging from −78° to 150° C., usually −30° to 120° C. for 1 to 100 hours, usually 4 to 50 hours. After conducting the reaction, palladium is separated by filtration and then the filtrate is subjected to column chromatography on silica gel to obtain the Compound 1.

The above-described method may be applied more generally to the preparation of cyclopenta[b]benzofuran derivative of the formula:

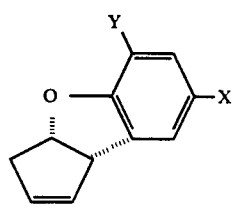

(wherein X and Y represent hydrogen or halogen) by reacting 3-phenoxypentene derivative of the formula:

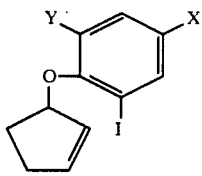

(wherein X and Y represent the same meaning as described above) with the palladium complex in the presence of the phosphorus ligand and the base. The 3-phenoxy derivative is prepared by reacting 3-chlorocyclopentene with a phenol derivative of the formula:

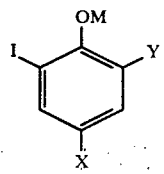

(wherein X and Y represent the same meaning as described above, M represents sodium or potassium).

By this method, Compound 1 may be prepared with high yield and high reproducibility. Further, unlike the conventional method, this method does not necessitates an organic metal reagent and low temperature conditions. Still further, since the isomerization of olefin is attained in the practical level and the cost of palladium is low because only a catalytic amount of palladium is required in this reaction, so that this method is excellent in preparing Compound 1 industrially.

EXAMPLES

The present invention will now be described in more detail by way of examples thereof. However, the present invention is not limited thereto.

COMPARATIVE EXAMPLE 1

3,5-cis-dibromocyclopentene

In 400 ml of n-hexane, 2128 g (32.19 mol) of cyclopentadiene was dissolved and 4 ml of ethanol was added thereto, followed by being cooled down to $-78°$ C. Then 1616 ml (31.55 mol) of bromine was added dropwise slowly to the mixture for 3.5 hours. After the resulting mixture was stirred at a temperature of $-40°$—$-55°$ C. for 3 hours, the precipitated crystals were filtrated under suction to obtain pale yellow or orange crystals. The thus obtained crystals were stocked in a freezer until it was employed in the next reaction.

Yield: 2299.55 g (32.2%)

NMR (CDCl$_3$) δ: 2.79 (1H, d, J=16.78 Hz), 2.97-3.06 (1H, m), 5.10 (2H, d, J=16.72 Hz), 6.20 (2H, d, J=0.97 Hz)

EXAMPLE 1

3,5-cis-bis(2-bromophenoxy)cyclopentene

In 6.1 l of methanol, 610.5 g (9.248 mol) of KOH (85%) was dissolved and this solution was cooled in iced water and then 1600.1 g (9.248 mol) of o-bromophenol in 1 l of methanol was added thereto for an hour. After evaporation of the solvent, the residue was subjected to azeotropic distillation with 800 ml of THF to give anhydrous residue and the resultant was dried by using a vacuum pump.

The yield of potassium salt of o-bromophenol was 2067.0 g (105.9%).

The thus obtained potassium salt of o-bromophenol was dissolved in 2.6 l of THF and 14.90 g (46.2 mmol) of n-Bu$_4$NBr was added thereto, followed by being cooled in iced water. Then 1096.9 g (4.855 mol) of 3,5-cis-dibromocyclopentene was dissolved in 1.1 l of THF and this solution was cooled in iced water. This solution was added to the previously obtained mixture at one time and the resulting mixture was stirred overnight under cooling in iced water. To the thus obtained reaction mixture, 1.2 l of water was added and the resulting mixture was stirred. After evaporating the solvent, the precipitated crystals were washed with 1N aqueous solution of NaOH (5 l×2), water (5 l×2), 3 l of methanol, 2 l of cyclohexane and n-hexane (500 ml×2). The thus obtained crystals were dried by using a vacuum pump to obtain the captioned compound.

Yield: 1352.0 g (71.3%)

m. p.: 138.0°-138.5° C.

NMR (CDCl$_3$) δ: 2.21 (1H, dd, J=14.0, 5.0 Hz), 3.08 (1H, dd, J=14.0, 7.0 Hz), 5.20 (1H, dd, J=7.0, 5.0 Hz), 6.30 (2H, s), 6.80-7.50 (8H, m)

IR (KBr) ν cm$^{-1}$: 1585, 1570, 1165, 992, 790

Elementary Analysis Calcd: C; 49.66 H; 3.68, Found : C; 49.76 H; 3.56.

The same procedure as in Example 1 was repeated expect that o-chlorophenol or o-iodophenol was employed in place of o-bromophenol to obtain 3,5-cis-bis(2-chlorophenoxy)cyclopentene or 3,5-cis-bis(2-iodophenoxy)cyclopentene, respectively.

EXAMPLE 2

3a,8b-cis-dihydro-3H-cyclopenta[b]benzofuran

To 1.3 g (53.5 mmol) of dried magnesium, 10 ml of dry THF was added and then an aliquote of a solution of 10 g (24.4 mmol) of 3,5-cis-bis(2-bromophenoxy)cyclopentene in 70 ml of THF was added to this solution. After the resulting mixture was heated to prepare a Grignard reagent, the remaining THF solution was added thereto and the resulting mixture was stirred at room temperature. Then the thus obtained reaction mixture was added to 65.2 g (2.68 mol) of dried magnesium and 0.5 l of dry THF was added thereto, and then 500 g (1.22 mol) of 3,5-bis(2-bromophenoxy)cyclopentene in 3.5 l of THF was gradually added thereto. After the addition, the resulting mixture was heated at 50 ° C. for an hour, followed by being cooled in iced water. To the thus obtained reaction mixture, 11.6 g (60.9 mmol) of CuI was added and the resulting mixture was heated at 40 ° C. for an hour, followed by being colled in iced water. To the thus obtained reaction mixture, 0.9 l of 3N aqueous solution of NaOH was added and the resulting mixture was filtered through Hyflo Super-Cel. The thus obtained solid was washed with 2.5 l of THF and the filtrate was concentrated. The concentrate was extracted four times with 1 liter of cyclohexane, washed with 2N aqueous solution of NaOH (0.25 l×2) and with brine (0.1 l×3) and dried over anhydrous magnesium sulfate. If the interface between organic layer and aqueous layer was not clear during the extraction and washing steps, the mixture was filtered through Hyflo Super-Cel. Then magnesium sulfate was removed by filtration and the obtained organic layer was concentrated. The same procedure was repeated except to employ 816 g (1.99 mol) of 3,5-cis-bis(2-bromophenoxy)cyclopentene, and the obtained concentrate was combined with the previously obtained concentrate, followed by distillation of the combined concentrates.

Yield: 377.0 g (73.7%)

b. p.: 77.8°–78.8 ° C./0.1 mmHg

NMR (CDCl₃) δ: 2.80 (1H, dd, J=2.2, 0.5 Hz), 2.82 (1H, dd, J=5.2, 0.5 Hz), 4.35 (1H, d, J=7.8 Hz), 5.43 (1H, ddd, J=7.8, 5.2, 2.2 Hz), 5.71 (2H, s), 6.95 (4H, m)

IR (neat) ν cm⁻¹: 3060, 1602, 1582

Mass: 158 (M+)

In the procedure of Example 2, the captioned compound is also obtained by using 3,5-cis-bis(2-chlorophenoxy)cyclopentene or 3,5-cis-bis(2-iodophenoxy)cyclopentene in place of 3,5-cis-bis(2-bromophenoxy)cyclopentene. Further, in the procedure of Example 2, the captioned compound is obtained by using cuprous chloride, cuprous bromide, cuprous cyanide, palladium chloride or nickel chloride in place of cuprous iodide.

EXAMPLE 3

3a,8b-cis-2,3,3a,8b-tetrahydro-1H-1,2,5,7-tetrabromocyclopena[b]benzofuran

In 20 ml of dichloromethane, 2.0156 g (12.7 mmol) of 3a,8b-cis-dihydro-3H-cyclopenta[b]benzofuran was dissolved and this solution was cooled in iced water and then 3.9 ml (76.2 mmol) of bromine was added slowly thereto. After stirring the mixture at room temperature for an hour, the thus obtained reaction mixture was added to 100 ml of saturated aqueous sodium hydrogen carbonate solution which was cooled in iced water. Under stirring, 4.7 g of sodium thiosulfate in 10 ml of water was added slowly to the reaction mixture. After confirming that the color of bromine was disappeared, the mixture was extracted twice with 50 ml of ethyl acetate. The organic layers were washed with 50 ml of brine and dried over anhydrous sodium sulfate. After removing sodium sulfate by filtration, the resultant was concentrated and dried under reduced pressure to obtain brown sticky liquid.

Yield: 6.2725 g (103.8%)

Ten point one milligrams of the thus obtained sticky liquid was subjected to thin layer chromatography to separate diastereomer to obtain 6.4 mg of 4A from low polar fractions and 3.9 mg of 4B from high polar fractions.

(4A) White Crystals m. p.: 117.0°–119.0 ° C.

NMR (CDCl₃) δ: 2.69–2.78 (1H, m), 3.11–3.22 (1H, m), 4.37–4.43 (1H, m), 4.43–4.51 (1H, m), 4.55–4.62 (1H, m), 5.52–5.60 (1H, m), 7.32–7.41 (1H, m), 7.49 (1H, d, J=1.95 Hz)

IR (KBr) ν cm⁻¹: 2970, 1452, 1258, 1187, 1135, 1058, 992, 804, 714

Mass (EI Method, m/e): 472 (M+)

High resolution mass spectrum

Calcd (C₁₁H₈OBr₄, M+): 471.7309

Found (M+): 471.7323

(4B) white crystals m. p.: 110.0°–112.0° C.

NMR (CDCl₃) δ: 2.59–2.70 (1H, m), 2.97 (1H, ddd, J=15.13, 5.37, 3.42 Hz), 4.35 (1H, t, J=7.82 Hz), 4.40 (1H, t, J=5.86 Hz), 4.57–4.64 (1H, m), 5.46–5.53 (1H, m), 7.34 (1H, s), 7.50 (1H, d, J=1.95 Hz)

IR (KBr) ν cm⁻¹: 2970, 1455, 1263, 1161, 1013, 867, 812

Mass (EI Method, m/e): 472 (M+)

High resolution mass spectrum

Calcd. (C₁₁H₈OBr₄, M+): 471.7309

Found (M+): 471.7349

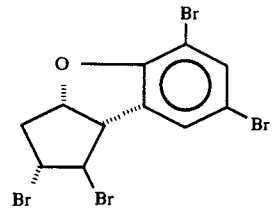

(4A)

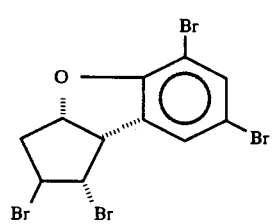

(4B)

EXAMPLE 4

3a,8b-cis-2,3,3a,8b-tetrahydro-1H-1,2,5,7-tetrabromocyclopenta[b]benzofuran

In 1 l of dichloromethane, 100 g (0.632 mol) of 3a,8b-cis-dihydro-3H-cyclopenta[b]benzofuran was dissolved and 353 mg (6.32 mmol) of iron was added thereto, followed by being cooled in iced water. To the mixture, 100 ml (1.96 mol) of bromine was added slowly and the resulting mixture was stirred at rooom temperature for 21 hours. The reaction mixture was cooled in iced water and 160 g (1.90 mol) of sodium hydrogen carbonate and 1 l of water were added thereto. Under stirring, 7.8 g (0.0314 mol) of sodium thiosulfate was added to the reaction mixture to separate aqueous layer and organic layer. The aqueous layer was extracted with 2 l of ethyl acetate and the combined organic layer was washed with 1 l of water and with 1 l of saturated aqueous sodium chloride solution and dried over anhydrous magnesium sulfate. After removing magnesium sulfate by filtration, the filtrate was concentrated to obtain a solid and the solid was dried under reduced pressure.

Yield: 298.7 g (99.7%)

GC purity: 93%

EXAMPLE 5

3a,8b-cis-dihydro-3H-5,7-dibromocyclopenta[b]benzofuran

In 10 ml of DMSO, 687.3 mg (1.372 mmol, purity:95.0% of 3a,8b-cis-2,3,3a,8b-tetrahydro-1H-1,2,5,7-tetrabromocyclopenta[b]benzofuran was dissolved and 1.022 g (4.12 mmol) of pulverized sodium thiosulfate was added thereto, followed by being heated at 100° C. for an hour. After allowing the solution to cool at room temperature, 30 ml of ethyl acetate and 30 ml of water were added to the reaction mixture for extraction. Then the obtained aqueous layer was extracted with 10 ml of ethyl acetate and the organic layers were washed with 20 ml of saturated aqueous sodium chloride solution and dried over anhydrous sodium sulfate. After removing sodium sulfate by filtration, the filtrate was concentrated to dryness.

Yield: 447.0 mg

GC purity: 96.3% m. p.: 108.0°–109.0° C.

NMR (CDCl$_3$) δ: 2.90 (2H, m), 4.48 (1H, m), 5.60 (1H, m), 5.80 (2H, m), 7.25 (1H, d, J=2.0 Hz), 7.40 (1H, d, J=2.0 Hz)

IR (KBr) ν cm$^{-1}$: 3070, 2980, 2920, 1595, 1570, 865, 830, 740, 720

Mass: 314 (M$^+$), 316 (M$^+$ +2), 318 (M$^+$ +4)

EXAMPLE 6

3a,8b-cis-dihydro-3H-5,7-dibromocyclopenta[b]benzofuran

In 50 ml of DMF, 5.00 g (10.51 mmol) of 3a,8b-cis-2,3,3a,8b-tetrahydro-1H-1,2,5,7-tetrabromocyclopenta[b]benzofuran was dissolved and 5.05 g (21.02 mmol) of sodium sulfide was added thereto and the resulting mixture was stirred at room temperature for 4 hours. To the reaction mixture, 50 ml of water was added and the resultant was extracted with 50 ml of ethyl acetate. Then aqueous layer was extracted twice with 30 ml of ethyl acetate and the combined organic layer was washed with 50 ml of water (10 ml of saturated aqueous sodium chloride solution was added because the separation was not easy) and with 50 ml of saturated aqueous sodium chloride solution and dried over anhydrous magnesium sulfate. After removing sodium sulfate by filtration, the filtrate was concentrated to obtain a solid.

Yield: 3.20 g

GC yield: 87.6%

EXAMPLE 7

3a,8b-cis-dihydro-3H-5,7-dibromocyclopenta[b]benzofuran

In 10 ml of THF and 10 ml of acetic acid, 3.00 g (6.31 mmol) of 3a,8b-cis-2,3,3a,8b-tetrahydro-1H-1,2,5,7-tetrabromocyclopenta[b]benzofuran was dissolved and 0.8657 g (13.2 mmol) of zinc was added thereto and the resulting mixture was stirred at room temperature for an hour. The thus obtained reaction mixture was filtered and the solvent was evaporated. To the residue, 20 ml of water and 20 ml of ethyl acetate were added for extraction. Further, aqueous layer was extracted twice with 20 ml of ethyl acetate and the combined organic layer was washed with 20 ml of water and with 20 ml of saturated aqueous sodium chloride solution, and dried over anhydrous magnesium sulfate. After removing magnesium sulfate by filtration, the filtrate was concentrated to obtain a solid.

Yield: 1.95 g (97.5%)

GC purity: 96.6% m. p.: 108.0°–109.0° C.

NMR (CDCl$_3$) δ: 2.90 (2H, m), 4.48 (1H, m), 5.60 (1H, m), 5.80 (2H, m), 7.25 (1H, d, J=2.0 Hz), 7.40 (1H, d, J=2.0 Hz)

IR (KBr) ν cm$^{-1}$: 3070, 2980, 2920, 1595, 1570, 865, 830, 740, 720

Mass: 314 (M$^+$), 316 (M$^+$ +2), 318 (M$^+$ +4)

EXAMPLE 8

3-(2,4-dibromo-6-iodophenoxy)cyclophenten

In 100 ml of ethanol, 48.5 g (128 mmol) of 2,4-dibromo-6-iodophenol was dissolved and this solution was cooled down to 0° C. under cooling in iced water. To this solution, 115 ml (128 mmol) of 1.12M potassium hydroxide in ethanol was added dropwise to obtain potassium salt thereof. The solvent was evaporated and the residue was dried under heating and under reduced pressure (0.5 mmHg, 60° C., 16 hours). In 150 ml of dimethylformamide, 53.2 g (128 mmol) of the resultant was dissolved and 0.68 g (2.6 mmol) of 18-crown-6 was added to this solution. To the resulting mixture, 11.8 g (115 mmol) of 3-chlorocyclopenten was added dropwise using a dropping funnel and the resulting mixture was stirred for 2.5 hours at room temperature (20° C.). The thus obtained reaction mixture was poured to a separating funnel containing 300 ml of ethyl acetate and 100 ml of 1N aqueous sodium hydroxide solution. The organic layer was washed with 100 ml of 1N sodium hydroxide and with 150 ml of saturated aqueous sodium chloride solution and dried over sodium sulfate. After evaporating the solvent, the thus obtained solid was recrystallized from ethanol to obtain 41.6 g (105 mmol) of 3-(2,4-dibromo-6-iodophenoxy)cyclopentene with 82% yield.

m.p. 57°–58° C.

IR (KBr) ν cm$^{-1}$: 2900, 1520, 1425, 1360, 1105, 1020, 990, 930, 910, 880, 810, 780, 710

NMR (400 MHz, CDCl$_3$) δ: 2.1–2.8 (4H, m), 5.4–5.6 (1H, m), 5.7–6.0 (1H, m), 6.0–6.3 (1H, m), 7.68 (1H, d, J=2.3 Hz), 7.87 (1H, d, J=2.3 Hz)

MS (CI) 459 (M$^+$ +NH$_3$)

The same procedure as in Example 8 except that 2-bromo-6-iodophenol is employed in place of 2,4-dibromo-6-iodophenol yields 3-(2-bromo-6-iodophenoxy)cyclopentene.

The same procedure as in Example 8 except that 4-bromo-2-iodophenol, 2-bromo-4-chloro-6-iodophenol, 4-bromo-2-chloro-6-iodophenol or 2,4,6-triiodophenol is employed in place of 2,4-dibromo-6-iodophenol yields 3-(4-bromo-2-iodophenoxy)cyclopentene, 3-(2-bromo-4-chloro-6-iodophenoxy)cyclopentene, 3-(4-bromo-2-chloro-6-iodophenoxy)cyclopentene or 3-(2,4,6-triiodophenoxy)cyclopentene, respectively.

COMPARATIVE EXAMPLE 2

3-(2,4-dichloro-6-iodophenoxy)cyclopentene

In 20 ml of methanol, 6.3 g (21.8 mmol) of 2,4-dichloro-6-iodophenol was dissolved and this solution was cooled to 0° C. under cooling in iced water. To this solution, 6.5 ml (21.8 mmol) of 3.33M potassium hydroxide in methanol was added dropwise to form potassium salt thereof. The solvent was evaporated and the resultant was dried by heating under reduced pressure (0.5 mmHg, 60° C., 16h). The thus obtained solid was dissolved in 30 ml of dimethylformamide and 0.12 g (0.45 mmol) of 18-crown-6 was added thereto. In 7.5 ml of DMF, 2.2 g (19.6 mmol) of 3-chlorocyclopentene was dissolved and this solution was added dropwise to the previously obtained mixture using a dropping funnel, followed by being stirred at room temperature (20° C.) for 14 hours. The reaction mixture was poured to a separating funnel containing 20 ml of ether and 30 ml of 1N aqueous sodium hydroxide solution. The thus obtained organic layer was washed with 1N aqueous sodium hydroxide solution (20 ml×2) and with 20 ml of saturated aqueous sodium chloride solution, and dried over sodium sulfate. The solvent was evaporated and the thus obtained oily product was purified by column chromatography of silica gel to obtain 5.4 g (15.3 mmol, 70%) of 3-(2,4-dichloro-6iodophenoxy)cyclopentene.

IR (KBr) ν cm$^{-1}$: 2910, 1525, 1435, 1360, 1100, 1010, 1000, 995, 930, 925, 890, 800, 780, 715

NMR (400 MHz, CDCl$_3$) δ: 2.2–2.8 (4H, m), 5.4–5.6 (1H, m), 5.9–6.1 (1H, m), 6.1–6.3 (1H, m), 7.41 (1H, d, J=2.5 Hz), 7.74 (1H, d, J=2.5 Hz)

MS (CI) 371 (M$^+$ +NH$_3$)

The same procedure as in Comparative Example 2 except that 2-iodophenol, 2-chloro-6-iodophenol or 4-chloro-2-iodophenol is employed in place of 2,4-dichloro-6-iodophenol yields 3-(2-iodophenoxy)cyclopentene, 3-(2-chloro-6-iodophenoxy)cyclopentene or 3-(4-chloro-2-iodophenoxy)cyclopentene, respectively.

EXAMPLE 9

3a,8b-cis-dihydro-3H-5,7-dibromocyclophenta[b]benzofuran

In Schlenk's type reactor, 300.5 mg (0.67 mmol) of 3-(2,4-dibromo-6-iodophenoxy)cyclopenten, 7.8 mg (0.035 mmol) of palladium acetate, 22.2 mg (0.089 mmol) of triphenylphosphine and 102.5 mg (0.37 mmol) of silver carbonate were suspended in 5 ml of acetonitrile. This suspension was allowed to react at 25° C. for 20 hours under argon atmosphere and the thus obtained mixture was filtered through Celite, followed by being washed with ethyl acetate. After evaporating the solvent, the residue was analyzed by gass chromatography using di-n-propyl phthalate as an internal standard to obtain chemical yield of 70% and a ratio of the captioned compound and olefin isomer thereof of 30:1. The residue was purified by column chromatography of silica gel (eluant:cyclohexane:ethyl acetate=50:1) to obtain 3a,8b-cis-dihydro-3H-5,7-dibromocyclophenta[b]benzofuran.

IR (KBr) ν cm$^{-1}$: 3070, 2970, 2920, 1570, 1450, 1245, 1220, 1150, 1000, 950, 860, 830, 805, 740, 710

NMR (400 MHz, CDCl$_3$) δ: 2.85–2.95 (2H, m , 4.46 (1H, d, J=7.3 Hz), 5.53–5.60 (1H, m), 5.69–5.73 (1H, m), 5.80–5.85 (1H, m), 7.23 (1H, dd, J=2.1, 0.6 Hz), 7.38 (1H, d, J=1.8 Hz)

MS (EI) 314 (M$^+$)

The same procedure as in Example 9 except that 3-(2-bromo-6-iodophenoxy)cyclopentene is employed in place of 3-(2,4-dibromo-6-iodophenoxy)cyclopentene yields 3a,8b-cis-dihydro-3H-5-bromocyclopenta[b]benzofuran.

The same procedure as in Example 9 except that 3-(4-bromo-2-iodophenoxy)cyclopentene, 3-(2-bromo-4-chloro-6-iodophenoxy)cyclopentene, 3-(4-bromo-2-chloro-6-iodophenoxy)cyclopentene or 3-(2,4,6-triiodophenoxy)cyclopentene is employed in place of 3-(2,4-dibromo-6-iodophenoxy)cyclopentene yields 3a,8b-cis-dihydro-3H-7-bromocyclopenta[b]benzofuran, 3a,8b-cis-dihydro-3H-5-bromo-7chlorocyclopenta[b]benzofuran, 3a,8b-cis-dihydro-3H-7-bromo-5-chlorocyclopenta[b]benzofuran or 3a,8b-cis-dihydro-3H-5,7-diiodocyclopenta[b]benzofuran, respectively.

COMPARATIVE EXAMPLE 3

3a,8b-cis-dihydro-3H-5,7-dichlorocyclopenta[b]benzofuran

In Schlenk's type reactor, 228.7 mg (0.68 mmol) of 3-(2,4-dichloro-6-iodophenoxy)cyclopenten, 7.6 mg (0.035 mmol) of palladium acetate, 35.4 mg (0.135 mmol) of triphenylphosphine and 102.3 mg (0.37 mmol) of silver carbonate were suspended in 5 ml of acetonitrile. This suspension was allowed to react at 25° C. for 20 hours under argon atmosphere and the thus obtained mixture was filtered through Celite, followed by being washed with ethyl acetate. After evaporating the solvent, the residue was analyzed by $^1$HNMR (400 MHz) using di-n-propyl phthalate as an internal standard to obtain chemical yield of 68% A ratio of the captioned compound and olefin isomer therof was 25:1 on gas chromatography analysis. The residue was purified by column chromatography (silica gel, eluant:cyclohexane:ethyl acetate=30:1) to obtain 3a, 8b-cis-dihydro-3H-5,7-dichlorocyclophenta[b]benzofuran.

IR (KBr) ν cm$^{-1}$: 2980, 2920, 1575, 1435, 1240, 1235, 1220, 1140, 1050, 985, 940, 855, 830, 805, 740, 710

NMR (400 MHz, CDCl$_3$) δ: 2.88–2.92 (2H, m), 4.43 (1H, d, J=7.1 Hz), 5.56–5.60 (1H, m), 5.68–5.72 (1H, m), 5.80–5.82 (1H, m), 7.08 (1H, dd, J=2.0 Hz), 7.14 (1H, d, J=2.0 Hz)

MS (EI) 226 (M$^+$)

The same procedure as in Comparative Example 3 except that 3-(2-iodophenoxy)cyclopentene, 3-(2-chloro-6-iodophenoxy)cyclopentene or 3-(4-chloro-2-iodophenoxy)cyclopentene is employed in place of 3-(2,4- dichloro-6-iodophenoxy)cyclopentene yields 3a,8b-cis-dihydro-3H-cyclopenta[b]benzofuran, 3a,8b-cis-dihydro-3H-5-chlorocyclopenta[b]benzofuran or 3a,8b-cis-dihydro-3H-7-chlorocyclopenta[b]benzofuran, respectively.

EXAMPLE 10

5,7-dibromo-2-endo-hydroxy-1-exo-hydroxymethyl-3a,8b-cis-2,3,3a,8b-tetrahydro-1H-cyclopenta[b]benzofuran In 400 ml of acetic acid, 33 g of 3a,8b-cis-dihydro-5,7-dibromocyclopenta[b]benzofuran and 66 g of s-trioxane were dissolved and 30 ml of concentrated sulfuric acid was added thereto under stirring at 80° C., followed by being stirred for 15 hours. After cooling the reaction mixture, acetic acid was evaporated and 1000 ml of ethyl acetate was added thereto, followed by being washed with 500 ml of water and with saturated aqueous sodium carbonate solution (500 ml×5). The washes were extracted with 500 ml of ethyl acetate and ethyl acetate layers were combined, dried and concentrated to obtain 46 g of an oily product. The thus obtained oily product was dissolved in 400 ml of methanol and 160 ml of 3N aqueous sodium hydroxide solution was added thereto, followed by being stirred at room temperature for 30 minutes. After concentration, 50 ml of 6N hydrochloric acid was added to the reaction mixture and the resultant was extracted with ethyl acetate (300 ml, 1100 ml×2). The extrates were combined, washed with water (200 ml, 100 ml) and with 100 ml of saturated aqueous sodium chloride solution, dried and concentrated to 30 g of an oily produnct. The thus obtained oily product was recrystallized from n-hexane and ethyl acetate (50 ml:25 ml) to 16 g (42% yield) of colorless crystals (m. p.: 126°–128° C.). Further, mother liquor was concentrated and was purified by column chromatography of silica gel (eluant; cyclohexane:ethyl acetate=2:1→ethy acetate) to 8.1 g (21% yield) of the captioned compound.

NMR (CDCl$_3$) δ: 2.05 (2H, m), 2.54 (1H, m), 3.68 (3H, m), 4.04 (3H, m), 5.24 (1H, ddd, J=9.5, 7.2, 5.0 Hz), 7.22 (1H, d, J=2.0 Hz), 7.39 (1H, d, J=2.0 Hz)

IR (KBr) ν: 3300, 2970, 2925, 2870, 1600, 1575, 750, 730 cm$^{-1}$

Mass (m/e): 336 (M$^+$ +4), 364 (M+2), 362 (M$^+$)

The same procedure as in Example 10 except that paraformaldehyde is employed in place of trioxane yields the captioned compound.

EXAMPLE 11

4-(2-endo-hydroxy-1-exo-hydroxymethyl-3a,8b-cis-2,3,3a,8b-tetrahydro-1H-cyclopenta[b]benzofuran-5-yl)butiric acid methyl ester Under argon atmosphere, to 175 ml of THF containing 35 g of 5,7-dibromo-2-endo-hydroxy-1-exo-hydroxymethyl-3a,8b-cis-2,3,3a,8b-tetrahydro-1H-cyclopenta[b]benzofuran, 109 ml of 1.82M cyclohexyl magnesium chloride in THF was added dropwise at 0° C. for 40 minutes and the resulting mixture was stirred at room temperature for 30 minutes. To the thus obtained reaction mixture, 54 ml of 1.82M cyclohexyl magnesium chloride was added and the resulting mixture was stirred at 40° C. for 3 hours.

Under argon atmosphere, 190 ml of THF containing 3-formyl propionic acid methyl ester was stirred at −20° C. and the previously obtained Grignard reagent was added thereto for 15 minutes, followed by being stirred at −5°–0° C. for 10 minutes. To the thus obtained reaction mixture, 25 ml of concentrated hydrochloric acid (about 35%) was added and the resulting mixture was concentrated and dissolved in 300 ml of methanol. The pH of this solution was adjusted to 2–3 by adding concentrated hydrochloric acid and 3.0 g of 10% palladium-charcoal was added thereto and the resulting mixture was stirred vigorously for 14 hours under hydrogen atmosphere. The thus obtained reaction mixture was filtered and the pH of the filtrate was adjusted to 7–8 by adding saturated aqueous sodium hydrogen carbonate solution, followed by being concentrated. To the residue, 100 ml of 1N hydrochloric acid and 50 ml of saturated aqueous sodium chloride solution were added and the resulting mixture was extracted with ethyl acetate. The extrates were combined, washed with water and saturated aqueous sodium chloride solution, dried and concentrated to about 50 g of an oily product. The thus obtained oily product was purified by column chromatography (silica gel 300 g, eluant; cyclohexane:ethyl acetate=1:1→ethyl acetate) to obtain 30 g of nearly pure captioned compound.

This compound was recrystallized from n-hexane/ethyl acetate (12 ml:15 ml) to obtain 15.2 g (52% yield) of crystals. Further, mother liquor was concentrated and was purified by column chromatography to obtain 9.7 g (33% yield) of the captioned compound.

NMR (CDCl$_3$) δ: 1.7–2.7 (11H, m), 3.40 (1H, dd, J=7.0, 8.0 Hz), 3.64 (3H, s), 3.7–4.2 (3H, m), 5.10 (1H, m), 6.76 (1H, t, J=7.5 Hz), 6.98 (2H, m)

IR (KBr) ν: 3350 (3600–3000), 1735, 1600, 755 cm$^{-1}$

Mass (m/e): 306 (M+)

The same procedure as in Example 11 except that ethyl magnesium bromide, n-propyl magnesium bromide, isopropyl magnesium bromide, cyclohexyl magnesium bromide, ethyl magnesium chloride, n-propyl magnesium chloride or isopropyl magnesium chloride is employed in place of cyclohexyl magnesium chloride also yields the captioned compound.

EXAMPLE 12

4-[2-endo-hydroxy-1-exo-t-butyldimethylsilyloxymethyl-3a,8b-cis-2,3,3a,8b-tetrahydro-1H-5-cyclopenta[b]benzofuranyl] butiric acid methyl ester In 6.8 ml of anhydrous DMF, 900 mg of 4-[2-endohydroxy-1-exo-hydroxymethyl-3a,8b-cis-2,3,3a,8b-tetrahydro-1H-5-cyclopenta[b]benzofuranyl] butiric acid methyl ester was dissolved and under cooling in iced water, 543 mg of imidazole and 636 mg (1.3 eq) of t-butyldimethylsilyl chloride were added thereto, followed by being stirred at room temperature for 3 hours. To the reaction mixture, ether/pentane (1:1) was added and then saturated aqueous sodium hydrogen carbonate solution was added thereto, followed by being extracted 3 times with ether/pentane (1:1). The organic layers were combined, washed with saturated aqueous sodium chloride solution, dried and concentrated to obtain 1.2 g of an oily product. The obtained oily product was employed in the next process without purification.

EXAMPLE 13

4-[2-endoacetoxy-1-exo-t-butyldimethylsilyloxymethyl-3a,8b-cis-2,3,3a,8b-tetrahydro-1H-5-cyclopenta[b]benzofuranyl] butyric acid methyl ester In 20 ml of acetic anhydride and 10 ml of anhydrous pyridine, 1.2 g of 4-[2-endo-hydroxy-1-exo-t-butyldimethylsilyloxymethyl-3a,8b-cis-2,3,3a,8b-tetrahydro-1H-5-cyclopenta[b]benzofuranyl] butiric acid methyl ester in the form of an oily product was dissolved and the resultant was stirred at room temperature for 14 hours. After removing acetic anhydride acid and pyridine from the reaction mixture (by using a vacuum pump), the residue was subjected 3 times to azeotropic distillation with toluene. The obtained oily product was employed in the next process without purification.

NMR (CDCl$_3$) δ: 0.92 (6H, s), 1.70 (3H, s), 1.80–2.70 (9H), 3.67 (3H, s), 3.70 (1H, m), 5.02 (1H, m), 5.25 (1H, m), 6.80 (1H, t, J=8.0 Hz), 6.95 (2H, m)

Mass (m/e) 462 (M+)

EXAMPLE 14

4-[2-endoacetoxy-1-exo-hydroxymethyl-3a,8b-cis-2,3,3a,8b-tetrahydro-1H-5-cyclopenta[b]benzofuranyl] butiric acid methyl ester In 10 ml of acetic acid and 5 ml of THF, 1.3 g of 4-[2-endoacetoxy-1-exo-t-butyldimethylsilyloxymethyl-3a,8b-cis-2,3,3a,8b-tetrahydro-1H-5-cyclopenta[b]benzofuranyl] butiric acid methyl ester in the form of a crude oily product was dissolved and 4 ml of water was added thereto, followed by being stirred at 50° C. for 14 hours. The reaction mixture was concentrated by using a vacuum pump and the residue was subjected 3 times to azeotropic distillation with toluene. The thus obtained oily product was purified by column chromatography (Lobar column (silica gel) commercially available from Merck Co., Inc., eluant; ethyl acetate/cyclohexane (1:1) to obtain 598 mg of pure captioned compound (yield when calculated from the starting material in Example 12 was 64%).

IR (neat) ν: 3450, 1740, 1595, 1240, 745 cm$^{-1}$

NMR (CDCl$_3$) δ: 1.82 (3H, s), 1.82–2.80 (1H), 3.66 (3H, s), 3.70 (3H, m), 5.00–5.35 (2H, m), 6.80 (3H, t, J=7.0 Hz)

Mass (m/e): 348 (M+)

EXAMPLE 15

4-[2-endoacetoxy-1-exo-hydroxymethyl-3a,8b-cis-2,3,3a,8b-tetrahydro-1H-5-cyclopenta[b]benzofuranyl] butyric acid methyl ester In 50 ml of anhydrous THF, 5 g (0.016 mol) of 4-[2-endohydroxy-1-exo-hydroxymethyl-3a,8b-cis-2,3,3a,8b-tetrahydro-1H-5-cyclopenta[b]benzofuranyl] butiric acid methyl ester was dissolved and 7.5 ml of anhydrous triethylamine (obtained by distillating over calcium hydride) was added thereto and then 7 g of trityl chloride was added thereto, followed by being stirred at room temperature for 24 hours. To the reaction mixture, 2 ml of triethylamine and 2 g of trityl chloride were added and the resulting mixture was stirred for 14 hours. To the thus obtained reaction mixture, 13.8 ml of acetic anhydride and 10.6 ml of anhydrous pyridine (dried over potassium hydroxide) were added and the resulting mixture was stirred at room temperature for 14 hours. The thus obtained reaction mixture was cooled in iced water and the pH thereof was adjusted to 1 by adding 55 ml of 3.7N hydrochloric acid in methanol, followed by being stirred at room temperature for 4 hours. To the reaction mixture, 23.2 g of sodium hydrogen carbonate was added portionwise under cooling in iced water and under stirring to adjust the pH to about 6. The thus obtained reaction mixture was concentrated and ethyl acetate was added to the residue and the resultant was stirred for a while. After dissolving the desired product, the solid was separated by filtration. The separated solid was washed with ethyl acetate and filtrate was separated. Water layer was extracted 3 times with ethyl acetate and organic layers were combined, washed with 6N hydrochloric acid, water and saturated aqueous sodium chloride solution, dried over sodium sulfate and concentrated to obtain 15.8 g of an oily product. The thus obtained oily product was purified by column chromatography (silica gel, eluant; ethyl acetate/cyclohexane (1:1)) to obtain 4.4 g (78 % yield) of the captioned compound.

EXAMPLE 16

4-[2-endo-hydroxy-1-exo-trityloxymethyl-3a,8b-cis-2,3,3a,8b-tetrahydro-1H-5-cyclopenta[b]benzofuranyl] butiric acid methyl ester In 1 ml of anhydrous THF, 100 mg of 4-[2-endohydroxy-1-exo-hydroxymethyl-3a,8b-cis-2,3,3a,8b-tetrahydro-1H-5-cyclopenta[b]benzofuranyl] butyric acid methyl ester was dissolved and 97 mg of trityl chloride and 0.1 ml of triethylamine were added thereto, followed by being stirred at room temperature for 20 hours. Then 20 mg of trityl chloride was added the reaction mixture and the resulting mixture was stirred at room temperature for 14 hours. Ethyl acetate and water were added to the reaction mixture and then the resulting mixture was extracted 3 times with ethyl acetate. Ethyl acetate layers were combined, washed with water and saturated aqueous sodium chloride solution, dried and concentrated. The thus obtained oily product was purified by column chromatography (silica gel, eluant; ethyl acetate/cyclohexane (1:9)) to obtain 167 mg (93% yield) of the captioned compound as a pure product.

NMR (CDCl$_3$) δ:
1 70–2.70 (9H), 3.30 (3H, m), 3.60 (3H, s , 4.00 (1H, m), 5.00 (1H, m), 6.80 (3H, m), 7.30 (15H, m)

Mass (m/e): 548 (M+)

EXAMPLE 17

4-[2-endo-acetoxy-1-exo-hydroxymethyl-3a,8b-cis-2,3,3a,8b-tetrahydro-1H-5-cyclopenta[b]benzofuranyl] butyric acid methyl ester In 3.5 ml of anhydrous DMF, 350 mg of 4-[2-endo-hydroxy-1-exo-hydroxymethyl-3a,8b-cis-2,3,3a,8b-tetrahydro-1H-5-cyclopenta[b]benzofuranyl] butylic acid methyl ester was dissolved and under cooling in iced water, 140 mg of imidazole and 360 mg of t-butyldimethylsilyl chloride were added thereto. After stirring the resulting mixture at room temperature for 3 hours, DMF was removed by using vacuum pump. The thus obtained residue was subjected 3 times to azeotropic distillation with benzene and the resultant was dissolved in 10 ml of acetic anhydride and 5 ml of anhydrous pyridine, followed by being stirred at room temperature for 2 hours. The thus obtained reaction mixture was concentrated and the residue was dissolved in 5 ml of acetic acid and then 5 ml of THF and 2 ml of water were added thereto, followed by being stirred at 50° C. for 14 hours. The reaction mixture was concentrated and the residue was subjected twice to azeotropic distillation with toluene and purified by column chromatography (silica gel, eluant; ethyl acetate/cyclohexane (1:2)) to obtain 280 mg (70% yield) of pure captioned compound.

IR (neat) ν: 3450, 1740, 1595, 1240, 745 cm$^{-1}$

NMR (CDCl$_3$) δ: 1.82 (3H, s), 1.82–2.80 (10H), 3.66 (3H, s), 3.70 (3H, m), 5.00–5.35 (2H, m), 6.80 (3H, t, J=7.0 Hz), 6.95 (2H, m)

Mass (m/e): 348 (M+)

EXAMPLE 18

4-[2-endo-benzoyloxy-1-exo-hydroxymethyl-3a,8b-cis-2,3,3a,8b-tetrahydro-1H-5-cyclooenta[b]benzofuranyl] butyric acid methyl ester In 250 ml of anhydrous THF, 30.4 g (0.1 mol) of 4-[2-endo-hydroxy-1-exo-hydroxymethyl-3a,8b-cis-2,3,3a,8b-tetrahydro-1H-5-cyclopenta[b]benzofuranyl] butyric acid methyl ester and 33.5 g (0.12 mol) of trityl chloride were dissolved and then 33.3 ml (0.24 mol) of triethylamine was added thereto, followed by being stirred for 6 hours under refluxing THF. The reaction mixture was cooled down to room temperature and 14.6 ml (0.18 mol) of pyridine and 20.9 ml (0.18 mol) of benzoyl chloride were added thereto, followed by being stirred for 8 hours under refluxing THF. The thus obtained reaction mixture was cooled in iced water and 350 ml of methanol and 60 ml of 4.35N hydrochloric acid/methanol were added thereto. After stirring the resulting mixture at room temperature for about an hour, 21.9 g (0.26 mol) of NaHCO$_3$ was added thereto and the resulting mixture was stirred for an hour. The thus obtained reaction mixture was concentrated under reduced pressure and the residue was dissolved in 300 ml of ethyl acetate and 100 ml of water, followed by being separated. The aqueous layer was extracted twice with 150 ml of ethyl acetate. Then organic layers were washed with 3N hydrochloric acid (100 ml×1) and with 10% saline (100 ml×4) and dried over anhydrous magnesium sulfate. After removing magnesium sulfate by filtration, the filtrate was concentrated under reduced pressure and 78.8 g of the concentrate was purified by column chromatography (silica gel; Art 7734 500 g commercially available from Merck Co., Inc., eluant; ethyl acetate/cyclohexane (1:2)) to obtain 31.3 g (76.2% yield) of the captioned compound.

EXAMPLE 19

4-[2-endo-o-toluoyloxy-1-exo-hydroxymethyl-3a,8b-cis-2,3,3a,8b-tetrahydro-1H-5-cyclopenta[b]benzofuranyl] butyric acid methyl ester In 250 ml of anhydrous THF, 19.9 g (0.065 mol) of 4-[2-endo-hydroxy-1-exo-hydroxymethyl-3a,8b-cis-2,3,3a,8b-tetrahydro-1H-5-cyclopenta[b]benzofuranyl] butyric acid methyl ester and 27.2 g (0.0975 mol) of trityl chloride were dissolved and then 27.1 ml (0.195 mol) of triethylamine was added thereto and the resulting mixture was stirred for 3 hours under refluxing THF. After cooling the reaction mixture to room temperature, 13.1 ml (0.161 mol) of pyridine and 25 g (0.161 mol) of o-toluoylchloride were added thereto and the resulting mixture was stirred for 10 hours under refluxing THF. The thus obtained reaction mixture was cooled in iced water and 400 ml of methanol and 40 ml (0.44 mol) of 11N hydrochloric acid were added thereto. After stirring the mixture at room temperature for about an hour, 37 g (0.44 mol) of NaHCO$_3$ was added thereto and the resulting mixture was stirred for 30 minutes. The thus obtained reaction mixture was subjected to the same workup procedure as in Example 18 to obtain 70 g of the concentrate. The concentrate was purified by column chromatography of silica gel (silica gel; Art 7734, 350 g, commercially available from Merck Co., Inc., eluant; ethyl acetate/cyclohexane (1:2)) to obtain 21.5 g (77.9% yield) of the captioned compound.

EXAMPLE 20

4-[2-endo-m-toluoyloxy-1-exo-hydroxymethyl-3a,8b-cis-2,3,3a,8b-tetrahydro-1H-5-cyclopenta[b]benzofuranyl] butyric acid methyl ester The same reaction conditions, workup procedure and purification as in Example 19 were repeated except that m-toluoylchloride was employed in place of o-toluoylchloride to obtain 21.1 g (76.5% yield) of the captioned compound.

EXAMPLE 21

4-[2-endo-p-toluoyloxy-1-exo-hydroxymethyl-3a,8b-cis-2,3,3a,8b-tetrahydro-1H-5-cyclopenta[b]benzofuranyl] butyric acid methyl ester In 25 ml of anhydrous THF, 1.5 g (0.0049 mol) of 4-[2-endo-hydroxy-1-exo-hydroxymethyl-3a,8b-cis-2,3,3a,8b-tetrahydro-1H-5-cyclopenta[b]benzofuranyl] butyric acid methyl ester and 1.98 g (0.0071 mol) of trityl chloride were dissolved and then 2.0 ml (0.144 mol) of triethylamine was added thereto and the resulting mixture was stirred for 7 hours under refluxing THF. To the thus obtained reaction mixture, 1.36 g (0.00088 mol) of p-toluoylchloride and 0.72 ml (0.0099 mol) of pyridine were added and the resulting mixture was stirred for 5 hours under refluxing THF. The thus obtained reaction mixture was cooled in iced water and 50 ml of methanol and 6 ml (0.026 mol) of 4.4N hydrochloric acid/methanol were added thereto. After stirring the mixture at room temperature for about 1.5 hours, 2.3 g (0.026 mol) of NaHCO$_3$ was added thereto and the resulting mixture was stirred for 30 minutes. The thus obtained reaction mixture was subjected to the same workup procedure and chromatography as in Example 18 to obtain 1.83 g (88.1% yield) of yellow oily product. The thus obtained oily product was recrystallized from ethyl acetate/n-henxane (1:1) to obtain 1.43 g of the captioned compound as white crystals. m. p.: 72.0°-73.0° C.

Elementary Analysis: Calcd. (C$_{25}$H$_{28}$O$_6$) C; 70.74, H; 6.65, Found C; 70.72, H; 6.75.

EXAMPLE 22

4-[2-endo-o-toloyloxy-1-exo-hydroxymethyl-3a,8b-cis-2,3,3a,8b-tetrahydro-1H-5-cyclopenta[b]benzofuranyl] butyric acid methyl ester In 300 ml of anhydrous THF, 49.4 g (0.9 mol) of 4-[2-endo-hydroxy-1-exo-trityloxymethyl-3a,8b-cis-2,3,3a,8b-tetrahydro-1H-5-cyclopenta[b]benzofuranyl] butyric acid methyl ester was dissolved and 25 g (0.162 mol) of p-toluoylchloride and 26.9 ml (0.162 mol) of triethylamine were added thereto, followed by being stirred for 7 hours under refluxing THF. The reaction mixture was was cooled in iced water and 350 ml of methanol and 50 ml (0.44 mol) of 4.4N hydrochloric acid/methanol were added thereto. After stirring the resulting mixture for an hour, 18.4 g of NaHCO$_3$ was added thereto and the resulting mixture was stirred for 30 minutes. The thus obtained reaction mixture was subjected to the same workup procedure and chromatography as in Example 18 to obtain 35 g (91.8% yield) of a yellow oily product. The thus obtained oily product was recrystallized from ethyl acetate/n-henxane (1:1) to obtain 25.9 g of the captioned compound as white crystals.

EXAMPLES 23-27

The same reaction conditions, workup procedure and purification as in Example 21 were repeated except that p-t-butylbenzoylchloride (Example 23), p-phenylbenzoylchloride (Example 24), α-naphthoylchloride (Example 25), β-naphthoylchloride (Example 26) or 3,5-dinitrobenzoylchloride (Example 27) was employed in place of p-toluoylchloride. The results of the reaction and physical properties of the obtained products were shown in Table 1.

TABLE 1

| Example No. | Product | Yield (%)[1] | Melting Point (°C.) | Element Analysis |
|---|---|---|---|---|
| Example 23 | 4-[2-endo-p-t-butylbenzoyloxy-1-exo-hydroxymethyl-3a, 8b-cis-2, 3, 3a, 8b-tetrahydro-1H-5-cyclopenta[b]benzofuranyl] butyric acid methyl ester | 84.5 | | |
| Example 24 | 4-[2-endo-p-phenylbenzoyloxy-1-exo-hydroxymethyl-3a, 8b-cis-2, 3, 3a, 8b-tetrahydro-1H-5-cyclopenta[b]benzofuranyl] butyric acid methyl ester | 93.5 (77.4) | 86.0~87.0 | (C$_{30}$H$_{30}$O$_6$) Calcd. C; 74.06, H; 6.22 Found C; 74.28, H; 6.30 |
| Example 25 | 4-[2-endo-α-naphthoyloxy-1-exo-hydroxymethyl-3a, 8b-cis-2, 3, 3a, 8b-tetrahydro-1H-5-cyclopenta[b] benzofuranyl] butyric acid methyl ester | 95.4 | | |
| Example 26 | 4-[2-endo-β-naphthoyloxy-1-exo-hydroxymethyl-3a, 8b-cis-2, 3, 3a, 8b-tetrahydro-1H-5-cyclopenta[b] benzofuranyl] butyric acid methyl ester | 95.9 (86.9) | 68.5~69.5 | (C$_{28}$H$_{28}$O$_6$) Calcd. C; 73.02, H; 6.13 Found C: 73.03, H; 6.16 |

TABLE 1-continued

| Example No. | Product | Yield (%)[1] | Melting Point (°C.) | Element Analysis |
|---|---|---|---|---|
| Example 27 | 4-[2-endo-3, 5-dinitrobenzoyloxy-1-exo-hydroxymethyl-3a, 8b-cis-2, 3, 3a, 8b-tetrahydro-1H-5-cyclopenta[b]benzofuranyl] butyric acid methyl ester | 84.5 (68.0) | 97.0~98.5 | ($C_{24}H_{24}N_2O_{10}$) Calcd. C; 57.60, H; 4.83, N; 5.60 Found C; 57.56, H; 4.92, N; 5.60 |

[1]The value in ( ) means a yield after recrystallization.

EXAMPLE 28

4-[2-endo-N-phenylcarbamoyloxy-1-exo-hydroxymethyl-3a,8b-cis-2,3,3a,8b-tetrahydro-1H-5cyclopenta[b-]benzofuranyl ] butyric acid methyl ester In 500 ml of anhydrous toluene, 50 g (0.91 mol) of 4-[2-endo-hydroxy-1-exo-trityloxymethyl-3a,8b-cis-2,3,3a,8b-tetrahydro-1H-5-cyclopenta[b]benzofuranyl] butyric acid methyl ester was dissolved and 16 g (0.136 mol) of phenyl isocyanate and 1 ml (0.012 mol) of pyridine were added thereto, followed by being stirred at 60° C. for 4.5 hours. The reaction mixture was cooled in iced water and 500 ml of methanol and 15.2 ml (0.18 mol) of 12N hydrochloric acid were added thereto, followed by being stirred at room temperature for 1.5 hours. The thus obtained reaction mixture was subjected to the same workup procedure and chromatography as in Example 18 to obtain 39.5 g (101.9% yield) of the captioned product. This pale yellow oily product was gradually crystallized at room temparature. The melting point of the thus obtained crystal was 57.0°–59.0° C. Spectrum data of the captioned products obtained in Example 18–28 were summerized in Table 2.

EXAMPLE 29

11,15-didehydroxy-11-acetoxy-16-methyl-15-oxo-18,19-tetradehydro-5,6,7-trinor-4,8-inter-m-phenylene $PGI_2$ methyl ester In 161 ml of anhydrous benzene and 161 ml of anhydrous DMSO, 16.1 g (0.0463 mol) of 4-[2-endo-acetoxy-1-exo-hydroxymethyl-3a,8b-cis-2,3,3a,8b-tetrahydro-1H-5-cyclopenta[b]benzofuranyl] butyric acid methyl ester was dissolved and then 137 ml of anhydrous pyridine and 2.76 ml of trifluoroacetic acid were added thereto and 15.26 g (1.5 eq) of D. C. C (dicyclohexylcarbodiimide) was added thereto, followed by being stirred at 20° C. for 14 hours. The thus obtained reaction mixture was cooled in iced water and 23 g of calcium carbonate was added thereto and the resulting mixture was stirred for 30 minutes. The reaction mixture was filtered and the precipitate was washed 3 times with 20 ml of benzene. The filtrates were combined and washed with 50 ml of water and aqueous layer was extracted with 100 ml of ethyl acetate/cyclohexane (1:1) and with ethyl acetate (100 ml×2, 50 ml). The organic layers were combined and washed with 100 ml of saturated aqueous solution of copper sulfate and then copper sulfate solution was reverse-extracted with 100 ml of ethyl acetate. The organic layers were combined and dried with 120 g of sodium sulfate and concentrated. The thus obtained residue was subjected 4 times to

TABLE 2

| Example No. | IR spectrum Measuring Method | $\nu$ (cm$^{-1}$) | Mass M$^+$ (m/e) | $^1$H-NMR spectrum (CDCl$_3$, 90 MHz) proton shift δ (ppm) |
|---|---|---|---|---|
| Example 18 | neat | 3500, 3064, 2948 2872, 1716, 1599 | 410 | 1.80–1.95(2H, m), 2.25–2.45(3H, m), 2.45–2.65(4H, m), 2.75(1H, s) 3.62(3H, s), 3.65–3.90(3H, m), 5.25–5.47(2H, m), 6.70–7.08(3H, m) 7.20–7.55(5H, m) |
| Example 19 | neat | 3498, 3062, 3024 2948, 2872, 1716 1598, 1577 | 424 424 | 1.80–1.93(2H, m), 2.20–2.68(10H, m), 2.72(1H, s), 3.62(3H, s) 3.65–3.85(3H, m), 5.25–5.40(2H, m) 6.75–7.35(7H, m) |
| Example 20 | neat | 3504, 2948, 2870 1715, 1593 | 424 | 1.80–1.93(2H, m), 2.20–2.70(10H, m), 2.75(1H, s) 3.62(3H, s), 3.70–3.85(3H, m), 5.25–5.45(2H, m), 6.75–7.10(3H, m), 7.12–7.40(4H, m) |
| Example 21 Example 22 | KBr | 3436, 3042, 2926 2864, 1730, 1613 | 424 | 1.80–1.97(2H, m), 2.15–2.65(11H, m), 3.63(3H, s), 3.70–3.85(3H, m) 5.25–5.43(2H, m), 6.75–7.50(7H, m) |
| Example 23 | neat | 3504, 2954, 2870 1737, 1715, 1611 | 466 | 1.30(9H, s), 1.80–1.95(2H, m), 2.20–2.70(8H, m), 3.65(3H, s) 3.70–3.85(3H, m), 5.25–5.45(2H, m), 6.75–7.10(3H, m) 7.25–7.55(4H, m) |
| Example 24 | KBr | 3498, 3022, 2992 2926, 2854, 1717 1706, 1609 | 486 | 1.83–1.97(3H, m), 2.20–2.70(7H, m), 3.60(3H, s), 3.70–3.85(3H, m) 5.25–5.48(2H, m), 6.85–7.15(3H, m), 7.35–7.65(9H, m) |
| Example 25 | neat | 3502, 3050, 2948 2872, 1734, 1712 1622, 1595 | 460 | 1.75–1.90(2H, m), 2.15–2.30(2H, m), 2.35–2.80(8H, m), 3.55(3H, s) 3.65–3.87(3H, m), 5.25–5.55(2H, m), 6.75–8.90(10H, m) |
| Example 26 | KBr | 3486, 3056, 2950 2914, 2866, 1736 1710, 1689, 1632 1596 | 460 | 1.70–1.90(2H, m), 2.15–2.70(8H, m), 3.55(3H, s), 3.70–3.90(3H, m) 5.28–5.52(2H, m), 6.78–7.12(3H, m), 7.45–8.00(7H, m) |
| Example 27 | KBr | 3492, 3116, 3096 2958, 2922, 2874 1724, 1629, 1598 1548 | 500 | 1.60–2.30(5H, m), 2.35–2.75(5H, m), 3.60(3H, s), 3.70–3.90(3H, m) 5.30–5.55(2H, m), 6.75–7.10(3H, m), 8.56(2H, s), 9.10(1H, s) |
| Example 28 | neat | 3334, 3138, 3046 2948, 2872, 1718 1601, 1539 | 425 | 1.85–2.10(2H, m), 2.20–2.85(7H, m), 3.12(1H, s), 3.57–3.80(6H, m) 5.05–5.25(2H, m), 6.70–7.40(9H, m) | azeotropic distillation with 50 ml of benzene and dried by using a vacuum pump. Then 2.76 g of sodium hydride (60% dispersion in mineral oil) was fused to a three-necked flask and dried and the air was substituted to argon. To this flask, 200 ml of anhydrous DME (obtained by distillation over lithium aluminium hydride) was added and the resulting mixture was stirred. In 50 ml of anhydrous DME, 16 g (1.5 eq) of 2-oxo-3-methyl-hept-5-yne-phosphonic acid dimethyl ester was dissolved and this solution was added dropwise to the previously obtained mixture. After stirring the resulting mixture at room temperature for 30 minutes, the previously obtained aldehyde was dissolved in 20 ml of anhydrous DME and this solution was added dropwise thereto and the resulting mixture was stirred at room temperature for 30 minutes. The pH of the thus obtained reaction mixture was adjusted to 7 by adding 1.7 ml of acetic acid. After stiring the mixture for 30 minutes, the resulting precipitate was separated by filtration and the precipitate was washed 5 times with 20 ml of ethyl acetate, followed by concentrating the filtrates to obtain 46 g of an oily product. The thus obtained oily product was purified by column chromatography of silica gel (eluant; ethyl acetate/cyclohexane (1:4)) to obtain 15 g of pure conjugated ketones (yield of 80%).

IR (neat) $\nu$: 1740, 1700, 1670, 1630, 1595 cm$^{-1}$

NMR (CDCl$_3$) $\delta$: 1.20 (3H, d, J=6.3 Hz), 1.78 (3H, t, J=3.1 Hz), 1.60–2.60 (12H), 3.67 (3H, s), 3.68 (2H, m), 5.00 (1H, q, J=6.3 Hz), 5.40 (1H, m), 6.25 (1H, d, J=16.0 Hz), 6.60–7.10 (4H)

Mass (m/e): 452 (M$^+$)

EXAMPLE 30

11,15-didehydroxy-11-acetoxy-16-methyl-15-oxo-18,19-tetradehydro-5,6,7-trinor-4,8-inter-m-phenylene PGI$_2$ methyl ester In 2.5 ml of anhydrous THF and 2.5 ml of anhydrous DMSO (obtained by distillation over calcium hydride), 250 mg (0.721 mmol) of 4-[2-endoacetoxy-1-exo-hydroxymethyl-3a,8b-cis-2,3,3a,8b-tetrahydro-1H-5-cyclopenta[b]benzofuranyl] butyric acid methyl ester was dissolved and then 0.057 ml of anhydrous pyridine (obtained by drying over KOH), 0.042 ml of trifluoro acetic acid (obtained by distillation) and 221 mg of D. C. C (dicyclohexylcarbodiimide) were added thereto, followed by being stirred at room temperature for 14 hours. The reaction mixture was cooled in iced water and 357 mg of calcium carbonate (obtained by drying commercial calcium carbonate at 120° C. for 2 hours) was added thereto and the resulting mixture was stirred for 30 minutes under cooling in iced water.

Then 43 mg (1.5 eq) of sodium hydride (60% dispersion in mineral oil) was fused to two-necked flask, dried and the air was substituted to the argon. To this, 2 ml of anhydrous DME (obtained by distillation over lithium aluminium hydride) was added thereto, followed by being sitrred. In 1.8 ml of anhydrous DME, 250 mg (1.5 eq) of Wordsworth reagent was dissolved and this solution was added dropwise to the previously obtained mixture and the resulting mixture was stirred for 30 minutes at room temperature. To the thus obtained reaction mixture, the supernatant of the previously obtained reaction mixture of aldehyde ester was added using a syringe and the resulting was stirred for 30 minutes. The pH of the reaction mixture was adjusted to 7 by adding two drops of acetic acid using a pipet and the resultant was concentrated. To the residue, 3 ml of water and 10 ml of ethyl acetate were added and the precipitate was filtered and washed twice with 3 ml of ethyl acetate and the filtrates were separated. The aqueous layer was extracted twice with 3 ml of ethyl acetate and the organic layers were combined, washed with 2 ml of water and with 3 ml of saturated aqueous sodium chloride solution, dried over 10 g of sodium sulfate and concentrated to obtain 567 mg of an oily product. The thus obtained oily product was purified by column chromatography (Lober column [B] (silica gel) commercially available from Merck Co., Inc., eluant; ethyl acetate/cyclohexane (1:2)) to obtain 240 mg of the conjugated ketone (yield of 76%).

EXAMPLE 31

11,15-didehydroxy-11-benzoyloxy-16-methyl-15-oxo-18,19-tetradehydro-5,6,7-trinor-4,8-inter-m-phenylene PGI$_2$ methyl ester In 45 ml of anhydrous THF and 17.7 ml (0.25 mol) of anhydrous DMSO, 10.24 g (25 mmol) of 4-[2-endo-benzoyloxy-1-exo-hydroxymethyl-3a,8b-cis-2,3,3a,8b-tetrahydro-1H-5-cyclopenta[b]benzofuranyl] butyric acid methy ester and 6.19 g (30 mmol) of dicyclohexylcarbodiimide were dissolved and then 0.4 ml (5 mmol) of pyridine and 0.37 ml (5 mmol) of trifluoro acetic acid were added thereto under nitrogen atmosphere, followed by being stirred at room temperature for 1.5 hours to obtain an aldehyde. Then 1.5 g of sodium hydride (37.5 mmol) (60% dispersion in mimeral oil) was suspended in 50 ml of anhydrous THF and this suspension was cooled in iced water. To this suspension, 8.78 g (37.5 mmol) of 2-oxo-hept-5-yne-phosphonic acid dimethyl ester in 25 ml of anhydrous THF was added and the resulting mixture was stirred for 30 minutes at room temperature under nitrogen atmosphere. The thus obtained reaction mixture was cooled down to $-10°$–$-20°$ C. and the previously obtained reaction mixture of aldehyde ester was added thereto and the resulting mixture was stirred for 30 minutes. To the reaction mixture, 2.2 ml of acetic acid was added to neutralized the same. The thus obtained reaction mixture was filtered through Hyflo Super-Cel and 100 ml of ethyl acetate and 50 ml of water were added to the filtrate and the resulting mixture was separated. The organic layer was washed 3 times with 50 ml of 10% saline and dried over anhydrous magnesium sulfate. After removing magnesium sulfate by filtration, the filtrate was concentrated under reduced pressure and 20.8 g of the thus obtained concentrate was purified by column chromatography of silica gel (Art 7734, 400 g, commercially available from Merck Co., Inc., eluant; ethyl acetate/cyclohexane (1:5)) to obtain 10.82 g (yield of 84.3%) of the captioned compound.

EXAMPLES 32–40

The same reaction conditions, workup procedure and purification as in Example 31 were repeated except that 4-[2-endo-o-toluoyloxy-1-exo-hydroxymethyl-3a,8b-cis-2,3,3a,8b-tetrahydro-1H-5-cyclopenta[b]benzofuranyl] butyric acid methyl ester (Example 32), 4-[2-endo-m-toluoyloxy-1-exo-hydroxymethyl-3a,8b-cis-2,3,3a,8b-tetrahydro-1H-5-cyclopenta[b]benzofuranyl] butyric acid methyl ester (Example 33), 4-[2-endo-p-toluoyloxy-1-exo-hydroxymethyl-3a,8b-cis-2,3,3a,8b-tetrahydro-1H-5cyclopenta[b]benzofuranyl] butyric acid methyl ester (Example 34), 4-[2-endo-p-t-butylbenzoyloxy-1-exo-hydroxymethyl-3a,8b-cis-2,3,3a,8b-tetrahydro-1H-5-cyclopenta[b]benzofuranyl] butyric acid methyl ester (Example 35), 4-[2-endo-p-phenylbenzoyloxy-1-exo-hydroxymethyl-3a,8b-cis-2,3,3a,8b-tetrahydro-1H-5-cyclopenta[b]benzofuranyl] butyric acid methyl ester (Example 36), 4-[2-endo-α-naphthoyloxy-1-exo-hydroxymethyl-3a,8b-cis-2,3,3a,8b-tetrahydro-1H-5-cyclopenta[b]benzofuranyl] butyric acid methyl ester (Example 37), 4-[2-endo-β-naphthoyloxy-1-exo-hydroxymethyl-3a,8b-cis-2,3,3a,8b-tetrahydro-1H-5cyclopenta[b]benzofuranyl] butyric acid methyl ester (Example 38), 4-[2-endo-3,5-dinitrobenzoyloxy-1-exo-clopenta[b]benzofuranyl] butyric acid methyl ester (Example 39) or 4-[2-endo-N-phenylcarbamoyloxy-1-exo-hydroxymethyl-3a,8b-cis-2,3,3a,8b-tetrahydro-1H-5-cyclopenta[b]benzofuranyl] butyric acid methyl ester (Example 40) was employed in place of 4-[2-endo-benzoyloxy-1-exo-hydroxymethyl-3a,8b-cis-2,3,3a,8b-tetrahydro-1H-5-cyclopenta[b]benzofuranyl] butyric acid methyl ester. The results of the reactions are summarized in Table 3. The spectrum data of the same are shown in Table 4.

TABLE 3

| Example No. | Product | Yield (%)[1] | Melting Point (°C.) | Element Analysis |
|---|---|---|---|---|
| Example 32 | 11, 15-didehydroxy-11-o-toluoyloxy-16-methyl-15-oxo-18, 19-tetradehydro-5, 6, 7-trinor-4,8-inter-m-phenylene PGI$_2$ methyl ester | 87.9 | | |
| Example 33 | 11, 15-didehydroxy-11-m-toluoyloxy-16-methyl-15-oxo-18, 19-tetradehydro-5, 6, 7-trinor-4, 8-inter-m-phenylene PGI$_2$ methyl ester | 97.5 | | |
| Example 34 | 11, 15-didehydroxy-11-p-toluoyloxy-16-methyl-15-oxo-18, 19-tetradehydro-5, 6, 7-trinor-4, 8-inter-m-phenylene PGI$_2$ methyl ester | 91.7 (70.8) | 74.0~75.0 | (C$_{33}$H$_{36}$O$_6$) Calcd.  C; 74.97, H; 6.86 Found  C; 74:87, H; 6.89 |
| Example 35 | 11, 15-didehydroxy-11-p-t-butylbenzoyloxy-16-methyl-15-oxo-18, 19-tetradehydro-5, 6, 7-trinor-4, 8-inter-m-phenylene PGI$_2$ methyl ester | 87.8 | | |
| Example 36 | 11, 15-didehydroxy-11-p-phenylbenzoyloxy-16-methyl-15-oxo-18, 19-tetradehydro-5, 6, 7-trinor-4, 8-inter-m-phenylene PGI$_2$ methyl ester | 87.3 | | |
| Example 37 | 11, 15-didehydroxy-11-α-naphthoyloxy-16-methyl-15-oxo-18, 19-tetradehydro-5, 6, 7-trinor-4, 8-inter-m-phenylene PGI$_2$ methyl ester | 103.3 | | |
| Example 38 | 11, 15-didehydroxy-11-β-naphthoyloxy-16-methyl-15-oxo-18, 19-tetradehydro-5, 6, 7-trinor-4, 8-inter-m-phenylene PGI$_2$ methyl ester | 98.0 (63.4) | 72.5~73.5 | (C$_{36}$H$_{36}$O$_6$) Calcd.  C; 76.57, H; 6.43 Found  C; 76.44, H; 6.51 |
| Example 39 | 11, 15-didehydroxy-11-3, 5-dinitrobenzoyloxy-16-methyl-15-oxo-18, 19-tetradehydro-5, 6, 7-trinor-4, 8-inter-m-phenylene PGI$_2$ methyl ester | 97.5 | | |
| Example 40 | 11, 15-didehydroxy-11-N-phenylcarbamoyloxy-16-methyl-15-oxo-18, 19-tetradehydro-5, 6, 7-trinor-4, 8-inter-m-phenylene PGI$_2$ methyl ester | 88.0 | 87.5~88.5 | |

[1]The value in ( ) means a yield after recrystallization.

hydroxymethyl-3a,8b-cis-2,3,3a,8b-tetrahydro-1H-5cy-

TABLE 4

| | | Spectrum Data | | |
|---|---|---|---|---|
| Example No. | IR spectrum Measuring Method | ν (cm$^{-1}$) | Mass M$^+$ (m/e) | $^1$H-NMR spectrum (CDCl$_3$, 270 MHz) proton shift δ (ppm) |
| Example 31 | neat | 2950, 1720, 1672 1600, 983 | 514 | 1.20(3H, d), 1.70-1.95(5H, m), 2.20-2.73(8H, m), 2.85-3.00(1H, m) 3.15-3.25(1H, m), 3.65(3H, s), 3.85-3.95(1H, m), 5.30-5.45(2H, m) 6.30-6.42(1H, m), 6.75-7.55(9H, m) |
| Example 32 | neat | 3024, 2950, 2930 1720, 1673, 1627 1600, 982 | 528 | 1.20(3H, d), 1.70-1.95(5H, m), 2.20-2.75(11H, m), 2.85-3.02(1H, m) 3.10-3.22(1H, m), 3.65(3H, s), 3.80-3.90(1H, m), 5.30-5.42(2H, m) 6.30-6.42(1H, m), 6.75-7.38(8H, m) |
| Example 33 | neat | 2950, 1718, 1673 1627, 1594, 982 | 528 | 1.21(3H, d), 1.65-1.95(5H, m), 2.15-2.75(11H, m), 2.82-3.00(1H, m) 3.15-3.25(1H, m), 3.63(3H, s), 3.82-3.92(1H, m), 5.30-5.40(2H, m) 6.30-6.42(1H, m), 6.75-7.40(8H, m) |
| Example 34 | KBr | 2920, 1724, 1690 1631, 991 | 528 | 1.20(3H, d), 1.70-1.95(5H, m), 2.15-2.75(11H, m), 2.80-3.00(1H, m) 3.15-3.25(1H, m), 3.63(3H, s), 3.80-3.90(1H, m), 5.30-5.40(2H, m) 6.25-6.40(1H, m), 6.75-7.45(8H, m) |
| Example 35 | neat | 2964, 2870, 1718 1673, 1627, 1612 | 570 | 1.20(3H, d), 1.32(9H, s), 1.70-1.95(5H, m), 2.20-2.75(8H, m), 2.85-3.00(1H, m), 3.15-3.25(1H, m), 3.63(3H, s), 3.82-3.92(1H, m) |

TABLE 4-continued

| Example No. | IR spectrum Measuring Method | ν (cm⁻¹) | Mass M⁺ (m/e) | ¹H-NMR spectrum (CDCl₃, 270 MHz) proton shift δ (ppm) |
|---|---|---|---|---|
| | | 982 | | 5.30–5.40(2H, m), 6.30–6.42(1H, m), 6.78–7.50(8H, m) |
| Example 36 | neat | 3030, 2932, 2856 | 590 | 1.20(3H, d), 1.70–1.97(5H, m), 2.20–2.75(8H, m), 2.85–3.05(1H, m) |
| | | 1716, 1673, 1627 | | 3.20–3.30(1H, m), 3.63(1H, s), 3.85–3.95(1H, m), 5.30–5.45(2H, m) |
| | | 1611, 1564, 982 | | 6.32–6.45(1H, m), 6.78–7.10(4H, m), 7.35–7.65(9H, m) |
| Example 37 | neat | 3050, 2950, 1735 | 564 | 1.23(3H, d), 1.65–1.95(5H, m), 2.15–2.35(3H, m), 2.35–2.80(5H, m) |
| | | 1714, 1673, 1627 | | 2.85–3.00(1H, m), 3.20–3.35(1H, m), 3.58(3H, s), 3.85–3.95(1H, m) |
| | | 1595, 1577, 1510 | | 5.30–5.50(2H, m), 6.35–6.45(1H, m), 6.75–7.08(4H, m) |
| | | 982 | | 7.10–8.90(7H, m) |
| Example 38 | KBr | 3058, 2938, 1723 | 564 | 1.20(3H, d), 1.70–1.90(5H, m), 2.15–2.35(3H, m), 2.35–2.75(5H, m) |
| | | 1687, 1629, 1599 | | 2.82–3.00(1H, m), 3.22–3.35(1H, m), 3.55(3H, s), 3.90–3.98(1H, m) |
| | | 983 | | 5.30–5.45(2H, m), 6.30–6.45(1H, m), 6.80–7.10(4H, m) |
| | | | | 7.45–7.95(7H, m) |
| Example 39 | neat | 3098, 2952, 1732 | 604 | 1.23(3H, d), 1.60–1.85(5H, m), 2.15–2.35(3H, m), 2.35–2.75(5H, m) |
| | | 1698, 1673, 1628 | | 2.85–3.00(1H, m), 3.32–3.42(1H, m), 3.63(3H, s), 3.95–4.05(1H, m) |
| | | 1597, 1545, 983 | | 5.35–5.50(2H, m), 6.35–6.48(1H, m), 6.75–7.10(4H, m) |
| | | | | 8.60(2H, s), 9.13(1H, s) |
| Example 40 | KBr | 3330, 3054, 2944 | 529 | |
| | | 1737, 1704, 1629 | | |
| | | 1601, 1538, 988 | | |

EXAMPLE 41

11,15-didehydroxy-11-acetoxy-15-oxo-18,19-tetradehydro-5,6,7-trinor-4,8-inter-m-phenylene PGI₂ methyl ester In 0.3 ml of anhydrous pyridine in 10 ml of anhydrous benzene, 150 ml of 4-[2-endo-acetoxy-1-exo-hydroxymethyl-3a,8b-cis-2,2,3a,8b-tetrahydro-1H-5cyclopenta[b]benzofuranyl] butyric acid methyl ester was dissolved. And then 0.14 ml of trifluoro acetic acid was dissolved in 10 ml of anhydrous DMSO and 0.37 ml of this solution was added to the previously obtained solution. Then 340 mg of D. C. C (dicyclohexylcarbodiimide) was added the solution and the resulting mixture was stirred at room temperature for 14 hours. The precipitate was separated by filtration and the filtrate was concentrated to obtain 260 mg of clude aldehyde. Then 118 mg of sodium hydride (55% dispersion in mineral oil) was suspended in 10 ml of DME. To this suspension, 689 mg of 2-oxo-hept-5-yne-phosphonic acid dimethyl ester in 10 ml of DME was added and the resulting mixture was stirred for 30 minutes at room temperature under argon atmosphere. To the thus obtained reaction mixture, 260 mg of the previously obtained aldehyde in 5 ml of DME was added and the resulting mixture was stirred for 30 minutes at room temperature. To the reaction mixture, acetic acid was added to attain pH 7 and the resultant was concentrated. To the residue, 10 ml of pentane/ether (1:1) was added and the precipitate was separated by filtration and the filtrate was concentrated to obtain 800 mg of an oily product. The thus obtained oily product was purified by column chromatography (Lober column (silica gel) commercially available from Merck Co., Inc., eluant; ethyl acetate:cyclohexane=1:3) to obtain 116 mg of the captioned compound (yield of 62%).

IR (neat) ν: 1740, 1700, 1675, 1630, 1575, 750 cm⁻¹

NMR (CDCl₃) δ: 1.69 (3H, t, J=3.1 Hz), 1.71 (3H, s), 1.70–3.05 (13H), 3.60 (3H, s), 3.62 (1H, m), 4.90 (1H, q, J=6.2 Hz), 5.15 (1H, m), 6.15 (1H, dd, J=16.0 Hz, 2.0 Hz), 6.50–7.10 (4H, m)

Mass (m/e): 438 (M⁺)

EXAMPLE 42

11-dehydroxy-11-acetoxy-18,19-tetradehydro-5,6,7-trinor-4,8-inter-m-phenylene PGI₂ methyl ester In 10 ml of methanol, 116 mg of 11,15-didehydroxy-11-acetoxy-15-oxo-18,19-tetradehydro-5,6,7-trinor-4,8-inter-m-phenylene PGI₂ methyl ester was dissolved and then 150 mg of cerium chloride heptahydrate was dissolved therein and under colling in iced water, 15 mg of sodium borohydride was added, followed by being stirred for 15 minutes. To the reaction mixture, 2 ml of saturated aqueous sodium hydrogen carbonate solution was added and the resulting mixture was stirred for 10 minutes and concentrated. To the residue, 5 ml of ethyl acetate was added and the resultant was filtered through Hyflo Super-Cel (2 g) with suction and washed twice with 5 ml of ethyl acetate. The filtrates were combined, washed with 2 ml of water and aqueous layer was extracted with 2 ml of ethyl acetate. The organic layers were combined, washed with 2 ml of water and with 2 ml of saturated aqueous sodium chloride solution, dried and concentrated to obtain 170 mg of an oily product. The thus obtained oily product was employed in the next reaction without purification.

EXAMPLE 42-2

18,19-tetradehydro-5,6,7-trinor-4,8-inter-m-phenylene PGI₂ methyl ester

In 4.5 ml of anhydrous methanol, 170 mg of 11-dehydroxy-11-acetoxy-18,19-tetradehydro-5,6,7-trinor-4,8-inter-m-phenylene PGI₂ methyl ester was dissolved and 3 drops of 4.8M sodium methoxide was added thereto using a syringe and the resulting mixture was stirred for 2.5 hours at room temperature. To the thus obtained reaction mixture, 1 g of ion exchange resin (IRC-50) was added and the resultant was stirred for 20 minutes at room temperature and filtered. The resin was washed sufficiently with methanol and the filtrates were combined and concentrated to obtain 170 mg of an oily product. The thus obtained oily product was purified by column chromatography (Lober column (silica gel) commercially available from Merck Co., Inc., eluant; ethyl acetate:cyclohexane=3:1) to obtain 49 mg of the diol (yield of 47%).

IR (neat) ν: 3370, 1740, 1595, 970, 745 cm⁻¹

NMR (CDCl$_3$) δ: 1.70 (3H, t, J=3.0 Hz), 1.20–2.80 (15H), 3.40 (1H, t, J=7.8 Hz), 3.59 (3H, s), 3.80 (1H, q, J=6.1 Hz), 4.50 (1H, m), 5.05 (1H, m), 5.60 (2H, m), 6.60–7.00 (3H)

Mass (m/e): 398 (M+)

EXAMPLE 43

18,19-tetradehydro-5,6,7-trinor-4,8-inter-m-phenylene PGI$_2$

In 4.3 ml of methanol, 43 mg of 18,19-tetradehydro-5,6,7-trinor-4,8-inter-m-phenylene PGI$_2$ methyl ester was dissolved and then 1 ml of 1N aqueous sodium hydroxide solution was added thereto and the resulting mixture was stand for 14 hours at room temperature under argon atmosphere. The thus obtained reaction mixture was concentrated and under cooling in iced water, 1 ml of 1N hydrochloric aicd was added to the residue to attain pH 3. The resultant was extracted 3 times with 5 ml of ethyl acetate and organic layers were combined, washed with 2 ml of water and with 2 ml of saturated aqueous sodium chloride solution, dried and concentrated to obtain 41 mg of carbonic acid (yield of 93%).

IR (neat) ν: 3700–2200, 1710, 1595, 975, 740 cm$^{-1}$

NMR (CDCl$_3$) δ: 1.65 (3H, t, J=3.0 Hz), 1.40–2 80 (14H), 3.30 (1H, t, J=8.0 Hz), 3.80 (1H, m), 4.20 (1H, m), 5.00 (1H, m), 5.10–5.80 (4H), 6.50–7.00 (3H)

Mass (m/e): 384 (M+)

EXAMPLE 44

11-dehydroxy-11-acetoxy-16-methyl-18,19-tetradehydro-5,6,7-trinor-4,8-inter-m-phenylene PGI$_2$ methyl ester In 10 ml of methanol, 122 mg of 11,15-didehydroxy-11-acetoxy-16-methyl-15-oxo-18,19-tetradehydro-5,6,7-trinor-4,8-inter-m-phenylene PGI2 methyl ester was dissolved and then 150 mg of cerium chloride heptahydrate was added thereto and under colling in iced water, 15 mg of sodium borohydride was added, followed by being stirred for 10 minutes. To the reaction mixture, 2 ml of saturated aqueous sodium hydrogen carbonate solution was added and the resulting mixture was stirred for 10 minutes. After concentrating the reaction mixture, to the residue, 5 ml of ethyl acetate was added and the resultant was filtered and the precipitate was washed twice with 2 ml of ethyl acetate. The organic layers were combined, washed with water and saturated aqueous sodium chloride solution, dried and concentrated to obtain 130 mg of an oily product. The thus obtained oily product was purified by column chromatograogy (Lober column (silica gel) commercially available from Merck Co., Inc., eluant; ethyl acetate:cyclohexane=1:2) to obtain 54 mg of pure captioned compound (yield of 44%).

IR (neat) ν: 3475, 1740, 1595, 970 cm$^{-1}$

Mass (m/e): 454 (M+)

EXAMPLE 45

16-methyl-18,19-tetradehydro-5,6,7-trinor-4,8-inter-m-phenylene PGI$_2$ methyl ester In 4.5 ml of anhydrous methanol, 54 mg of 11-dehydroxy-11-acetoxy-16-methyl-18,19-tetradehydro-5,6,7-trinor-4,8-inter-m-phenylene PGI$_2$ methyl ester was dissolved and then 0.001 ml of 4.8N sodium methoxide was added thereto and the resulting mixture wa stirred for 1.5 hours at room temperature. To the reaction mixture, acetic acid was added and the resulting mixture was concentrated. The residue was dissolved in 20 ml of ethyl acetate, washed with saturated aqueous sodium hydrogen carbonate solution, water and saturated aqueous sodium chloride solution, dried and concentrated to obtain 55 mg of an oily product. The thus obtained oily product was purified by column chromatography (Lober column type B (silica gel) commercially available from Merck Co., Inc., eluant; ethyl acetate:cyclohexane=3:1) to obtain 48 mg of the diol (yield of 98%).

IR (neat) ν: 3370, 1740, 1595, 970, 745 cm$^{-1}$

NMR (CDCl$_3$) δ: 1.00 (3H, d, J=6.3 Hz), 1.80 (3H, t, J=3.1 Hz), 1.80–2.80 (14H), 3.45 (1H, t, J=7.8 Hz), 3.65 (3H, s), 4.00 (2H, m), 5.10 (1H, m), 5.65 (2H, m), 6.60–7.00 (3H)

Mass (m/e): 412 (M+)

EXAMPLE 46

16-methyl-18,19-tetradehydro-5,6,7-trinor-4,8-inter-m-phenylene PGI$_2$

In 4.3 ml of methanol, 41 mg of 16-methyl-18,19-tetradehydro-5,6,7-trinor-4,8-inter-m-phenylene PGI$_2$ methyl ester was dissolved and then 1 ml of 1N aqueous sodium hydroxide solution was added thereto and the resulting mixture was stand for 17 hours at 30° C. The thus obtained reaction mixture was concentrated and 1 ml of water was added to the residue. The pH of the resultant was adjusted to 4 by adding 1N hydrochloric acid and the resultant was extracted 3 times with 5 ml of ethyl acetate. The organic layers were combined, washed with 5 ml of water and with 5 ml of saturated aqueous sodium chloride solution, dried and concentrated to obtain 39 mg of pure carboxylic acid (yield of 100%).

IR (neat) ν: 3700–2200, 1710, 1595, 743 cm$^{-1}$

NMR (CDCl$_3$) δ: 1.00 (3H, m), 1.79 (3H, s), 1.50–3.00 (12H), 3.35 (1H, t, J=9.1 Hz), 4.00 (2H, m), 5.20 (4H, m), 5.60 (2H, m), 6.80 (1H, m), 6.90 (2H, m)

Mass (m/e): 398 (M+)

EXAMPLE 47

16-methyl-18,19-tetradehydro-5,6,7-trinor-4,8-inter-m-phenylene PGI$_2$ methyl ester In 60 ml of methanol and 20 ml of THF, 6.00 g (11.35 mmol) of 11,15-didehydroxy-11-p-toluoyloxy-16-methyl-15-oxo-18, 19-tetradehydro-5,6,7-trinor-4,8-inter-m-phenylene PGI$_2$ methyl ester (in the form of crystals) and 3.72 g (11.35 mmol) of cerium trichloride heptahydrate were dissolved and this solution was cooled down to −10° C. and then 322 mg (8.5 mmol) of sodium borohydride was added thereto for 30 minutes under stirring. After stirring the mixture for another 20 minutes, 10 ml of saturated aqueous sodium hydrogen carbonate solution was added thereto and the resulting mixture was stirred for 15 minutes. The precipitate was removed by filtlation through Hyflo Super-Cel and the filtrate was concentrated. To the residue, 50 ml of ethyl acetate and a little amount of magnesium sulfate were added and the resultant was stirred for 10 minutes, filtrate and concentrated to obtain 7.05 g of an oily product. The thus obtained oily product was recrystallized from 12 ml of ethyl acetate/cylohexane (1:2) to obtain 0.55 g of crystals and 6.0 g of solid from concentrated mother liquid. In 50 ml of methanol, 6.0 g of the solid from concentrated mother liquid was dissolved and 1.1 ml (5.5 mmol) of 5N sodium methoxide was added thereto and the resulting mixture was stirred for 20 hours at room temperature. To the reaction mixture, 0.3 ml of acetic acid was added and the resulting mixture was concentrated. To the residue, 50 ml of ethyl acetate and a little amount of magnesium sulfate were added and the resultant was stirred for 10 minutes, filtered and concentrated to obtain 5.8 g of an oily product. The thus obtained oily product was purified by column chromatography of silica gel (silica gel; Art 13905 (180 g), eluant; ethyl acetate:cyclohexane=3:2) to obtain 3.15 g of colorless oily product (yield of 67.3%). The obtained procuct was shown the same spectrum data as that of the captioned compound obtained in Example 45.

The same procedure as in Example 47 except that 11,15-didehydroxy-11-benzoyloxy-16-methyl-15-oxo-18,19-tetradehydro-5,6,7-trinor-4,8-inter-m-phenylene PGI$_2$ methyl ester, 11,15-didehydroxy-11-o-toluoyloxy-16-methyl-15-oxo-18,19-tetradehydro-5,6,7-trinor-4,8-inter-m-phenylene PGI$_2$ methyl ester, 11,15-didehydroxy-11-m-toluoyloxy-16-methyl-15-oxo-18,19-tetradehydro-5,6,7-trinor-4,8-inter-m-phenylene PGI$_2$ methyl ester, 11,15-didehydroxy-11-p-t-butylbenzoyloxy-16-methyl-15-oxo-18,19-tetradehydro-5,6,7-trinor-4,8-inter-m-phenylene PGI$_2$ methyl ester, 11,15-didehydroxy-11-p-phenylbenzoyloxy-16-methyl-15-oxo-18,19-tetradehydro-5,6,7-trinor-4,8-inter-m-phenylene PGI$_2$ methyl ester, 11,15-didehydroxy-11-α-naphthoyloxy-16-methyl-15-oxo-18,19-tetradehydro-5,6,7-trinor-4,8-inter-m-phenylene PGI$_2$ methyl ester, 11,15-didehydroxy-11-β-naphthoyloxy-16-methyl-15-oxo-18,19-tetradehydro-5,6,7-trinor-4,8-inter-m-phenylene PGI$_2$ methyl ester or 11,15-didehydroxy-11-(3,5-dinitrobenzoyloxy)-16-methyl-15-oxo-18,19-tetradehydro-5,6,7-trinor-4,8-inter-m-phenylene PGI$_2$ methyl ester is employed in place of 11,15-didehydroxy-11-p-toluoyloxy-16-methyl-15-oxo-18,19-tetradehydro-5,6,7-trinor-4,8-inter-m-phenylene PGI$_2$ methyl ester also yields the captioned cpmpound.

EXAMPLE 48

11,15-didehydroxy-11-acetoxy-16-methyl-20-homo-15-oxo-18,19-tetradehydro-5,6,7-trinor-4,8-inter-m-phenylene PGI$_2$ methyl ester The same procedure as in Example 41 was repeated except that 3-methyl-2-oxo-oct-5-yne-phosphonic acid dimethyl ester was employed in place of 3-methyl-2-oxo-hept-5-yne-phosphonic acid dimethyl ester to obtain 120 mg of the captioned compound from 150 mg of 4-[2-endo-acetoxy-1-exo-hydroxymethyl-3a,8b-cis-2,3,3a,8b-tetrahydro-1H-5-cyclopenta[b]benzofuranyl] butyric acid methyl ester as a starting material.

IR (neat) $v$: 1740, 1700, 1670, 1630, 1595, 970 cm$^{-1}$
Mass (m/e): 466 (M$^+$)

EXAMPLE 49

16-methyl-20-homo-18,19-tetradehydro-5,6,7-trinor-4,8-inter-m-phenylene PGI$_2$ methyl ester The same procedure as in Example 45 was repeated except that 58 mg of 11-dehydroxy-11-acetoxy-16-methyl-20-homo-18,19-tetradehydro-5,6,7-trinor-4,8-inter-m-phenylene PGI$_2$ methyl ester was employed as a starting material to obtain 50 mg of the captioned compound.

IR (neat) $v$: 3370 1740 1595 970 cm$^{-1}$
Mass (m/e): 426 (M$^+$)

EXAMPLE 50

16-methyl-20-homo-18,19-tetradehydro-5,6,7-trinor-4,8-inter-m-phenylene PGI$_2$

The same procedure as in Example 46 was repeated except that 50 mg of 16-methyl-20-homo-18,19-tetradehydro-5,6,7-trinor-4,8-inter-m-phenylene PGI$_2$ methyl ester was employed as a starting material to obtain 48 mg of the captioned compound.

IR (neat) $v$: 3700–2200, 1710, 1595, 975 cm$^{-1}$
Mass (m/e): 412 (M$^+$)

EXAMPLE 51

16-methyl-5,6,7-trinor-18,18,19,19-tetradehydro-4,8-inter-m-phenylene PGI$_2$ methyl ester (1)

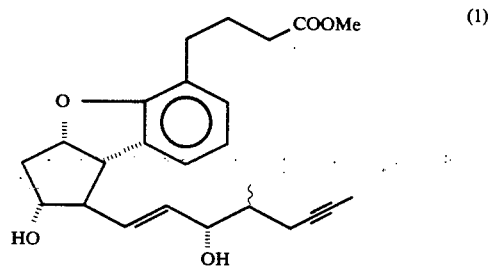

In 3 ml of anhydrous THF, 328 mg (0.619 mmol) of 15-epi-11-dehydroxy-(p-toluoyloxy)-16-methyl-5,6,7-trinor-18,19-tetradehydro-4,8-inter-m-phenylene PGI$_2$ methyl ester was dissolved and then 333 mg (1.27 mmol) of triphenylphosphine and 158 mg (1.29 mmol) of benzoic acid were added thereto, followed by being stirred at room temperature. To the thus obtained reaction mixture, 284 mg (1.29 mmol) of diethylazodicarboxylate in 6 ml of anhydrous THF was added for 5 minutes and the resulting mixture was stirred for 2 hours at room temperature. The solvent was evaporated under reduced pressure and the residue was dissolved in 10 ml of methanol and 1 g of potassium carbonate was added thereto, followed by being stirred at room temperature for 16 hours. The solvent was evaporated under reduced pressure and the residue was dissolved in 10 ml of ethyl acetate and washed with water to neulralize the same. The resultant was dried over anhydrous sodium sulfate and the solvent was evaporated under reduced pressure and the thus obtained residue was purified by Lober column, commercially available from Merck Co., Inc. (eluant; ethyl acetate:cyclohexane=1:2) to obtain 216 mg of the captioned compound.

IR (neat) $v$: 3370, 2985, 2950, 2930, 1720, 1595, 1455, 1415, 1380, 1360, 1340, 1305, 1285, 1250, 1180, 1130, 1100, 1080, 1025, 1010, 960, 900, 860 cm NMR (CDCl$_3$, δ): 1.00 (3H, two, d, J=6.3 Hz), 1.80 (3H, t, J=3.1 Hz), 1.80–2.80 (14H, m), 3.45 (1H, t, J=7.8 Hz), 3.65 (3H, s), 4.05–4.30 (2H, m), 5.05–5.13 (1H, m), 5.58–5.68 (2H, m), 6.60–7.00 (3H, m)

Mass (EI method, m/e): 412 (M$^+$)

High resolution mass spectrum Calcd. (C$_{25}$H$_{325}$, M$^+$): 412.2250 Found (M$^+$): 412.2258

The same procedure as in Example 51 except that 15-ep-11-dehydroxy-11-acetoxy-16-methyl-5,6,7-trinor-18,19-tetradehydro-4,8-inter-m-phenylene PGI$_2$ methyl ester, 15-epi-11-dehydroxy-11-propionyloxy-16-methyl-5,6,7-trinor-18,19-tetradehydro-4,8-inter-m-phenylene PGI$_2$ methyl ester, 15-epi-11-dehydroxy-11-butyroyloxy-16-methyl-5,6,7-trinor-18,19-tetradehydro-4,8-inter-m-phenylene PGI₂ methyl ester, 15-epi-11-dehydroxy-11-octanoloxy-16-methyl-5,6,7-trinor-18,19-m-phenylene PGI₂ methyl ester, 15-epi-11-dehydroxy-11-decanoloxy-16-methyl-5,6,7-trinor-18,19-tetradehydro-4,8-inter-m-phenylene PGI₂ methyl ester, 15-epi-11-dehydroxy-11-valeroxy-16-methyl-5,6,7trinor-18,19-tetradehydro-4,8-inter-m-phenylene PGI₂ methyl ester, 15-epi-11-dehydroxy-11-benzoyloxy-16-methyl-5,6,7-trinor-18,19-tetradehydro-4,8-inter-m-phenylene PGI₂ methyl ester,15-epi-11-dehydroxy-11-(α-naphthoyloxy)-16-methyl-5,6,7-trinor-18,19-tetradehydro-4,8-inter-m-phenylene PGI₂ methyl ester, 15-epi-11-dehydroxy-11-(β-naphthoyloxy)-16-methyl-5,6,7-trinor-18,19-tetradehydro-4,8-inter-m-phenylene PGI₂ methyl ester, 15-epi-11-dehydroxy-11-(m-toluoyloxy)-16-methyl-5,6,7-trinor-18,19-tetradehydro-4,8-inter-m-phenylene PGI₂ methyl ester, 15-epi-11-dehydroxy-11-(o-toluoyloxy)-16-methyl-5,6,7-trinor-18,19-tetradehydro-4,8-inter-m-phenylene PGI₂ methyl ester or 15-epi-11-dehydroxy-11-(p-phenylbenzoyloxy)-16-methyl-5,6,7-trinor-18,19-tetradehydro-4,8-inter-m-phenylene PGI₂ methyl ester is employed in place of 15-epi-11-dehydroxy-11-(p-toluoyloxy)-16-methyl-5,6,7-trinor-18,19-tetradehydro-4,8-inter-m-phenylene PGI₂ methyl ester also yields the captioned compound.

The same procedure as in Example 51 except that ethanol is employed in place of methanol as a solvent, and except that 15-epi-11-dehydroxy-11-acetoxy-16-methyl-5,6,7-trinor-18,19-tetradehydro-4,8-inter-m-phenylene PGI₂ ethyl ester, 15-epi-11-dehydroxy-11-propionyloxy-16-methyl-5,6,7-trinor-18,19-tetradehydro-4,8-inter-m-phenylene PGI₂ ethyl ester, 15-epi-11-dehydroxy-11-butyroyloxy-16-methyl-5,6,7-trinor-18,19-tetradehydro-4,8-inter-m-phenylene PGI₂ ethyl ester, 15-epi- 11-dehydroxy-11-octanoyloxy-16-methyl-5,6,7-trinor-18,19-tetradehydro-4,8-inter-m-phenylene PGI₂ ethyl ester, 15-epi-11-dehydroxy-11-decanoyloxy-16-methyl-5,6,7-trinor-18,19-tetradehydro-4,8-inter-m-phenylene PGI₂ ethyl ester, 15-epi-11-dehydroxy-11-valeroyloxy-16-methyl-5,6,7-trinor-18,19-tetradehydro-4,8-inter-m-phenylene PGI₂ ethyl ester, 15-epi-11-dehydroxy-11-benzoyloxy-16-methyl-5,6,7-trinor-18,19-tetradehydro-4,8-inter-m-phenylene PGI₂ ethyl ester, 15-epi-11-dehydroxy-11-(α-naphthoyloxy)-16-methyl-5,6,7-trinor-18,19-tetradehydro-4,8-inter-m-phenylene PGI₂ ethyl ester, 15-epi-11-dehydroxy-11-(β-naphthoyloxy)-16-methyl-5,6,7-trinor-18,19-tetradehydro-4,8-inter-m-phenylene PGI₂ ethyl ester, 15-epi-11-dehydroxy-11-(m-toluoyloxy)-16-methyl-5,6,7-trinor-18,19-tetradehydro-4,8-inter-m-phenylene PGI₂ ethyl ester, 15-epi-11-dehydroxy-11-(o-toluoyloxy)-16-methyl-5,6,7-trinor-18,19-tetradehydro-4,8-inter-m-phenylene PGI₂ ethyl ester or 15-epi-11-dehydroxy-11-(p-phenylbenzoyloxy)-16-methyl-5,6,7-trinor-18,19-tetradehydro-4,8-inter-m-phenylene PGI₂ ethyl ester is employed in place of 15-epi-11-dehydroxy-11-(p-toluoyloxy)-16-methyl-5,6,7-trinor-18,19-tetradehydro-4,8-inter-m-phenylene PGI₂ methyl ester yields 16-methyl-5,6,7-trinor-18,19-tetradehydro-4,8-inter-m-phenylene PGI₂ ethyl ester.

EXAMPLE 52

16-methyl-2,5,6,7-tetranor-18,19-tetradehydro-4,8-inter-m-phenylene PGI₂ methyl ester (2)

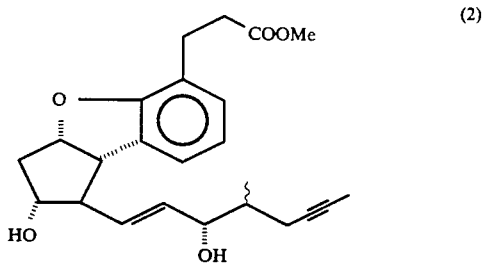

In 3 ml of anhydrous THF, 205 mg (0.423 mmol) of 15-epi-11-dehydroxy-11-(t-butyldimethylsilyloxy)-16-methyl-2,5,6,7-tetranor-18,19-tetradehyhdro-4,8-inter-m-phenylene PGI₂ methyl ester was dissolved and then 233 mg (0.888 mmol) of triphenylphosphine and 108 mg (0.884 mmol) of benzoic acid were added thereto and the resulting mixture was stirred at room temperature. To the thus obtained reaction mixture, 892 mg (0.892 mmol) of diethylazodicarboxylate in 6 ml of anhydrous THF was added for 5 minutes and the resulting mixture was stirred for 2 hours at room temperature. The solvent was evapolated under reduced pressure and the residue was dissolved in 10 ml of methanol and 1 g of potassium carbonate was added thereto, followed by being stirred for 16 hours at room temperature. The solvent was evaporated under reduced pressure and the residue was dissolved in 10 ml of ethyl acetate and the resultant was washed with water to neutralize the same. The solvent was evapolated under reduced pressure and the residue was dissolved in 40 ml of acetic acid-water-THF (65:35:10), followed by being stirred at 25° C. for 30 hours. To the thus obtained reaction mixture, sodium hydrogen carbonate was added to neutralize the same. THF was evaporated under reduced pressure and the resultant was extracted with ethyl acetate, washed with water and with saturated aqueous sodium chloride solution, and dried over anhydrous sodium sulfate. After evapolating the solvent, the thus obtained residue was purified by Lober column (commercially available from Merck Co., Inc., eluant; ethyl acetate:cyclohexane=1:2) to obtain 101 mg of the captioned compound.

IR (neat) ν: 3380, 2948, 1728, 1592, 1442, 1366, 1335, 1295, 1247, 1187, 1065, 1030, 999, 965, 884, 875, 833, 761, 742 cm⁻¹

NMR (CDCl₃, δ): 0.90–1.11 (3H, m , 1.60–1.89 (3H, m), 1.89–3.09 (10H, m), 2.27 (2H, s), 3.44 (1H, t, J=8.95 Hz), 3.66 (3H, s), 3.74–4.26 (2H, m), 4.98–5.22 (1H, m), 5.55–5.73 (2H, m), 6.61–7.10 (3H, m)

Mass (EI method, m/e): 398 (M+)

The same procedure as in Example 52 except that 15-epi-11-dehydroxy-11-diphenylmethylsilyloxy-16-methyl-2,5,6,7-tetranor-18,19-tetradehyhdro-4,8-inter-m-phenylene PGI₂ methyl ester, 15-epi-11-dehydroxy-11-(t-butyldiphenylsilyloxy)-16-methyl-2,5,6,7-tetranor-18,19-tetradehydro-4,8-inter-m-phenylene PGI₂ methyl ester, 15-epi-11-dehydroxy-11-(di-t-butylsilyloxy)-16-methyl-2,5,6,7-tetranor-18,19-tetradehydro-4,8-inter-m-phenylene PGI₂ methyl ester, 15-epi-11-dehydroxy-11-trimethylsilyloxy-16-methyl-2,5,6,7-tetranor-18,19-tetradehyhdro-4,8-inter-m-phenylene PGI₂ methyl ester or 15-epi-11-dehydroxy-11-triphenylsilyloxy-16-methyl-2,5,6,7-tetranor-18,19-tetradehyhdro-4,8-inter-m-phenylene PGI$_2$ methyl ester is employed in place of 15-epi-11-dehydroxy-11-(t-butyldimethylsilyloxy)-16-methyl-2,5,6,7-tetranor-18,19-tetradehyhdro-4,8-inter-m-phenylene PGI$_2$ methyl ester also yields the captioned compound.

The same procedure as in Example 52 except that 15-epi-11-dehydroxy-11-diphenylmethylsilyloxy-16-methyl-2,5,6,7-tetranor-18,19-tetradehyhdro-4,8-inter-m-phenylene PGI$_2$ ethyl ester, 15-epi-11-dehydroxy-11-(t-butyldiphenylsilyloxy)-16-methyl-2,5,6,7-tetranor-18,19-tetradehyhdro-4,8-inter-m-phenylene PGI$_2$ ethyl ester, 15-epi-11-dehydroxy-11-(di-t-butylsilyloxy)-16-methyl-2,5,6,7-tetranor-18,19-tetradehyhdro-4,8-inter-m-phenylene PGI$_2$ ethyl ester, 15-epi-11-dehydroxy-11-trimethylsilyloxy-16-methyl-2,5,6,7-tetranor-18,19-tetradehydro-4,8-inter-m-phenylene PGI$_2$ ethyl ester or 15-epi-11-dehydroxy-11-triphenylsilyloxy-16-methyl-2,5,6-tetranor-18,19-tetradehydro-4,8-inter-m-phenylene PGI$_2$ ethyl ester is employed in place of 15-epi-11-dehydroxy-11-(t-butyldimethylsilyloxy)-16-methyl-2,5,6,7-tetranor-18,19-tetradehyhdro-4,8-inter-m-phenylene PGI$_2$ methyl ester yields 16-methyl-2,5,6,7-tetranor-18,19-tetradehydro-4,8-inter-m-phenylene PGI$_2$ ethyl ester. The same procedure as in Example 52 except that 15-epi-11-dehydroxy-11-trimethylsilyloxy-16-methyl-20-homo-2,5,6,7-tetranor-18,19-tetradehyhdro-4,8-inter-m-phenylene PGI$_2$ methyl ester, 15-epi-11-dehydroxy-11-(t-butyldiphenylsilyloxy)-16-methyl-20-homo-2,5,6,7-tetranor-18,19-tetradehyhdro-4,8-inter-m-phenylene PGI$_2$ methyl ester, 15-epi-11-dehydroxy-11-diphenylmethylsilyloxy-16-methyl-20-homo-2,5,6,7-tetranor-18,19-tetradehydro-4,8-inter-m-phenylene PGI$_2$ methyl ester, 15-epi-11-dehydroxy-11-(di-t-butylsilyloxy)-16-methyl-20-homo-2,5,6,7-tetranor-18,19-tetradehyhdro-4,8-inter-m-phenylene PGI$_2$ methyl ester or 15-epi-11-dehydroxy-11-triphenylsilyloxy-16-methyl-20-homo-2,5,6,7-tetranor-18,19-tetradehyhdro-4,8-inter-m-phenylene PGI$_2$ methyl ester is employed in place of 15-epi-11-dehydroxy-11-(t-butyldimethylsilyloxy)-16-methyl-2,5,6,7-tetranor-18,19-tetradehyhdro-4,8-inter-m-phenylene PGI$_2$ methyl ester yields 16-methyl-20-homo-2,5,6,7-tetranor-18,19-tetradehydro-4,8-inter-m-phenylene PGI$_2$ methyl ester. The same procedure as in Example 52 except that 15-epi-11-dehydroxy-11-trimethylsilyloxy-16-methyl-20-homo-2,5,6,7-tetranor-18,19-tetradehyhdro-4,8-inter-m-phenylene PGI$_2$ ethyl ester, 15-epi-11-dehydroxy-11-(t-butyldiphenylsilyloxy)-16-methyl-20-homo-2,5,6,7-tetranor-18,19-tetradehyhdro-4,8-inter-m-phenylene PGI$_2$ ethyl ester, 15-epi-11-dehydroxy-11-diphenylmethylsilyloxy-16-methyl-20-homo-2,5,6,7-tetranor-18,19-tetradehyhdro-4,8-inter-m-phenylene PGI$_2$ ethyl ester, 15-epi-11-dehydroxy-11-(di-t-butylsilyloxy)-16-methyl-20-homo-2,5,6,7-tetranor-18,19-tetradehyhdro-4,8-inter-m-phenylene PGI$_2$ ethyl ester or 15-epi-11-dehydroxy-11-triphenylsilyloxy-16-methyl-20-homo-2,5,6,7-tetranor-18,19-tetradehyhdro-4,8-inter-m-phenylene PGI$_2$ ethyl ester is employed in place of 15-epi-11-dehydroxy-11-(t-butyldimethylsilyloxy)-16-methyl-2,5,6,7-tetranor-18,19-tetradehydro-4,8-inter-m-phenylene PGI$_2$ methyl ester yields 16-methyl-20-homo-2,5,6,7-tetranor-4-oxa-18,19-tetradehydro-4,8-inter-m-phenylene PGI$_2$ ethyl ester. The same procedure as in Example 52 was repeated except that 15-epi-11-dehydroxy-11-trimethylsilyloxy-16-methyl-5,6,7-trinor-18,19-tetradehyhdro-4,8-inter-m-phenylene PGI$_2$ methyl ester, 15-epi-11-dehydroxy-11-(t-butyldiphenylsilyloxy)-16-methyl-5,6,7-trinor-18,19-tetradehyhdro-4,8-inter-m-phenylene PGI$_2$ methyl ester, 15-epi-11-dehydroxy-11-diphenylmethylsilyloxy-16-methyl-5,6,7-trinor-18,19-tetradehyhdro-4,8-inter-m-phenylene PGI$_2$ methyl ester, 15-epi-11-dehydroxy-11-(di-t-butylsilyloxy)-16-methyl-5,6,7-trinor-18,19-tetradehyhdro-4,8-inter-m-phenylene PGI$_2$ methyl ester or 15-epi-11-dehydroxy-11-triphenylsilyloxy-16-methyl-5,6,7-trinor-18,19-tetradehydro-4,8-inter-m-phenylene PGI$_2$ methyl ester is employed in place of 15-epi-11-dehydroxy-11-(t-butyldimethylsilyloxy)-16-methyl-2,5,6,7-tetranor-18,19-tetradehyhdro-4,8-inter-m-phenylene PGI$_2$ methyl ester yields 16-methyl-5,6,7-trinor-18,19-tetradehydro-4,8-inter-m-phenylene PGI$_2$ methyl ester. The same procedure as in Example 52 except that 15-epi-11-dehydroxy-11-trimethylsilyloxy-16-methyl-5,6,7-trinor-18,19-tetradehyhdro-4,8-inter-m-phenylene PGI$_2$ ethyl ester, 15-epi-11-dehydroxy-11-(t-butyldiphenylsilyloxy)-16-methyl-5,6,7-trinor-18,19-tetradehyhdro-4,8-inter-m-phenylene PGI$_2$ ethyl ester, 15-epi-11-dehydroxy-11-diphenylmethylsilyloxy-16-methyl-5,6,7-trinor-18,19-tetradehyhdro-4,8-inter-m-phenylene PGI$_2$ ethyl ester, 15-epi-11-dehydroxy-11-(di-t-butylsilyloxy)-16-methyl-5,6,7-trinor-18,19-tetradehyhdro-4,8-inter-m-phenylene PGI$_2$ ethyl ester or 15-epi-11-dehydroxy-11-triphenylsilyloxy-16-methyl-5,6,7-trinor-18,19-tetradehyhdro-4,8-inter-m-phenylene PGI$_2$ ethyl ester is employed in place of 15-epi-11-dehydroxy-11-(t-butyldimethylsilyloxy)-16-methyl-2,5,6,7-tetranor-18,19-tetradehyhdro-4,8-inter-m-phenylene PGI$_2$ methyl ester yields 16-methyl-5,6,7-trinor-18,19-tetradehydro-4,8-inter-m-phenylene PGI$_2$ ethyl ester. The same procedure as in Example 52 except that 15-epi-11-dehydroxy-11-(t-butyldiphenylsilyloxy)-16-methyl-20-homo-5,6,7-trinor-18,19-tetradehyhdro-4,8-inter-m-phenylene PGI$_2$ methyl ester, 15-epi-11-dehydroxy-11-diphenylmethylsilyloxy-16-methyl-20-homo-5,6,7-trinor-18,19-tetradehyhdro-4,8-inter-m-phenylene PGI$_2$ methyl ester, 15-epi-11-dehydroxy-11-(di-t-butylsilyloxy)-16-methyl-20-homo-5,6,7-trinor-18,19-tetradehyhdro-4,8-inter-m-phenylene PGI$_2$ methyl ester or 15-epi-11-dehydroxy-11-triphenylsilyloxy-16-methyl-20-homo-5,6,7-trinor-18,19-tetradehyhdro-4,8-inter-m-phenylene PGI$_2$ methyl ester is employed in place of 15-epi-11-dehydroxy-11-(t-butyldimethylsilyloxy)-16-methyl-2,5,6,7-tetranor-18,19-tetradehyhdro-4,8-inter-m-phenylene PGI$_2$ methyl ester yields 16-methyl-20-homo-5,6,7-trinor-18,19-tetradehydro-4,8-inter-m-phenylene PGI$_2$ methyl ester. The same procedure as in Example 52 except that 15-epi-11-dehydroxy-11-(t-butyldiphenylsilyloxy)-16-methyl-20-homo-5,6,7-trinor-18,19-tetradehyhdro-4,8-inter-m-phenylene PGI$_2$ ethyl ester, 15-epi-11-dehydroxy-11-diphenylmethylsilyloxy-16-methyl-20-homo-5,6,7-trinor-18,19-tetradehyhdro-4,8-inter-m-phenylene PGI$_2$ ethyl ester, 15-epi-11-dehydroxy-11-diphenylmethylsilyloxy-16-methyl-20-homo-5,6,7-trinor-18,19-tetradehyhdro-4,8-inter-m-phenylene PGI$_2$ ethyl ester, 15-epi-11-dehydroxy-11-(di-t-butylsilyloxy)-16-methyl-20-homo-5,6,7-trinor-18,19-tetradehyhdro-4,8-inter-m-phenylene PGI$_2$ ethyl ester or 15-epi-11-dehydroxy-11-triphenylsilyloxy-16-methyl-20-homo-5,6,7-trinor-18,19-tetradehyhdro-4,8-inter-m-phenylene PGI$_2$ ethyl ester is employed in place of 15-epi-11-dehydroxy-11-(t-butyldimethylsilyloxy)-16-methyl-2,5,6,7-tetranor-18,19-tetradehyhdro-4,8-inter-m-phenylene PGI$_2$ methyl ester yields 16-methyl-20-homo-5,6,7-trinor-18,19-tetradehydro-4,8-inter-m-phenylene PGI$_2$ ethyl ester. The same procedure as in Example 52 except that 15-epi-11-dehydroxy-11-(t-butyldiphenylsilyloxy)-5,6,7-trinor-18,19-tetradehyhdro-4,8-inter-m-phenylene PGI$_2$ methyl ester, 15-epi-11-dehydroxy-11-diphenylmethylsilyloxy-5,6,7-trinor-18,19-tetradehyhdro-4,8-inter-m-phenylene PGI$_2$ methyl ester, 15-epi-11-dehydroxy-11-(di-t-butylsilyloxy)-5,6,7-trinor-18,19-tetradehyhdro-4,8-inter-m-phenylene PGI$_2$ methyl ester or 15-epi-11-dehydroxy-11-triphenylsilyloxy-5,6,7-trinor-18,19-tetradehydro-4,8-inter-m-phenylene PGI$_2$ methyl ester is employed in place of 15-epi-11-dehydroxy-11-(t-butyldimethylsilyloxy)-16-methyl-2,5,6,7-tetranor-18,19-tetradehydro-4,8-inter-m-phenylene PGI$_2$ methyl ester yields 5,6,7-trinor-18,19-tetradehydro-4,8-inter-m-phenylene PGI$_2$ methyl ester. The same procedure as in Example 52 except that 15-epi-11-dehydroxy-11-(t-butyldiphenylsilyloxy)-5,6,7-trinor-18,19-tetradehyhdro-4,8-inter-m-phenylene PGI$_2$ ethyl ester, 15-epi-11-dehydroxy-11-diphenylmethylsilyloxy-5,6,7-trinor-18,19-tetradehyhdro-4,8-inter-m-phenylene PGI$_2$ ethyl ester, 15-epi-11-dehydroxy-11-(di-t-butylsilyloxy)-5,6,7-trinor-18,19-tetradehyhdro-4,8-inter-m-phenylene PGI$_2$ ethyl ester or 15-epi-11-dehydroxy-11-triphenylsilyloxy-5,6,7-trinor-b 18,19tetradehydro-4,8-inter-m-phenylene PGI$_2$ ethyl ester is employed in place of 15-epi-11-dehydroxy-11-(t-butyldimethylsilyloxy)-16-methyl-2,5,6,7-tetranor-18,19-tetradehyhdro-4,8-inter-m-phenylene PGI$_2$ methyl ester yields 5,6,7-trinor-18,19-tetradehydro-4,8-inter-m-phenylene PGI$_2$ ethyl ester. The same procedure as in Example 52 except that 15-epi-11-dehydroxy-11-(t-butyldiphenylsilyloxy)-2,5,6,7-tetranor-18,19-tetradehyhdro-4,8-inter-m-phenylene PGI$_2$ methyl ester, 15-epi-11-dehydroxy-11-diphenylmethylsilyloxy-2,5,6,7-tetranor-18,19-tetradehyhdro-4,8-inter-m-phenylene PGI$_2$ methyl ester, 15-epi-11-dehydroxy-11-(di-t-butylsilyloxy)-2,5,6,7-tetranor-18,19-tetradehyhdro-4,8-inter-m-phenylene PGI$_2$ methyl ester or 15-epi-11-dehydroxy-11-triphenylsilyloxy-2,5,6,7-tetranor-18,19-tetradehyhdro-4,8-inter-m-phenylene PGI$_2$ methyl ester is employed in place of 15-epi-11-dehydroxy-11-(t-butyldimethylsilyloxy)-16-methyl-2,5,6,7-tetranor-18,19-tetradehyhdro-4,8-inter-m-phenylene PGI$_2$ methyl ester yields 2,5,6,7-tetranor-18,19-tetradehydro-4,8-inter-m-phenylene PGI$_2$ methyl ester. The same procedure as in Example 52 except that 15-epi-11-dehydroxy-11-(t-butyldiphenylsilyloxy)-2,5,6,7-tetranor-18,19-tetradehyhdro-4,8-inter-m-phenylene PGI$_2$ ethyl ester, 15-epi-11-dehydroxy-11-diphenylmethylsilyloxy-2,5,6,7-tetranor-18,19-tetradehyhdro-4,8-inter-m-phenylene PGI$_2$ ethyl ester, 15-epi-11-dehydroxy-11-(di-t-butylsilyloxy)-2,5,6,7-tetranor-18,19-tetradehyhdro-4,8-inter-m-phenylene PGI$_2$ ethyl ester or 15-epi-11-dehydroxy-11-triphenylsilyloxy-2,5,6,7-tetranor-18,19-tetradehyhdro-4,8-inter-m-phenylene PGI$_2$ ethyl ester is employed in place of 15-epi-11-dehydroxy-11-(t-butyldimethylsilyloxy)-16-methyl-2,5,6,7-tetranor-18,19-tetradehyhdro-4,8-inter-m-phenylene PGI$_2$ methyl ester yields 2,5,6,7-tetranor-18,19-tetradehydro-4,8-inter-m-phenylene PGI$_2$ ethyl ester. The same procedure as in Example 52 except that 15-epi-11-dehydroxy-11-trimethylsilyloxy-2,5,6,7-tetranor-4-oxa-18,19-tetradehydro-4,8-inter-m-phenylene PGI$_2$ methyl ester, 15-epi-11-dehydroxy-11-(t-butyldiphenylsilyloxy)-2,5,6,7-tetranor-4-oxa-18,19-tetradehyhdro-4,8-inter-m-phenylene PGI$_2$ methyl ester, 15-epi-11-dehydroxy-11-diphenylmethylsilyloxy-2,5,6,7-tetranor-4-oxa-18,19-tetradehyhdro-4,8-inter-m-phenylene PGI$_2$ methyl ester, 15-epi-11-dehydroxy-11-(di-t-butylsilyloxy)-2,5,6,7-tetranor-4-oxa-18,19-tetradehyhdro-4,8-inter-m-phenylene PGI$_2$ methyl ester or 15-epi-11-dehydroxy-11-triphenylsilyloxy-2,5,6,7-tetranor-4-oxa-18,19-tetradehyhdro-4,8-inter-m-phenylene PGI$_2$ methyl ester is employed in place of 15-epi-11-dehydroxy-11-(t-butyldimethylsilyloxy)-16-methyl-2,5,6,7-tetranor-18,19-tetradehyhdro-4,8-inter-m-phenylene PGI$_2$ methyl ester yields 2,5,6,7-tetranor-4-oxa-18,19-tetradehydro-4,8-inter-m-phenylene PGI$_2$ methyl ester. The same procedure as in Example 52 except that 15-epi-11-dehydroxy-11-(t-butyldiphenylsilyloxy)-2,5,6,7-tetranor-4-oxa-18,19-tetradehyhdro-4,8-inter-m-phenylene PGI$_2$ ethyl ester, 15-epi-11-dehydroxy-11-diphenylmethylsilyloxy-2,5,6,7-tetranor-4-oxa-18,19-tetradehyhdro-4,8-inter-m-phenylene PGI$_2$ ethyl ester, 15-epi-11-dehydroxy-11-diphenylmethylsilyloxy-2,5,6,7-tetranor-4-oxa-18,19-tetradehyhdro-4,8-inter-m-phenylene PGI$_2$ ethyl ester, 15-epi-11-dehydroxy-11-(di-t-butylsilyloxy)-2,5,6,7-tetranor-4-oxa-18,19-tetradehyhdro-4,8-inter-m-phenylene PGI$_2$ ethyl ester or 15-epi-11-dehydroxy-11-triphenylsilyloxy-2,5,6,7-tetranor-4-oxa-18,19-tetradehyhdro-4,8-inter-m-phenylene PGI$_2$ ethyl ester is employed in place of 15-epi-11-dehydroxy-11-(t-butyldimethylsilyloxy)-16-methyl-2,5,6,7-tetranor-18,19-tetradehyhdro-4,8-inter-m-phenylene PGI$_2$ methyl ester yields 2,5,6,7-tetranor-4-oxa-18,19-tetradehydro-4,8-inter-m-phenylene PGI$_2$ ethyl ester. The same procedure as in Example 52 except that 15-epi-11-dehydroxy-11-(t-butyldiphenylsilyloxy)-16-methyl-2,5,6,7-tetranor-4-oxa-18,19-tetradehyhdro-4,8-inter-m-phenylene PGI₂ methyl ester, 15-epi-11-dehydroxy-11-diphenylmethylsilyloxy-16-methyl-2,5,6,7-tetranor-4-oxa-18,19-tetradehyhdro-4,8-inter-m-phenylene PGI₂ methyl ester, 15-epi-11-dehydroxy-11-(di-t-butylsilyloxy)-16-methyl-2,5,6,7-tetranor-4-oxa-18,19-tetradehyhdro-4,8-inter-m-phenylene PGI₂ methyl ester or 15-epi-11-dehydroxy-11-triphenylsilyloxy-16-methyl-2,5,6,7-tetranor-4-oxa-18,19-tetradehyhdro-4,8-inter-m-phenylene PGI₂ methyl ester is employed in place of 15-epi-11-dehydroxy-11-(t-butyldimethylsilyloxy)-16-methyl-2,5,6,7-tetranor-18,19-tetradehyhdro-4,8-inter-m-phenylene PGI₂ methyl ester yields 16-methyl-2,5,6,7-tetranor-4-oxa-18,19-tetradehydro-4,8-inter-m-phenylene PGI₂ methyl ester. The same procedure as in Example 52 except that 15-epi-11-dehydroxy-11-(t-butyldiphenylsilyloxy)-16-methyl-2,5,6,7-tetranor-4-oxa-18,19-tetradehyhdro-4,8-inter-m-phenylene PGI₂ ethyl ester, 15-epi-11-dehydroxy-11-diphenylmethylsilyloxy-16-methyl-2,5,6,7-tetranor-4-oxa-18,19-tetradehyhdro-4,8-inter-m-phenylene PGI₂ ethyl ester, 15-epi-11-dehydroxy-11-(di-t-butylsilyloxy)-16-methyl-2,5,6,7-tetranor-4-oxa-18,19-tetradehyhdro-4,8-inter-m-phenylene PGI₂ ethyl ester or 15-epi-11-dehydroxy-11-triphenylsilyloxy-16-methyl-2,5,6,7-tetranor-4-oxa-18,19-tetradehyhdro-4,8-inter-m-phenylene PGI₂ ethyl ester is employed in place of 15-epi-11-dehydroxy-11-(t-butyldimethylsilyloxy)-16-methyl-2,5,6,7-tetranor-18,19-tetradehyhdro-4,8-inter-m-phenylene PGI₂ methyl ester yields 16-methyl-2,5,6,7-tetranor-4-oxa-18,19-tetradehydro-4,8-inter-m-phenylene PGI₂ ethyl ester.

EXAMPLE 53

16-methyl-20-homo-2,5,6,7-tetranor-18,19-tetradehydro-4,8-inter-m-phenylene PGI₂ methyl ester (3)

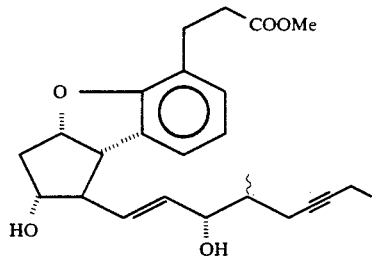

(3)

The same procedure as in Example 51 was repeated except that 156 mg of 15β epimer of 11-dehydroxy-11-(p-toluoyloxy)-16-methyl-20-homo-2,5,6,7-tetranor-18,19-tetradehydro-4,8-inter-m-phenylene PGI₂ methyl ether is employed as a substrate to obtain 75 mg of the captioned compound.

IR (neat) ν: 3380, 2960, 2930, 1730, 1590, 1440, 1360, 1250, 1185, 1060, 1030, 990, 960, 880, 850 cm⁻¹

NMR (CDCl₃, δ): 1.01 (3H, two, d, J=7.8 Hz), 1.12 (3H, two, t, J=7.8 Hz), 1.8–1.85 (1H, m), 1.9–2.0 (1H, m), 2.1–2.3 (4H, m), 2.35–2.45 (1H, m), 2.55–3.0 (7H, m), 3.42 (1H, two, t, J=8.8 Hz), 3.66 (3H, s), 3.85–3.95 (1H, m), 4.10 (1H, two, t, J=6.7 Hz), 5.05–5.15 (1H, m), 5.58 (1H, two, dd, J=6.7, 15.1 Hz), 5.67 (1H, two, dd, J=8.9, 15.1 Hz), 6.76 (1H, two, t, J=7.5 Hz), 6.9–7.0 (2H, m)

Mass (EI method, m/e): 412 (M⁺)
High resolution mass spectrum
Calcd. ($C_{25}H_{32}O_5$, M⁺): 412.2250
Found (M⁺): 412.2263

The same procedure as in Example 53 except that 15-epi-11-dehydroxy-11-acetoxy-16-methyl-20-homo-2,5,6,7-tetranor-18,19-tetradehydro-4,8-inter-m-phenylene PGI₂ methyl ester, 15-epi-11-dehydroxy-11-propionyloxy-16-methyl-20-homo-2,5,6,7-tetranor-18,19-tetradehydro-4,8-inter-m-phenylene PGI₂ methyl ester, 15-epi-11-dehydroxy-11-butyroyloxy-16-methyl-20-homo-2,5,6,7-tetranor-18,19-tetradehydro-4,8-inter-m-phenylene PGI₂ methyl ester, 15-epi-11-dehydroxy-11-octanoyloxy-16-methyl-20-homo-2,5,6,7-tetranor-18,19-tetradehydro-4,8-inter-m-phenylene PGI₂ methyl ester, 15-epi-11-dehydroxy-11-decanoyloxy-16-methyl-20-homo-2,5,6,7-tetranor-18,19-tetradehydro-4,8-inter-m-phenylene PGI₂ methyl ester, 15-epi-11-dehydroxy-11-valeroyloxy-16-methyl-20-homo-2,5,6,7-tetranor-18,19-tetradehydro-4,8-inter-m-phenylene PGI₂ methyl ester, 15-epi-11-dehydroxy-11-benzoyloxy-16-methyl-20-homo-2,5,6,7-tetranor-18,19-tetradehydro-4,8-inter-m-phenylene PGI₂ methyl ester, 15-epi-11-dehydroxy-11-(α-naphthoyloxy)-16-methyl-20-homo-2,5,6,7-tetranor-18,19-tetradehydro-4,8-inter-m-phenylene PGI₂ methyl ester, 15-epi-11-dehydroxy-11-(β-naphthoyloxy)-16-methyl-20-homo-2,5,6,7-tetranor-18,19-tetradehydro-4,8-inter-m-phenylene PGI₂ methyl ester, 15-epi-11-dehydroxy-11-(m-toluoyloxy)-16-methyl-20-homo-2,5,6,7-tetranor-18,19-tetradehydro-4,8-inter-m-phenylene PGI₂ methyl ester, 15-epi-11-dehydroxy-11-(o-toluoyloxy)-16-methyl-20-homo-2,5,6,7-tetranor-18,19-tetrahydro-4,8-inter-m-phenylene PGI₂ methyl ester or 15-epi-11-dehydroxy-11-(p-phenylbenzoyloxy)-16-methyl-20-homo-2,5,6,7-tetranor-18,19-tetradehydro-4,8-inter-m-phenylene PGI₂ methyl ester is employed in place of 15-epi-11-dehydroxy-11-(p-toluoyloxy)-16-methyl-20-homo-2,5,6,7-tetranor-18,19-tetradehydro-4,8-inter-m-phenylene PGI₂ methyl ester yields the captioned compound.

The same procedure as in Example 53 except that ethanol is employed as a solvent in place of methanol and except that 15-ep-11-dehydroxy-11-acetoxy-16-methyl-20-homo-2,5,6,7-tetranor-18,19-tetradehydro-4,8-inter-m-phenylene PGI₂ ethyl ester, 15-epi-11-dehydroxy-11-propionyloxy-16-methyl-20-homo-2,5,6,7-tetranor-18,19-tetradehydro-4,8-inter-m-phenylene PGI₂ ethyl ester, 15-epi-11-dehydroxy-11-butyroyloxy-16-methyl-20-homo-2,5,6,7-tetranor-18,19-tetradehydro-4,8-inter-m-phenylene PGI₂ ethyl ester, 15-epi-11-dehydroxy-11-octanoyloxy-16-methyl-20-homo-2,5,6,7-tetranor-18,19-tetradehydro-4,8-inter-m-phenylene PGI₂ ethyl ester, 15-epi-11-dehydroxy-11-decanoyloxy-16-methyl-20-homo-2,5,6,7-tetranor-18,19-tetradehydro-4,8-inter-m-phenylene PGI₂ ethyl ester, 15-epi-11-dehydroxy-11-valeroyloxy-16-methyl-20-homo-2,5,6,7-tetranor-18,19-tetradehydro-4,8-inter-m-phenylene PGI₂ ethyl ester, 15-epi-11-dehydroxy-11-benzoyloxy-16-methyl-20-homo-2,5,6,7-tetranor-18,19-tetradehydro-4,8-inter-m-phenylene PGI₂ ethyl ester, 15-epi-11-dehydroxy-11-(α-naphthoyloxy)-16-methyl-20-homo-2,5,6,7-tetranor-18,19-tetradehydro-4,8-inter-m-phenylene PGI₂ ethyl ester, 15-epi-11-dehydroxy-11-(β-naphthoyloxy)-16-methyl-20-homo-2,5,6,7-tetranor-18,19-tetradehydro-4,8-inter-m-phenylene PGI₂ ethyl ester, 15-epi-11-dehydroxy-11-(m-toluoyloxy)-16-methyl-20-homo-2,5,6,7-tetranor-18,19-tetradehydro-4,8-inter-m-phenylene PGI₂ ethyl ester, 15-epi-11-dehydroxy-11-(o-toluoyloxy)-16-methyl-20-homo-2,5,6,7-tatranor-18,19-tetradehydro-4,8-inter-m-phenylene PGI₂ ethyl ester or 15-epi-11-dehydroxy-11-(p-phenylbenzoyloxy)-16-methyl-20-homo-2,5,6,7-tetranor-18,19-tetradehydro-4,8-inter-m-phenylene PGI$_2$ ethyl ester is employed in place of 15-epi-11-dehydroxy-11-(p-toluoyloxy)-16-methyl-20-homo-2,5,6,7-tetranor-18,19-tetradehydro-4,8-inter-m-phenylene PGI$_2$ methyl ester yields 16-methyl-20-homo-2,5,6,7-tetranor-18,19-tetradehydro-4,8-inter-m-phenylene PGI$_2$ ethyl ester.

EXAMPLE 54

16-methyl-20-homo-2,5,6,7-tetranor-4-oxa-18,19-tetradehydro-4,8-inter-m-phenylene PGI$_2$ methyl ester (4)

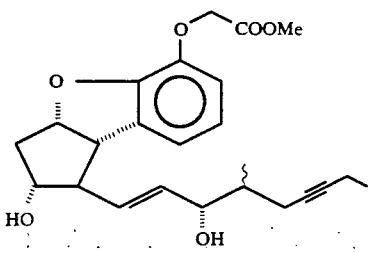

(4)

The same procedure as in Example 51 was repeated except that 178 mg of 15β epimer of 11-dehydroxy-11-(p-toluoyloxy)-16-methyl-20-homo-2,5,6,7-tetranor-4-oxa-18,19-tetradehydro-4,8-inter-m-phenylene PGI$_2$ methyl ester was employed as a substrate to obtain 82 mg of the captioned compound.

IR (neat) ν: 3450, 2970, 2930, 1745, 1660, 1615, 1590, 1490, 1460, 1440, 1330, 1290, 1245, 1195, 1115, 1040, 970, 865, 765, 730, 690 cm$^{-1}$ NMR (CDCl$_3$, δ): 1.01 (3H, two, d, J=6.8 Hz), 1.12 (3H, two, t, J=7.3 Hz), 1.7–1.9 (1H, m), 1.9–2.3 (5H, m), 2.3–2.5 (1H, m), 2.6–3.1 (3H, m), 3.44 (1H, two, t, J=8.8 Hz), 3.79 (3H, s), 3.8–3.9 (1H, m), 4.0–4.2 (1H, m), 4.72 (2H, s), 5.1–5.3 (1H, m), 5.5–5.7 (2H, m), 6.7–7.9 (3H, m)

Mass (EI method, m/e): 414 (M$^+$)
High resolution mass spectrum
Calcd. (C$_{24}$H$_{30}$O$_6$, M$^+$): 414.2042
Found (M$^+$): 414.2042

The same procedure as in Example 54 except that 15-epi-11-dehydroxy-11-acetoxy-16-methyl-20-homo-2,5,6,7-tetranor-4-oxa-18,19-tetradehydro-4,8-inter-m-phenylene PGI$_2$ methyl ester, 15-epi-11-dehydroxy-11-propionyloxy-16-methyl-20-homo-2,5,6,7-tetranor-4-oxa-18,19-tetradehydro-4,8-inter-m-phenylene PGI$_2$ methyl ester, 15-epi-11-dehydroxy-11-butyroyloxy-16-methyl-20-homo-2,5,6,7-tetranor-4-oxa-18,19-tetradehydro-4,8-inter-m-phenylene PGI$_2$ methyl ester, 15-epi-11-dehydroxy-11-octanoyloxy-16-methyl-20-homo-2,5,6,7-tetranor-4-oxa-18,19-tetradehydro-4,8-inter-m-phenylene PGI$_2$ methyl ester, 15-epi-11-dehydroxy-11-decanoyloxy-16-methyl-20-homo-2,5,6,7-tetranor-4-oxa-18,19-tetradehydro-4,8-inter-m-phenylene PGI$_2$ methyl ester, 15-epi-11-dehydroxy-11-valeroyloxy-16-methyl-20-homo-2,5,6,7-tetranor-4-oxa-18,19-tetradehydro-4,8-inter-m-phenylene PGI$_2$ methyl ester, 15-epi-11-dehydroxy-11-benzoyloxy-16-methyl-20-homo-2,5,6,7-tetranor-4-oxa-18,19-tetradehydro-4,8-inter-m-phenylene PGI$_2$ methyl ester, 15-epi-11-dehydroxy-11-(α-naphthoyloxy)-16-methyl-20-homo-2,5,6,7-tetranor-4-oxa-18,19-tetradehydro-4,8-inter-m-phenylene PGI$_2$ methyl ester, 15-epi-11-dehydroxy-11-(β-naphthoyloxy)-16-methyl-20-homo-2,5,6,7-tetranor-4-oxa-18,19-tetradehydro-4,8-inter-m-phenylene PGI$_2$ methyl ester, 15-epi-11-dehydroxy-11-(m-toluoyloxy)-16-methyl-20-homo-2,5,6,7-tetranor-4-oxa-18,19-tetradehydro-4,8-inter-m-phenylene PGI$_2$ methyl ester, 15-epi-11-dehydroxy-11-(o-toluoyloxy)-16-methyl-20-homo-2,5,6,7-tetranor-4-oxa-18,19-tetradehydro-4,8-inter-m-phenylene PGI$_2$ methyl ester or 15-epi-11-dehydroxy-11-(p-phenylbenzoyloxy)-16-methyl-20-homo-2,5,6,7-tetranor-4-oxa-18,19-tetradehydro-4,8-inter-m-phenylene PGI$_2$ methyl ester is employed in place of 15-epi-11-dehydroxy-11-(p-toluoyloxy)-16-methyl-20-homo-2,5,6,7-tetranor-4-oxa-18,19-tetradehydro-4,8-inter-m-phenylene PGI$_2$ methyl ester yields the captioned compound.

The same procedure as in Example 53 except that ethanol is employed as a solvent in place of methanol and except that 15-epi-11-dehydroxy-11-acetoxy-16-methyl-20-homo-2,5,6,7-tetranor-4-oxa-18,19-tetradehydro-4,8-inter-m-phenylene PGI$_2$ ethyl ester, 15-epi-11-dehydroxy-11-propionyloxy-16-methyl-20-homo-2,5,6,7-tetranor-4-oxa-18,19-tetradehydro-4,8-inter-m-phenylene PGI$_2$ ethyl ester, 15-epi-11-dehydroxy-11-butyroyloxy-16-methyl-20-homo-2,5,6,7-tetranor-4-oxa-18,19-tetradehydro-4,8-inter-m-phenylene PGI$_2$ ethyl ester, 15-epi-11-dehydroxy-11-octanoyloxy-16-methyl-20-homo-2,5,6,7-tetranor-4-oxa-18,19-tetradehydro-4,8-inter-m-phenylene PGI$_2$ ethyl ester, 15-epi-11-dehydroxy-11-decanoyloxy-16-methyl-20-homo-2,5,6,7-tetranor-4-oxa-18,19-tetradehydro-4,8-inter-m-phenylene PGI$_2$ ethyl ester, 15-epi-11-dehydroxy-11-valeroyloxy-16-methyl-20-homo-2,5,6,7-tetranor-4-oxa-18,19-tetradehydro-4,8-inter-m-phenylene PGI$_2$ ethyl ester, 15-epi-11-dehydroxy-11-benzoyloxy-16-methyl-20-homo-2,5,6,7-tetranor-4-oxa-18,19-tetradehydro-4,8-inter-m-phenylene PGI$_2$ ethyl ester, 15-epi-11-dehydroxy-11-(α-naphthoyloxy)-16-methyl-20-homo-2,5,6,7-tetranor-4-oxa-18,19-tetradehydro-4,8-inter-m-phenylene PGI$_2$ ethyl ester, 15-epi-11-dehydroxy-11-(β-naphthoyloxy)-16-methyl-20-homo-2,5,6,7-tetranor-4-oxa-18,19-tetradehydro-4,8-inter-m-phenylene PGI$_2$ ethyl ester, 15-epi-11-dehydroxy-11-(m-toluoyloxy)-16-methyl-20-homo-2,5,6,7-tetranor-4-oxa-18,19-tetradehydro-4,8-inter-m-phenylene PGI$_2$ ethyl ester, 15-epi-11-dehydroxy-11-(o-toluoyloxy)-16-methyl-20-homo-2,5,6,7-tatranor-4-oxa-18,19-tetradehydro-4,8-inter-m-phenylene PGI$_2$ ethyl ester or 15-epi-11-dehydroxy-11-(p-phenylbenzoyloxy)-16-methyl-20-homo-2,5,6,7-tetranor-4-oxa-18,19-tetradehydro-4,8-inter-m-phenylene PGI$_2$ ethyl ester is employed in place of 15-epi-11-dehydroxy-11-(p-toluoyloxy)-16-methyl-20-homo-2,5,6,7-tetranor-4-oxa-18,19-tetradehydro-4,8-inter-m-phenylene PGI$_2$ methyl ester yields 16-methyl-20-homo-2,5,6,7-tetranor-4-oxa-18,19-tetradehydro-4,8-inter-m-phenylene PGI$_2$ ethyl ester.

EXAMPLE 55

16-methyl-2,5,6,7-tetranor-4-oxa-18,19-tetradehydro-4,8-inter-m-phenylene PGI$_2$ methyl ester (5)

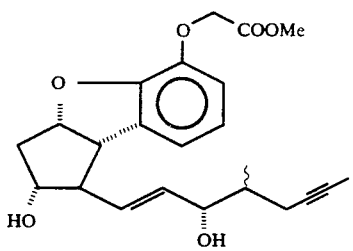

(5)

The same procedure as in Example 51 was repeated except that 163 mg of 15β epimer of 11-dehydroxy-11-(p-toluoyloxy)-16-methyl-2,5,6,7-tetranor-4-oxa-18,19-tetradehydro-4,8-inter-m-phenylene PGI$_2$ methyl ester was employed as a substrate to obtain 82 mg of the captioned compound.

IR (neat) ν: 3380, 2970, 2930, 1750, 1620, 1595, 1490, 1460, 1440, 1380, 1295, 1210, 1200, 1120, 1020, 970, 890, 855, 830, 760, 730, 665 cm$^{-1}$ NMR (CDCl$_3$, δ): 1.00 (3H, two, d, J=6.8 Hz), 1.7-1.9 (4H, m), 1 9-2.5 (4H, m), 2.6-2.7 (1H, m), 2.5-3.1 (2H, m), 3.50 (1H, two, t, J=8.60 Hz), 3.79 (3H, s), 3.8-4.0 (1H, m), 4.0-4.0 (1H, m), 4.72 (2H, s), 5.13-5.3 (1H, m), 5.5-5.8 (2H, m), 6.6-6.9 (3H, m)

Mass (EI method, m/e): 400 (M$^+$)

High resolution mass spectrum

Calcd. (C$_{23}$H$_{28}$O$_6$, M$^+$): 400.1886

Found (M$^+$): 400.1892

The same procedure as in Example 55 except that 15-epi-11-dehydroxy-11-acetoxy-16-methyl-2,5,6,7-tetranor-4-oxa-18,19-tetradehydro-4,8-inter-m-phenylene PGI$_2$ methyl ester, 15-epi-11-dehydroxy-11-propionyloxy-16-methyl-2,5,6,7-tetranor-4-oxa-18,19-tetradehydro-4,8-inter-m-phenylene PGI$_2$ methyl ester, 15-epi-11-dehydroxy-11-butyroyloxy-16-methyl-2,5,6,7-tetranor-4-oxa-18,19-tetradehydro-4,8-inter-m-phenylene PGI$_2$ methyl ester, 15-epi-11-dehydroxy-11-octanoyloxy-16-methyl-2,5,6,7-tetranor-4-oxa-18,19-tetradehydro-4,8-inter-m-phenylene PGI$_2$ methyl ester, 15-epi-11-dehydroxy-11-decanoyloxy-16-methyl-2,5,6,7-tetranor-4-oxa-18,19-tetradehydro-4,8-inter-m-phenylene PGI$_2$ methyl ester, 15-epi-11-dehydroxy-11-valeroyloxy-16-methyl-2,5,6,7-tetranor-4-oxa-18,19-tetradehydro-4,8-inter-m-phenylene PGI$_2$ methyl ester, 15-epi-11-dehydroxy-11-benzoyloxy-16-methyl-2,5,6,7-tetranor-4-oxa-18,19-tetradehydro-4,8-inter-m-phenylene PGI$_2$ methyl ester, 15-epi-11-dehydroxy-11-(α-naphthoyloxy)-16-methyl-2,5,6,7-tetranor-4-oxa-18,19-tetradehydro-4,8-inter-m-phenylene PGI$_2$ methyl ester, 15-epi-11-dehydroxy-11-(β-naphthoyloxy)-16-methyl-2,5,6,7-tetranor-4-oxa-18,19-tetradehydro-4,8-inter-m-phenylene PGI$_2$ methyl ester, 15-epi-11-dehydroxy-11-(m-toluoyloxy)-16-methyl-2,5,6,7-tetranor-4-oxa-18,19-tetradehydro-4,8-inter-m-phenylene PGI$_2$ methyl ester, 15-epi-11-dehydroxy-11-(o-toluoyloxy)-16-methyl-2,5,6,7-tatranor-4-oxa-18,19-tetradehydro-4,8-inter-m-phenylene PGI$_2$ methyl ester or 15-epi-11-dehydroxy-11-(p-phenylbenzoyloxy)-16-methyl-2,5,6,7-tetranor-4-oxa-18,19-tetradehydro-4,8-inter-m-phenylene PGI$_2$ methyl ester is employed in place of 15-epi-11-dehydroxy-11-(p-toluoyloxy)-16-methyl-2,5,6,7-tetranor-4-oxa-18,19-tetradehydro-4,8-inter-m-phenylene PGI$_2$ methyl ester yields 16-methyl-2,5,6,7-tetranor-4-oxa-18,19-tetradehydro-4,8-inter-m-phenylene PGI$_2$ methyl ester yields the captioned compound.

The same procedure as in Example 55 except that ethanol is employed as a solvent in place of methanol and except that 15-epi-11-dehydroxy-11-acetoxy-16-methyl-2,5,6,7-tetranor-4-oxa-18,19-tetradehydro-4,8-inter-m-phenylene PGI$_2$ ethyl ester, 15-epi-11-dehydroxy-11-propionyloxy-16-methyl-2,5,6,7-tetranor-4-oxa-18,19-tetradehydro-4,8-inter-m-phenylene PGI$_2$ ethyl ester, 15-epi-11-dehydroxy-11-butyroyloxy-16-methyl-2,5,6,7-tetranor-4-oxa-18,19-tetradehydro-4,8-inter-m-phenylene PGI$_2$ ester, 15-epi-11-dehydroxy-11-octanoyloxy-16-methyl-2,5,6,7-tetranor-4-oxa-18,19-tetradehydro-4,8-inter-m-phenylene PGI$_2$ ethyl ester, 15-epi-11-dehydroxy-11-decanoyloxy-16-methyl-2,5,6,7-tetranor-4-oxa-18,19-tetradehydro-4,8-inter-m-phenylene PGI$_2$ ethyl ester, 15-epi-11-dehydroxy-11-valeroyloxy-16-methyl-2,5,6,7-tetranor-4-oxa-18,19-tetradehydro-4,8-inter-m-phenylene PGI$_2$ ethyl ester, 15-epi-11-dehydroxy-11-benzoyloxy-16-methyl-2,5,6,7-tetranor-4-oxa-18,19-tetradehydro-4,8-inter-m-phenylene PGI$_2$ ethyl ester, 15-epi-11-dehydroxy-11-(α-naphthoyloxy)-16-methyl-2,5,6,7-tetranor-4-oxa-18,19-tetradehydro-4,8-inter-m-phenylene PGI$_2$ ethyl ester, 15-epi-11-dehydroxy-11-(β-naphthoyloxy)-16-methyl-2,5,6,7-tetranor-4-oxa-18,19-tetradehydro-4,8-inter-m-phenylene PGI$_2$ ethyl ester, 15-epi-11-dehydroxy-11-(m-toluoyloxy)-16-methyl-2,5,6,7-tetranor-4-oxa-18,19-tetradehydro-4,8-inter-m-phenylene PGI$_2$ ethyl ester, 15-epi-11-dehydroxy-11-(o-toluoyloxy)-16-methyl-2,5,6,7-tatranor-4-oxa-18,19-tetradehydro-4,8-inter-m-phenylene PGI$_2$ ethyl ester or 15-epi-11-dehydroxy-11-(p-phenylbenzoyloxy)-16-methyl-2,5,6,7-tetranor-4-oxa-18,19-tetradehydro-4,8-inter-m-phenylene PGI$_2$ ethyl ester is employed in place of 15-epi-11-dehydroxy-11-(p-toluoyloxy)-16-methyl-2,5,6,7-tetranor-4-oxa-18,19-tetradehydro-4,8-inter-m-phenylene PGI$_2$ methyl ester yields 16-methyl-2,5,6,7-tetranor-4-oxa-18,19-tetradehydro-4,8-inter-m-phenylene PGI$_2$ ethyl ester.

REFERENCE EXAMPLE 4

16-methyl-5,6,7-trinor-18,19-tetradehydro-4,8-inter-m-phenylene PGI$_2$ ethyl ester (6)

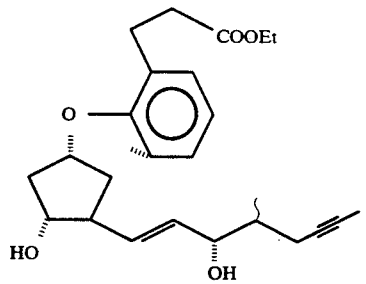

(6)

In 2 ml of anhydrous THF, 148 mg (0.279 mmol) of 15-epi-11-dehydroxy-11-(p-toluoyloxy)-16-methyl-5,6,7-trinor-18,19-tetradehydro-4,8-inter-m-phenylene PGI$_2$ methyl ester was dissolved and then 146 mg (0.556 mmol) of triphenylphosphine and 69 mg (0.565 mmol) of benzoic acid were added thereto and the resulting mixture was stirred at room temperature. To the thus obtained reaction mixture, 115 mg (0.558 mmol) of diethylazodicarboxylate in 6 ml of anhydrous THF was added for 5 minutes and the resulting mixture was stirred for 2 hours at room temperature. The solvent was evapolated under reduced pressure and the residue was dissolved in 10 ml of anhydrous ethanol and 0.2 ml of 1.44M sodium ethoxide was added thereto, followed by being stirred for 18 hours at room temperature. The solvent was evapolated under reduced pressure and the residue was dissolved in 10 ml of ethyl acetate and the resultant was washed with water to nutralized the same. The resultant was dried over anhydrous sodium sulfate and the solvent was evaporated under reduced pressure and the residue was purified by Lober column (commercially available from Merck Co., Inc., eluant; ethyl acetate:cyclohexane=1:2) to obtain 81 mg of the captioned compound.

IR (neat) $v$: 3370, 2985, 2950, 2930, 1720, 1595, 1415, 1380, 1305, 1285, 1250, 1180, 1130, 1100, 1080, 1025, 960, 900, 860 cm$^{-1}$ Mass (EI method, m/e): 426 (M+)

High resolution mass spectrum

Calcd. ($C_{26}H_{34}O_5$, M+): 426.2404

Found (M+): 426.2411

The same procedure as in Reference Example 4 except that 15-epi-11-dehydroxy-11-acetoxy-16-methyl-5,6,7-trinor-18,19-tetradehydro-4,8-inter-m-phenylene PGI$_2$ methyl ester, 15-epi-11-dehydroxy-11-propionyloxy-16-methyl-5,6,7-trinor-18,19-tetradehydro-4,8-inter-m-phenylene PGI$_2$ methyl ester, 15-epi-11-dehydroxy-11-butyroyloxy-16-methyl-5,6,7-trinor-18,19-tetradehydro-4,8-inter-m-phenylene PGI$_2$ methyl ester, 15-epi-11-dehydroxy-11-octanoyloxy-16-methyl-5,6,7-trinor-18,19-tetradehydro-4,8-inter-m-phenylene PGI$_2$ methyl ester, 15-epi-11-dehydroxy-11-decanoyloxy-16-methyl-5,6,7-trinor-18,19-tetradehydro-4,8-inter-m-phenylene PGI$_2$ methyl ester, 15-epi-11-dehydroxy-11-valeroyloxy-16-methyl-5,6,7-trinor-18,19-tetradehydro-4,8-inter-m-phenylene PGI$_2$ methyl ester, 15-epi-11-dehydroxy-11-benzoyloxy-16-methyl-5,6,7-trinor-18,19-tetradehydro-4,8-inter-m-phenylene PGI$_2$ methyl ester, 15-epi-11-dehydroxy-11-(α-naphthoyloxy)-16-methyl-5,6,7-trinor-18,19-tetradehydro-4,8-inter-m-phenylene PGI$_2$ methyl ester, 15-epi-11-dehydroxy-11-(β-naphthoyloxy)-16-methyl-5,6,7-trinor-18,19-tetradehydro-4,8-inter-m-phenylene PGI$_2$ methyl ester, 15-epi-11-dehydroxy-11-(m-toluoyloxy)-16-methyl-5,6,7-trinor-18,19-tetradehydro-4,8-inter-m-phenylene PGI$_2$ methyl ester, 15-epi-11-(o-toluoyloxy)-16-methyl-5,6,7-trinor-18,19-tetradehydro-4,8-inter-m-phenylene PGI$_2$ methyl ester or 15-epi-11-dehydroxy-11-(p-phenylbenzoyloxy)-16-methyl-5,6,7-trinor-18,19-tetradehydro-4,8-inter-m-phenylene PGI$_2$ methyl ester is employed in place of 15-epi-11-dehydroxy-11-(p-toluoyloxy)-16-methyl-5,6,7-trinor-18,19-tetradehydro-4,8-inter-m-phenylene PGI$_2$ methyl ester yields the captioned compound.

EXAMPLE 56

5,6,7-trinor-18,19-tetradehydro-4,8-inter-m-phenylene PGI$_2$ methyl ester (7)

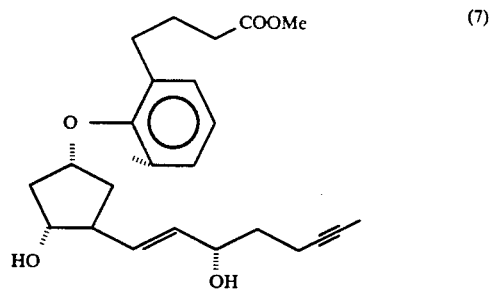

The same procedure as in Example 51 was repeated except that 128 mg of 15-epi-11-dehydroxy-11-(p-toluoyloxy)- 5,6,7-trinor-18,19-tetradehydro-4,8-inter-m-phenylene PGI$_2$ methyl ester was employed as a substrate to obtain 58 mg of the captioned compound.

IR (neat) $v$: 3370, 1740, 1595, 970, 745 cm$^{-1}$

NMR (CDCl$_3$, δ): 1.70 (3H, t, J=3.0 Hz), 1.20–2.80 (15H, m), 3.40 (1H, t, J=7.8 Hz), 3.59 (3H, s), 3.80 (1H, q, J=6.1 Hz), 4.50 (1H, m), 5.05 (1H, m), 5.60 (2H, m), 6.60–7.00 (3H, m)

Mass (EI method, m/e): 398 (M+)

High resolution mass spectrum

Calcd. ($C_{24}H_{30}O_5$, M+): 398.2352

Found (M ): 398.2358

The same procedure as in Example 56 except that 15-epi-11-dehydroxy-11-acetoxy-5,6,7-trinor-18,19-tetradehydro-4,8-inter-m-phenylene PGI$_2$ methyl ester, 15-epi-11-dehydroxy-11-propionyloxy-5,6,7-trinor-18,19-tetradehydro-4,8-inter-m-phenylene PGI$_2$ methyl ester, 15-epi-11-dehydroxy-11-butyroyloxy-5,6,7-trinor-18,19-tetradehydro-4,8-inter-m-phenylene PGI$_2$ methyl ester, 15-epi-11-dehydroxy-11-octanoyloxy-5,6,7-trinor-18,19-tetradehydro-4,8-inter-m-phenylene PGI$_2$ methyl ester, 15-epi-11-dehydroxy-11-decanoyloxy-5,6,7-trinor-18,19-tetradehydro-4,8-inter-m-phenylene PGI$_2$ methyl ester, 15-epi-11-dehydroxy-11-valeroyloxy-5,6,7-trinor-18,19-tetradehydro-4,8-inter-m-phenylene PGI$_2$ methyl ester, 15-epi- 11-dehydroxy-11-benzoyloxy-5,6,7-trinor-18,19-tetradehydro-4,8-inter-m-phenylene PGI$_2$ methyl ester, 15-epi-11-dehydroxy-11-(α-naphthoyloxy)-5,6,7-trinor-18,19-tetradehydro-4,8-inter-m-phenylene PGI$_2$ methyl ester, 15-epi-11-dehydroxy-11-(β-naphthoyloxy)-5,6,7-trinor-18,19-tetradehydro-4,8-inter-m-phenylene PGI$_2$ methyl ester, 15-epi-11-dehydroxy-11-(m-toluoyloxy)-5,6,7-trinor-18,19-tetradehydro-4,8-inter-m-phenylene PGI$_2$ methyl ester, 15-epi-11-dehydroxy-11-(o-toluoyloxy)-5,6,7-trinor-18,19-tetradehydro-4,8-inter-m-phenylene PGI$_2$ methyl ester or 15-epi-11-dehydroxy-11-(p-phenylbenzoyloxy)-5,6,7-trinor-18,19-tetradehydro-4,8-inter-m-phenylene PGI$_2$ methyl ester is employed in place of 15-epi-11-dehydroxy-11-(p-toluoyloxy)-5,6,7-trinor-18,19-tetradehydro-4,8-inter-m-phenylene PGI$_2$ methyl ester yields the captioned compound.

The same rpocedure as in Example 56 except that ethanol is employed as a solvent in place of methanol and except that 15-epi-11-dehydroxy-11-acetoxy-5,6,7-trinor-18,19-tetradehydro-4,8-inter-m-phenylene PGI$_2$ ethyl ester, 15-epi-11-dehydroxy-11-propionyloxy-5,6,7-trinor-18,19-tetradehydro-4,8-inter-m-phenylene PGI$_2$ ethyl ester, 15-epi-11-dehydroxy-11-butyroyloxy-5,6,7-trinor-18,19-tetradehydro-4,8-inter-m-phenylene PGI$_2$ ethyl ester, 15-epi-11-dehydroxy-11-octanoyloxy-5,6,7-trinor-18,19-tetradehydro-4,8-inter-m-phenylene PGI$_2$ ethyl ester, 15-epi-11-dehydroxy-11-decanoyloxy-5,6,7-trinor- 18,19-tetradehydro-4,8-inter-m-phenylene PGI$_2$ ethyl ester, 15-epi-11-dehydroxy-11-valeroyloxy-5,6,7-trinor-18,19-tetradehydro-4,8-inter-m-phenylene PGI$_2$ ethyl ester, 15-epi-11-dehydroxy-11-benzoyloxy-5,6,7-trinor-18,19-tetradehydro-4,8-inter-m-phenylene PGI$_2$ ethyl ester, 15-epi-11-dehydroxy-11-($\alpha$-naphthoyloxy)-5,6,7-trinor-18,19-tetradehydro-4,8-inter-m-phenylene PGI$_2$ ethyl ester, 15-epi-11-dehydroxy-11-($\beta$-naphthoyloxy)-5,6,7-trinor-18,19-tetradehydro-4,8-inter-m-phenylene PGI$_2$ ethyl ester, 15-epi-11-dehydroxy-11-(m-toluoyloxy)-5,6,7-trinor-18,19-tetradehydro-4,8-inter-m-phenylene PGI$_2$ ethyl ester, 15-epi-11-dehydroxy-11-(o-toluoyloxy)-5,6,7-trinor-18,19-tetradehydro-4,8-inter-m-phenylene PGI$_2$ ethyl ester or 15-epi-11-dehydroxy-11-(p-phenylbenzoyloxy)-5,6,7-trinor-18,19-tetradehydro-4,8-inter-m-phenylene PGI$_2$ ethyl ester is employed in place of 15-epi-11-dehydroxy-11-(p-toluoyloxy)-5,6,7-trinor-18,19-tetradehydro-4,8-inter-m-phenylene PGI$_2$ methyl ester yields 5,6,7-trinor-18,19-tetradehydro-4,8-inter-m-phenylene PGI$_2$ ethyl ester. The same procedure as in Example 56 except that 15-epi-11-dehydroxy-11-(p-toluoyloxy)-2,5,6,7-tetranor-4-oxa-18,19-tetradehydro-4,8-inter-m-phenylene PGI$_2$ methyl ester, 15-epi-11-dehydroxy-11-acetoxy-2,5,6,7-tetranor-4-oxa-18,19-tetradehydro-4,8-inter-m-phenylene PGI$_2$ methyl ester, 15-epi-11-dehydroxy-11-propionyloxy-2,5,6,7-tetranor-4-oxa-18,19-tetradehydro-4,8-inter-m-phenylene PGI$_2$ methyl ester, 15-epi-11-dehydroxy-11-butyroyloxy-2,5,6,7-tetranor-4-oxa-18,19-tetradehydro-4,8-inter-m-phenylene PGI$_2$ methyl ester, 15-epi-11-dehydroxy-11-octanoyloxy-2,5,6,7-tetranor-4-oxa-18,19-tetradehydro-4,8-inter-m-phenylene PGI$_2$ methyl ester, 15-epi-11-dehydroxy-11-decanoyloxy-2,5,6,7-tetranor-4-oxa-18,19-tetradehydro-4,8-inter-m-phenylene PGI$_2$ methyl ester, 15-epi-11-dehydroxy-11-valeroyloxy-2,5,6,7-tetranor-4-oxa-18,19-tetradehydro-4,8-inter-m-phenylene PGI$_2$ methyl ester, 15-epi-11-dehydroxy-11-benzoyloxy-2,5,6,7-tetranor-4-oxa-18,19-tetradehydro-4,8-inter-m-phenylene PGI$_2$ methyl ester, 15-epi-11-dehydroxy-11-($\alpha$-naphthoyloxy)-2,5,6,7-tetranor-4-oxa-18,19-tetradehydro-4,8-inter-m-phenylene PGI$_2$ methyl ester, 15-epi-11dehydroxy-11-($\beta$-naphthoyl)-2,5,6,7-tetranoroxy-4-oxa-18,19-tetradehydro-4,8-inter-m-phenylene PGI$_2$ methyl ester, 15-epi-11-dehydroxy-11-(m-toluoyloxy)-2,5,6,7-tetranor-4-oxa-18,19-tetradehydro-4,8-inter-m-phenylene PGI$_2$ methyl ester, 15-epi-11-dehydroxy-11-(o-toluoyloxy)-2,5,6,7-tetranor-4-oxa-18,19-tetradehydro-4,8-inter-m-phenylene PGI$_2$ methyl ester or 15-epi-11-dehydroxy-11-(p-phenylbenzoyloxy)-2,5,6,7-tetranor-4-oxa-18,19-tetradehydro-4,8-inter-m-phenylene PGI$_2$ methyl ester is employed in place of 15-epi-11-dehydroxy-11-(p-toluoyloxy)-5,6,7-trinor-18,19-tetradehydro-4,8-inter-m-phenylene PGI$_2$ methyl ester yields 2,5,6,7-tetranor-4-oxa-18,19-tetradehydro-4,8-inter-m-phenylene PGI$_2$ methyl ester. The same procedure as in Example 56 except that 15-epi-11-dehydroxy-11-(p-toluoyloxy)-2,5,6,7-tetranor-18,19-tetradehydro-4,8-inter-m-phenylene PGI$_2$ methyl ester, 15-epi-11-dehydroxy-11-acetoxy-2,5,6,7-tetranor-18,19-tetradehydro-4,8-inter-m-phenylene PGI$_2$ methyl ester, 15-epi-11-dehydroxy-11-propionyloxy-2,5,6,7-tetranor-18,19-tetradehydro-4,8-inter-m-phenylene PGI$_2$ methyl ester, 15-epi-11-dehydroxy-11-butyroyloxy-2,5,6,7-tetranor-18,19-tetradehydro-4,8-inter-m-phenylene PGI$_2$ methyl ester, 15-epi-11-dehydroxy-11-octanoyloxy-2,5,6,7-tetranor-18,19-tetradehydro-4,8-inter-m-phenylene PGI$_2$ methyl ester, 15-epi-11-dehydroxy-11-decanoyloxy-2,5,6,7-tetranor-18,19-tetradehydro-4,8-inter-m-phenylene PGI$_2$ methyl ester, 15-epi-11-dehydroxy-11-valeroyloxy-2,5,6,7-tetranor-18,19-tetradehydro-4,8-inter-m-phenylene PGI$_2$ methyl ester, 15-epi-11-dehydroxy-11-benzoyloxy-2,5,6,7-tetradehydro-4,8-inter-m-phenylene PGI$_2$ methyl ester, 15-epi-11-dehydroxy-11-($\alpha$-naphthoyloxy)-2,5,6,7-tetranor-18,19-tetradehydro-4,8-inter-m-phenylene PGI$_2$ methyl ester, 15-epi-11-dehydroxy-11-($\beta$-naphthoyloxy)-2,5,6,7-tetranor-18,19-tetradehydro-4,8-inter-m-phenylene PGI$_2$ methyl ester, 15-epi-11-dehydroxy-11-(m-toluoyloxy)-2,5,6,7-tetranor-18,19-tetradehydro-4,8-inter-m-phenylene PGI$_2$ methyl ester, 15-epi-11-dehydroxy-11-(o-toluoyloxy)-2,5,6,7-tetranor-18,19-tetradehydro-4,8-inter-m-phenylene PGI$_2$ methyl ester or 15-epi-11-dehydroxy-11-(p-phenylbenzoyloxy)- 2,5,6,7-tetranor-18,19-tetradehydro-4,8-inter-m-phenylene PGI$_2$ methyl ester is employed in place of 15-epi-11-dehydroxy-11-(p-toluoyloxy)-5,6,7-trinor-18,19-tetradehydro-4,8-inter-m-phenylene PGI$_2$ methyl ester yields 2,5,6,7-tetranor-18,19-tetradehydro-4,8-inter-m-phenylene PGI$_2$ methyl ester. The same procedure as in Example 56 except that 15-epi-11-dehydroxy-11-(p-toluoyloxy)-2,5,6,7-tetranor-4-oxa-18,19-tetradehydro-4,8-inter-m-phenylene PGI$_2$ ethyl ester, 15-epi-11-dehydroxy-11-acetoxy-2,5,6,7-tetranor-4-oxa-18,19-tetradehydro-4,8-inter-m-phenylene PGI$_2$ ethyl ester, 15-epi-11-dehydroxy-11-propionyloxy-2,5,6,7-tetranor-4-oxa-18,19-tetradehydro-4,8-inter-m-phenylene PGI$_2$ ethyl ester, 15-epi-11-dehydroxy-11-butyroyloxy-2,5,6,7-tetranor-4-oxa-18,19-tetradehydro-4,8-inter-m-phenylene PGI$_2$ ethyl ester, 15-epi-11-dehydroxy-11-octanoyloxy-2,5,6,7-tetranor-4-oxa-18,19-tetradehydro-4,8-inter-m-phenylene PGI$_2$ ethyl ester, 15-epi-11-dehydroxy-11-decanoyloxy-2,5,6,7-tetranor-4-oxa-18,19-tetradehydro-4,8-inter-m-phenylene PGI$_2$ ethyl ester, 15-epi-11-dehydroxy-11-valeroyloxy-2,5,6,7-tetranor-4-oxa-18,19-tetradehydro-4,8-inter-m-phenylene PGI$_2$ methyl ester, 15-epi-11-dehydroxy-11-benzoyloxy-2,5,6,7-tetranor-4-oxa-18,19-tetradehydro-4,8-inter-m-phenylene PGI$_2$ethyl ester, 15-epi-11-dehydroxy-11-($\alpha$-naphthoyloxy)-2,5,6,7-tetranor-4-oxa-18,19-tetradehydro-4,8-inter-m-phenylene PGI$_2$ ethyl ester, 15-epi-11-dehydroxy- 11-($\beta$-naphthoyloxy)-2,5,6,7-tetranor-4-oxa-18,19-tetradehydro-4,8-inter-m-phenylene PGI$_2$ ethyl ester, 15-epi-11-dehydroxy-11-(m-toluoyloxy)-2,5,6,7-tetranor-4-oxa-18,19-tetradehydro-4,8-inter-m-phenylene PGI$_2$ ethyl ester, 15-epi-11-dehydroxy-11-(o-toluoyloxy)-2,5,6,7-tetranor-4-oxa-18,19-tetradehydro-4,8-inter-m-phenylene PGI$_2$ ethyl ester or 15-epi-11-dehydroxy-11-(p-phenylbenzoyloxy)-2,5,6,7-tetranor-4-oxa-18,19-tetradehydro-4,8-inter-m-phenylene PGI$_2$ ethyl ester is employed in place of 15-epi-11-dehydroxy-11-(p-toluoyloxy)-5,6,7-trinor-18,19-tetradehydro-4,8-inter-m-phenylene PGI$_2$ methyl ester yields 2,5,6,7-tetranor-4-oxa-18,19-tetradehydro-4,8-inter-m-phenylene PGI$_2$ ethyl ester. The same procedure as in Example 56 except that 15-epi-11-dehydroxy-11-(p-toluoyloxy)-2,5,6,7-tetranor-18,19-tetradehydro-4,8-inter-m-phenylene PGI$_2$ ethyl ester, 15-epi-11-dehydroxy-11-acetoxy-2,5,6,7-tetranor-18,19-tetradehydro-4,8-inter-m-phenylene PGI$_2$ ethyl ester, 15-epi-11-dehydroxy-11-propionyloxy-2,5,6,7-tetranor-18,19-tetradehydro-4,8- inter-m-phenylene PGI$_2$ ethyl ester, 15-epi-11-dehydroxy-11-butyroyloxy-2,5,6,7-tetranor-18,19-tetradehydro-4,8-inter-m-phenylene PGI$_2$ ethyl ester, 15-epi-11-dehydroxy-11-octanoyloxy-2,5,6,7-tetranor-18,19-tetradehydro-4,8-inter-m-phenylene PGI$_2$ ethyl ester, 15-epi-11-dehydroxy-11-decanoyloxy-2,5,6,7-tetranor-18,19-tetradehydro-4,8-inter-m-phenylene PGI$_2$ ethyl ester, 15-epi-11-dehydroxy-11-valeroyloxy- 2,5,6,7-tetranor-18,19-tetradehydro-4,8-inter-m-phenylene PGI$_2$ ethyl ester, 15-epi-11-dehydroxy-11-benzoyloxy-2,5,6,7-tetranor-18,19-tetradehydro-4,8-inter-m-phenylene PGI$_2$ ethyl ester, 15-epi-11-dehydroxy-11-($\alpha$-naphthoyloxy)-2,5,6,7-tetranor-18,19-tetradehydro-4,8-inter-m-phenylene PGI$_2$ ethyl ester, 15-epi-11-dehydroxy-11-($\beta$-naphthoyloxy)-2,5,6,7-tetranor-18,19-tetradehydro-4,8-inter-m-phenylene PGI$_2$ ethyl ester, 15-epi-11-dehydroxy-11-(m-toluoyloxy)-2,5,6,7-tetranor-18,19-tetradehydro-4,8-inter-m-phenylene PGI$_2$ ethyl ester, 15-epi-11-dehydroxy-11-(o-toluoyloxy)-2,5,6,7-tetranor-18,19-tetradehydro-4,8-inter-m-phenylene PGI$_2$ ethyl ester or 15-epi-11-dehydroxy-11-(p-phenylbenzoyloxy)-2,5,6,7-tetranor-18,19-tetradehydro-4,8-inter-m-phenylene PGI$_2$ ethyl ester is employed in place of 15-epi-11-dehydroxy-11-(p-toluoyloxy)-5,6,7-trinor-18,19-tetradehydro-4,8-inter-m-phenylene PGI$_2$ methyl ester yields 2,5,6,7-tetranor-18,19-tetradehydro-4,8-inter-m-phenylene PGI$_2$ ethyl ester.

EXAMPLE 57

16-methyl-5,6,7-trinor-18,19-tetradehydro-4,8-inter-m-phenylene PGI$_2$ (8)

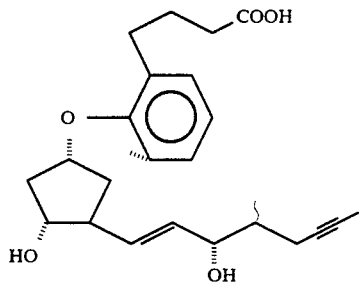

(8)

In 3 ml of anhydrous THF, 226 mg (0.548 mmol) of 15-epi-11-dehydroxy-11-(p-toluoyloxy)-16-methyl-5,6,7-trinor-18,19-tetradehydro-4,8-inter-m-phenylene PGI$_2$ methyl ester was dissolved and then 287 mg (1.09 mmol) of triphenylphosphine and 144 mg (1.18 mmol) of benzoic acid were added thereto and the resulting mixture was stirred at room temperature. To the thus obtained reaction mixture, 245 mg (1.19 mmol) of diethylazodicarborate in 6 ml of anhydrous THF was added for 5 minutes, followed by being stirred for 2 hours at room temperature. The solvent was evapolated under reduced pressure and the residue was dissolved in 10 ml of methanol and 3 ml of 1.02N of aqueous sodium hydroxide solution was added thereto, followed by being stirred for 17 hours at room temeperarure. The solvent was evapolated under reduced pressure and the residue was dissolved in 10 ml of ethyl acetate and the resultant was washed with water to nutralize the same. The resultant was dried over anhydrous sodium sulfate and the solvent was evapolated under reduced pressure and the residue was purified by Lober column (commercially available from Merck Co., Inc. (which was inactivated using saturated aqueous ethyl acetate solution, eluant; ethyl acetate:cyclohexane=1:4) to obtain 156 mg of the captioned compound.

IR (neat) $\nu$: 3700–2200, 1710, 1595, 1455, 1415, 1380, 1360, 1340, 1305, 1285, 1250, 1180, 1130, 1100, 1080, 1025, 1010, 975, 900, 860, 740 cm$^{-1}$ NMR (CDCl$_3$, $\delta$): 1.65 (3H, t, J=8.0 Hz), 1.40–2.80 (14H, m), 3.80 (1H, m), 4.20 (1H, m), 5.00 (1H, m), 5.10–5.80 (4H, m), 6.50–7.00 (3H, m)

Mass (EI method, m/e): 398 (M+)

High resolution mass spectrum

Calcd. (C$_{24}$H$_{30}$O$_5$, M+): 398.2352

Found (M+): 398.2356

The same procedure as in Example 57 except that 15-epi-11-dehydroxy-11-acetoxy-16-methyl-5,6,7-trinor-18,19-tetradehydro-4,8-inter-m-phenylene PGI$_2$ methyl ester, 15-epi-11-dehydroxy-11-propionyloxy-16-methyl-5,6,7-trinor-18,19-tetradehydro-4,8-inter-m-phenylene PGI$_2$ methyl ester, 15-epi-11-dehydroxy-11-butyroyloxy-16-methyl-5,6,7-trinor-18,19-tetradehydro-4,8-inter-m-phenylene PGI$_2$ methyl ester, 15-epi-11-dehydroxy-11-octanoyloxy-16-methyl-5,6,7-trinor-18,19-tetradehydro-4,8-inter-m-phenylene PGI$_2$ methyl ester, 15-epi-11-dehydroxy-11-decanoyloxy-16-methyl-5,6,7-trinor-18,19-tetradehydro-4,8-inter-m-phenylene PGI$_2$ methyl ester, 15-epi-11-dehydroxy-11-valeroyloxy-16-methyl-5,6,7-trinor-18,19-tetradehydro-4,8-inter-m-phenylene PGI$_2$ methyl ester, 15-epi-11-dehydroxy-11-benzoyloxy-16-methyl-5,6,7-trinor-18,19-tetradehydro-4,8-inter-m-phenylene PGI$_2$ methyl ester, 15-epi-11-dehydroxy-11-($\alpha$-naphthoyloxy)-16-methyl-5,6,7-trinor-18,19-tetradehydro-4,8-inter-m-phenyl-PGI$_2$ methyl ester, 15-epi-11-dehydroxy-11-($\beta$-naphthoyloxy)-16-methyl-5,6,7-trinor-18,19-tetradehydro-4,8-inter-m-phenylene PGI$_2$ methyl ester, 15-epi-11-dehydroxy-11-(m-toluoyloxy)-16-methyl-5,6,7-trinor-18,19-tetradehydro-4,8-inter-m-phenylene PGI$_2$ methyl ester, 15-epi-11-dehydroxy-11-(o-toluoyloxy)-16-methyl-5,6,7-trinor-18,19-tetradehydro-4,8-inter-m-phenylene PGI$_2$ methyl ester or 15-epi-11-dehydroxy-11-(p-phenylbenzoyloxy)-16-methyl-5,6,7-trinor-18,19-tetradehydro-4,8-inter-m-phenylene PGI$_2$ methyl ester is employed in place of 15-epi-11-dehydroxy-11-(p-toluoyloxy)-16-methyl-5,6,7-trinor-18,19-tetradehydro-4,8-inter-m-phenylene PGI$_2$ methyl ester yields the captioned compound.

The same procedure as in Example 57 except that 15-epi-11-dehydroxy-11-(p-toluoyloxy)-2,5,6,7-tetranor-4-oxa-18,19-tetradehydro-4,8-inter-m-phenylene PGI$_2$ methyl ester, 15-epi-11-dehydroxy-11-acetoxy-2,5,6,7-tetranor-4-oxa-18,19-tetradehydro-4,8-inter-m-phenylene PGI$_2$ methyl ester, 15-epi-11-dehydroxy-11-propionyloxy-2,5,6,7-tetranor-4-oxa-18,19-tetradehydro-4,8-inter-m-phenylene PGI$_2$ methyl ester, 15-epi-11-dehydroxy-11-butyroyloxy-2,5,6,7-tetranor-4-oxa-18,19-tetradehydro-4,8-inter-m-phenylene PGI$_2$ methyl ester, 15-epi-11-dehydroxy-11-octanoyloxy-2,5,6,7-tetranor-4-oxa-18,19-tetradehydro-4,8-inter-m-phenylene PGI$_2$ methyl ester, 15-epi- 11-dehydroxy-11-decanoyloxy-2,5,6,7-tetranor-4-oxa-18,19-tetradehydro-4,8-inter-m-phenylene PGI$_2$ methyl ester, 15-epi-11-dehydroxy-11-valeroyloxy-2,5,6,7-tetranor-4-oxa-18,19-tetradehydro-4,8-inter-m-phenylene PGI$_2$ methyl ester, 15-epi-11-dehydroxy-11-benzoyloxy-2,5,6,7-tetranor-4-oxa-18,19-tetradehydro-4,8-inter-m-phenylene PGI$_2$ methyl ester, 15-epi-11-dehydroxy-11-($\alpha$-naphthoyloxy)-2,5,6,7-tetranor-4-oxa-18,19-tetradehydro-4,8-inter-m-phenylene PGI$_2$ methyl ester, 15-epi-11-dehydroxy-11-($\beta$-naphthoyloxy)-2,5,6,7-tetranor-4- oxa-18,19-tetradehydro-4,8-inter-m-phenylene PGI₂ methyl ester, 15-epi-11-dehydroxy-11-(m-toluoyloxy)-2,5,6,7-tetranor-4-oxa-18,19-tetradehydro-4,8-inter-m-phenylene PGI₂ methyl ester, 15-epi-11-dehydroxy-11-(o-toluoyloxy)-2,5,6,7-tetranor-4-oxa-18,19-tetradehydro-4,8-inter-m-phenylene PGI₂ methyl ester or 15-epi-11-dehydroxy-11-(p-phenylbenzoyloxy)-2,5,6,7-tetranor-4-oxa-18,19-tetradehydro-4,8-inter-m-phenylene PGI₂ methyl ester is employed in place of 15-epi-11-dehydroxy-11-(p-toluoyloxy)-16-methyl-5,6,7-trinor-18,19-tetradehydro-4,8-inter-m-phenylene PGI₂ methyl ester yields 5,6,7-tetranor-4-oxa-18,19-tetradehydro-4,8-inter-m-phenylene PGI₂.

The same procedure as in Example 57 except that 15-epi-11-dehydroxy-11-(p-toluoyloxy)-2,5,6,7-tetranor-18,19-tetradehydro-4,8-inter-m-phenylene PGI₂ methyl ester, 15-epi-11-dehydroxy-11-acetoxy-2,5,6,7-tetranor-18,19-tetradehydro-4,8-inter-m-phenylene PGI₂ methyl ester, 15-epi-11-dehydroxy-11-propionyloxy-2,5,6,7-tetranor-18,19-tetradehydro-4,8-inter-m-phenylene PGI₂ methyl ester, 15-epi-11-dehydroxy-11-butyroyloxy-2,5,6,7-tetranor-18,19-tetradehydro-4,8-inter-m-phenylene PGI₂ methyl ester, 15-epi-11-dehydroxy-11-octanoyloxy-2,5,6,7-tetranor-18,19-tetradehydro-4,8-inter-m-phenylene PGI₂ methyl ester, 15-epi-11-dehydroxy-11-decanoyloxy-2,5,6,7-tetranor-18,19-tetradehydro-4,8-inter-m-phenylene PGI₂ methyl ester, 15-epi-11-dehydroxy-11-valeroyloxy-2,5,6,7-tetranor-18,19-tetradehydro-4,8-inter-m-phenylene PGI₂ methyl ester, 15-epi-11-dehydroxy-11-benzoyloxy-2,5,6,7-tetranor-18,19-tetradehydro-4,8-inter-m-phenylene PGI₂ methyl ester, 15-epi-11-dehydroxy-11-(α-naphthoyloxy)-2,5,6,7-tetranor-18,19-tetradehydro-4,8-inter-m-phenylene PGI₂ methyl ester, 15-epi-11-dehydroxy-11-(β-naphthoyloxy)-2,5,6,7-tetranor-18,19-tetradehydro-4,8-inter-m-phenylene PGI₂ methyl ester, 15-epi-11-dehydroxy-11-(m-toluoyloxy)-2,5,6,7-tetranor-18,19-tetradehydro-4,8-inter-m-phenylene PGI₂ methyl ester, 15-epi-11-dehydroxy-11-(o-toluoyloxy)-2,5,6,7-tetranor-18,19-tetradehydro-4,8-inter-m-phenylene PGI₂ methyl ester or 15-epi-11-dehydroxy-11-(p-phenylbenzoyloxy)-2,5,6,7-tetranor-18,19-tetradehydro-4,8-inter-m-phenylene PGI₂ methyl ester is employed in place of 15-epi-11-dehydroxy-11-(p-toluoyloxy)-16-methyl-5,6,7-trinor-18,19-tetradehydro-4,8-inter-m-phenylene PGI₂ methyl ester yields 2,5,6,7-tetranor-18,19-tetradehydro-4,8-inter-m-phenylene PGI₂. The same procedure as in Example 57 except that 15-epi-11-dehydroxy-11-acetoxy-16-methyl-20-homo-5,6,7-trinor-18,19-tetradehydro-4,8-inter-m-phenylene PGI₂ methyl ester, 15-epi-11-dehydroxy-11-propionyloxy-16-methyl-20-homo-5,6,7-trinor-18,19-tetradehydro-4,8-inter-m-phenylene PGI₂ methyl ester, 15-epi-11-dehydroxy-11-butyroyloxy-16-methyl-20-homo-5,6,7-trinor-18,19-tetradehydro-4,8-inter-m-phenylene PGI₂ methyl ester, 15-epi-11-dehydroxy-11-octanoyloxy-16-methyl-20-homo-5,6,7-trinor-18,19-tetradehydro-4,8-inter-m-phenylene PGI₂ methyl ester, 15-epi-11-dehydroxy-11-decanoyloxy-16-methyl-20-homo-5,6,7-trinor-18,19-tetradehydro-4,8-inter-m-phenylene PGI₂ methyl ester, 15-epi-11-dehydroxy-11-valeroyloxy-16-methyl-20-homo-5,6,7-trinor-18,19-tetradehydro-4,8-inter-m-phenylene PGI₂ methyl ester, 15-epi-11-dehydroxy-11-benzoyloxy-16-methyl-20-homo-5,6,7-trinor-18,19-tetradehydro-4,8-inter-m-phenylene PGI₂ methyl ester, 15-epi-11-dehydroxy-11-(α-naphthoyloxy)-16-methyl-20-homo-5,6,7-trinor-18,19-tetradehydro-4,8-inter-m-phenylene PGI₂ methyl ester, 15-epi-11-dehydroxy-11-(β-naphthoyloxy)-16-methyl-20-homo-5,6,7-trinor-18,19-tetradehydro-4,8-inter-m-phenylene PGI₂ methyl ester, 15-epi-11-dehydroxy-11-(m-toluoyloxy)-16-methyl-20-homo-5,6,7-trinor-18,19-tetradehydro-4,8-inter-m-phenylene PGI₂ methyl ester, 15-epi-11-dehydroxy-11-(o-toluoyloxy)-16-methyl-20-homo-5,6,7-trinor-18,19-tetradehydro-4,8-inter-m-phenylene PGI₂ methyl ester or 15-epi-11-hydroxy-11-(p-phenylbenzoyloxy)-16-methyl-20-homo-5,6,7-trinor-18,19-tetradehydro-4,8-inter-m-phenylene PGI₂ methyl ester is employed in place of 15-epi-11-dehydroxy-11-(p-toluoyloxy)-16-methyl-5,6,7-trinor-18,19-tetradehydro-4,8-inter-m-phenylene PGI₂ methyl ester yields 16-methyl-20-homo-5,6,7-trinor-18,19-tetradehydro-4,8-inter-m-phenylene PGI₂. The same procedure as in Example 57 except that 15-epi-11-dehydroxy-11-(p-toluoyloxy)-16-methyl-20-homo-2,5,6,7-tetranor-4-oxa-18,19-tetradehydro-4,8-inter-m-phenylene PGI₂ methyl ester, 15-epi-11-dehydroxy-11-acetoxy-16-methyl-20-homo-2,5,6,7-tetranor-4-oxa-18,19-tetradehydro-4,8-inter-m-phenylene PGI₂ methyl ester, 15-epi-11-dehydroxy-11-propionyloxy-16-methyl-20-homo-2,5,6,7-tetranor-4-oxa-18,19-tetradehydro-4,8-inter-m-phenylene PGI₂ methyl ester, 15-epi-11-dehydroxy-11-butyroyloxy-16-methyl-20-homo-2,5,6,7-tetranor-4-oxa-18,19-tetradehydro-4,8-inter-m-phenylene PGI₂ methyl ester, 15-epi-11-dehydroxy-11-octanoyloxy-16-methyl-20-homo-2,5,6,7-tetranor-4-oxa-18,19-tetradehydro-4,8-inter-m-phenylene PGI₂ methyl ester, 15-epi-11-dehydroxy-11-decanoyloxy-16-methyl-20-homo-2,5,6,7-tetranor-4-oxa-18,19-tetradehydro-4,8-inter-m-phenylene PGI₂ methyl ester, 15-epi-11-dehydroxy-11-valeroyloxy-16-methyl-20-homo-2,5,6,7-tetranor-4-oxa-18,19-tetradehydro-4,8-inter-m-phenylene PGI₂ methyl ester, 15-epi-11-dehydroxy-11-benzoyloxy-16-methyl-20-homo-2,5,6,7-tetranor-4-oxa-18,19-tetradehydro-4,8-inter-m-phenylene PGI₂ methyl ester, 15-epi-11-dehydroxy-11-(α-naphthoyloxy)-16-methyl-20-homo-2,5,6,7-tetranor-4-oxa-18,19-tetradehydro-4,8-inter-m-phenylene PGI₂ methyl ester, 15-epi-11-dehydroxy-11-(β-naphthoyl)-16-methyl-20-homo-2,5,6,7-tetranoloxy-4-oxa-18,19-tetradehydro-4,8-inter-m-phenylene PGI₂ methyl ester, 15-epi-11-dehydroxy-11-(m-toluoyloxy)-16-methyl-20-homo-2,5,6,7-tetranor-4-oxa-18,19-tetradehydro-4,8-inter-m-phenylene PGI₂ methyl ester, 15-epi-11-dehydroxy-11-(o-toluoyloxy)-16-methyl-20-homo-2,5,6,7-tetranor-4-oxa-18,19-tetradehydro-4,8-inter-m-phenylene PGI₂ methyl ester or 15-epi-11-dehydroxy-11-(p-phenylbenzoyloxy)-16-methyl-20-homo-2,5,6,7-tetranor-4-oxa-18,19-tetradehydro-4,8-inter-m-phenylene PGI₂ methyl ester is employed in place of 15-epi-11-dehydroxy-11-(p-toluoyloxy)-16-methyl-5,6,7-trinor-18,19-tetradehydro-4,8-inter-m-phenylene PGI₂ methyl ester yields 16-methyl-20-homo-2,5,6,7-tetranor-4-oxa-18,19-tetradehydro-4,8-inter-m-phenylene PGI₂. The same procedure as in Example 57 except that 15-epi-11-dehydroxy-11-(p-toluoyloxy)-16-methyl-20-homo-2,5,6,7-tetranor-18,19-tetradehydro-4,8-inter-m-phenylene PGI₂ methyl ester, 15-epi-11-dehydroxy-11-acetoxy-16-methyl-20-homo-2,5,6,7-tetranor-18,19-tetradehydro-4,8-inter-m-phenylene PGI₂ methyl ester, 15-epi-11-dehydroxy-11-propionyloxy-16-methyl-20-homo-2,5,6,7-tetranor-18,19-tetradehydro-4,8-inter-m-phenylene PGI₂ methyl ester, 15-epi-11-dehydroxy-11-butyroyloxy-16-methyl-20-homo-2,5,6,7-tetranor-18,19-tetradehydro-4,8-inter-m-phenylene PGI₂ methyl ester, 15-epi-11-dehydroxy-11-octanoyloxy-16-methyl-20- homo-2,5,6,7-tetranor-18,19-tetradehydro-4,8-inter-m-phenylene PGI$_2$ methyl ester, 15-epi-11-dehydroxy-11-decanoyloxy-16-methyl-20-homo-2,5,6,7-tetranor-18,19-tetradehydro-4,8-inter-m-phenylene PGI$_2$ methyl ester, 15-epi-11-dehydroxy-11-valeroyloxy-16-methyl-20-homo-2,5,6,7-tetranor-18,19-tetradehydro-4,8-inter-m-phenylene PGI$_2$ methyl ester, 15-epi-11-dehydroxy-11-benzoyloxy-16-methyl-20-homo-2,5,6,7-tetranor-18,19-tetradehydro-4,8-inter-m-phenylene PGI$_2$ methyl ester, 15-epi-11-dehydroxy-11-($\alpha$-naphthoyloxy)-16-methyl-20-homo-2,5,6,7-tetranor-18,19-tetradehydro-4,8-inter-m-phenylene PGI$_2$ methyl ester, 15-epi-11-dehydroxy-11-($\beta$-naphthoyloxy)-16-methyl-20-homo-2,5,6,7-tetranor-18,19-tetradehydro-4,8-inter-m-phenylene PGI$_2$ methyl ester, 15-epi-11-dehydroxy-11-(m-toluoyloxy)-16-methyl-20-homo-2,5,6,7-tetranor-18,19-tetradehydro-4,8-inter-m-phenylene PGI$_2$ methyl ester, 15-epi-11-dehydroxy-11-(o-toluoyloxy)-16-methyl-20-homo-2,5,6,7-tetranor-18,19-tetradehydro-4,8-inter-m-phenylene PGI$_2$ methyl ester or 15-epi-11-dehydroxy-11-(p-phenylbenzoyloxy)-16-methyl-20-homo-2,5,6,7-tetranor-18,19-tetradehydro-4,8-inter-m-phenylene PGI$_2$ methyl ester is employed in place of 15-epi-11-dehydroxy-11-(p-toluoyloxy)-16-methyl-5,6,7-trinor-18,19-tetradehydro-4,8-inter-m-phenylene PGI$_2$ methyl ester yields 16-methyl-20-homo-2,5,6,7-tetranor-18,19-tetradehydro-4,8-inter-m-phenylene PGI$_2$. The same procedure as in Example 57 except that 15-epi-11-dehydroxy-11-acetoxy-5,6,7-trinor-18,19-tetradehydro-4,8-inter-m-phenylene PGI$_2$ methyl ester, 15-epi-11-dehydroxy-11-propionyloxy-5,6,7-trinor-18,19-tetradehydro-4,8-inter-m-phenylene PGI$_2$ methyl ester, 15-epi-11-dehydroxy-11-butyroyloxy-5,6,7-trinor-18,19-tetradehydro-4,8-inter-m-phenylene PGI$_2$ methyl ester, 15-epi-11-dehydroxy-11-octanoyloxy-5,6,7-trinor-18,19-tetradehydro-4,8-inter-m-phenylene PGI$_2$ methyl ester, 15-epi-11-dehydroxy-11-decanoyloxy-5,6,7-trinor-18,19-tetradehydro-4,8-inter-m-phenylene PGI$_2$ methyl ester, 15-epi-11-dehydroxy-11-valeroyloxy-5,6,7-trinor-18,19-tetradehydro-4,8-inter-m-phenylene PGI$_2$ methyl ester, 15-epi-11-dehydroxy-11-benzoyloxy-5,6,7-trinor-18,19-tetradehydro-4,8-inter-m-phenylene PGI$_2$ methyl ester, 15-epi-11-dehydroxy-11-($\alpha$-naphthoyloxy)-5,6,7-trinor-18,19-tetradehydro-4,8-inter-m-phenylene PGI$_2$ methyl ester, 15-epi-11-dehydroxy-11-($\beta$-naphthoyloxy)-5,6,7-trinor-18,19-tetradehydro-4,8-inter-m-phenylene PGI$_2$ methyl ester, 15-epi-11-dehydroxy-11-(m-toluoyloxy)-5,6,7-trinor-18,19-tetradehydro-4,8-inter-m-phenylene PGI$_2$ methyl ester, 15-epi-11-dehydroxy-11-(o-toluoyloxy)-5,6,7-trinor-18,19-tetradehydro-4,8-inter-m-phenylene PGI$_2$ methyl ester or 15-epi-11-dehydroxy-11-(p-phenylbenzoyloxy)-5,6,7-trinor-18,19-tetradehydro-4,8-inter-m-phenylene PGI$_2$ methyl ester is employed in place of 15-epi-11-dehydroxy-11-(p-toluoyloxy)-16-methyl-5,6,7-trinor-18,19-tetradehydro-4,8-inter-m-phenylene PGI$_2$ methyl ester yields 5,6,7-trinor-18,19-tetradehydro-4,8-inter-m-phenylene PGI$_2$. The same procedure as in Example 57 except that 15-epi-11-dehydroxy-11-(p-toluoyloxy)-16-methyl-2,5,6,7-tetranor-4-oxa-18,19-tetradehydro-4,8-inter-m-phenylene PGI$_2$ methyl ester, 15-epi-11-dehydroxy-11-acetoxy-16-methyl-2,5,6,7-tetranor-4-oxa-18,19-tetradehydro-4,8-inter-m-phenylene PGI$_2$ methyl ester, 15-epi-11-dehydroxy-11-propionyloxy-16-methyl-2,5,6,7-tetranor-4-oxa-18,19-tetradehydro-4,8-inter-m-phenylene PGI$_2$ methyl ester, 15-epi-11-dehydroxy-11-butyroyloxy-16-methyl-2,5,6,7-tetranor-4-oxa-18,19-tetradehydro-4,8-inter-m-phenylene PGI$_2$ methyl ester, 15-epi-11-dehydroxy-11-octanoyloxy-16-methyl-2,5,6,7-tetranor-4-oxa-18,19-tetradehydro-4,8-inter-m-phenylene PGI$_2$ methyl ester, 15-epi-11-dehydroxy-11-decanoyloxy-16-methyl-2,5,6,7-tetranor-4-oxa-18,19-tetradehydro-4,8-inter-m-phenylene PGI$_2$ methyl ester, 15-epi-11-dehydroxy-11-valeroyloxy-16-methyl-2,5,6,7-tetranor-4-oxa-18,19-tetradehydro-4,8-inter-m-phenylene PGI$_2$ methyl ester, 15-epi-11-dehydroxy-11-benzoyloxy-16-methyl-2,5,6,7-tetranor-4-oxa-18,19-tetradehydro-4,8-inter-m-phenylene PGI$_2$ methyl ester, 15-epi-11-dehydroxy-11-($\alpha$-naphthoyloxy)-16-methyl-2,5,6,7-tetranor-4-oxa-18,19-tetradehydro-4,8-inter-m-phenylene PGI$_2$ methyl ester, 15-epi-11-dehydroxy-11-($\beta$-naphthoyloxy)-16-methyl-2,5,6,7-tetranor-4-oxa-18,19-tetradehydro-4,8-inter-m-phenylene PGI$_2$ methyl ester, 15-epi-11-dehydroxy-11-(m-toluoyloxy)-16-methyl-2,5,6,7-tetranor-4-oxa-18,19-tetradehydro-4,8-inter-m-phenylene PGI$_2$ methyl ester, 15-epi-11-dehydroxy-11-(o-toluoyloxy)-16-methyl-2,5,6,7-tetranor-4-oxa-18,19-tetradehydro-4,8-inter-m-phenylene PGI$_2$ methyl ester or 15-epi-11-dehydroxy-11-(p-phenylbenzoyloxy)-16-methyl-2,5,6,7-tetranor-4-oxa-18,19-tetradehydro-4,8-inter-m-phenylene PGI$_2$ methyl ester is employed in place of 15-epi-11-dehydroxy-11-(p-toluoyloxy)-16-methyl-5,6,7-trino-18,19-tetradehydro-4,8-inter-m-phenylene PGI$_2$ methyl ester yields 16-methyl-2,5,6,7-tetranor-4-oxa-18,19-tetradehydro-4,8-inter-m-phenylene PGI$_2$. The same procedure as in Example 57 except that 15-epi-11-dehydroxy-11-(p-toluoyloxy)-16-methyl-2,5,6,7-tetranor-18,19-tetradehydro-4,8-inter-m-phenylene PGI$_2$ methyl ester, 15-epi-11-dehydroxy-11-acetoxy-16-methyl-2,5,6,7-tetranor-18,19-tetradehydro-4,8-inter-m-phenylene PGI$_2$ methyl ester, 15-epi-11-dehydroxy-11-propionyloxy-16-methyl-2,5,6,7-tetranor-18,19-tetradehydro-4,8-inter-m-phenylene PGI$_2$ methyl ester, 15-epi-11-dehydroxy-11-butyroyloxy-16-methyl-2,5,6,7-tetranor-18,19-tetradehydro-4,8-inter-m-phenylene PGI$_2$ methyl ester, 15-epi-11-dehydroxy-11-octanoyloxy-16-methyl-2,5,6,7-tetranor-18,19-tetradehydro-4,8-inter-m-phenylene PGI$_2$ methyl ester, 15-epi-11-dehydroxy-11-decanoyloxy-16-methyl-2,5,6,7-tetranor-18,19-tetradehydro-4,8-inter-m-phenylene PGI$_2$ methyl ester, 15-epi-11-dehydroxy-11-valeroyloxy-16-methyl-2,5,6,7-tetranor-18,19-tetradehydro-4,8-inter-m-phenylene PGI$_2$ methyl ester, 15-epi-11-dehydroxy-11-benzoyloxy-16-methyl-2,5,6,7-tetranor-18,19-tetradehydro-4,8-inter-m-phenylene PGI$_2$ methyl ester, 15-epi-11-dehydroxy-11-($\alpha$-naphthoyloxy)-16-methyl-2,5,6,7-tetranor-18,19-tetradehydro-4,8-inter-m-phenylene PGI$_2$ methyl ester, 15-epi-11-dehydroxy-11($\beta$-naphthoyloxy)-16-methyl-2,5,6,7-tetranor-18,19-tetradehydro-4,8-inter-m-phenylene PGI$_2$ methyl ester, 15-epi-11-dehydroxy-11-(m-toluoyloxy)-16-methyl-2,5,6,7-tetranor-18,19-tetradehydro-4,8-inter-m-phenylene PGI$_2$ methyl ester, 15-epi-11-dehydroxy-11-(o-toluoyloxy)-16-methyl-2,5,6,7-tetranor-18,19-tetradehydro-4,8-inter-m-phenylene PGI$_2$ methyl ester or 15-epi-11-dehydroxy-11-(p-phenylbenzoyloxy)-16-methyl-2,5,6,7-tetranor-18,19-tetradehydro-4,8-inter-m-phenylene PGI$_2$ methyl ester is employed in place of 15-epi-11-dehydroxy-11-(p-toluoyloxy)-16-methyl-5,6,7-trinor-18,19-tetradehydro-4,8-inter-m-phenylene PGI$_2$ methyl ester yields 16-methyl-2,5,6,7-tetranor-18,19-tetradehydro-4,8-inter-m-phenylene PGI$_2$.

EXAMPLE 58

16-methyl-20-homo-5,6,7-trinor-18,19-tetradehydro-4,8-inter-m-phenylene PGI₂ methyl ester (9)

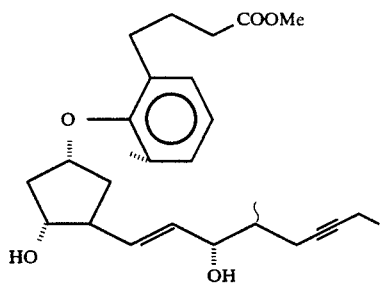

The same procedure as in Example 51 was repeated except that 186 mg of 15-epi-11-dehydroxy-11-(p-toluoyloxy)-16-methyl-20-homo-5,6,7-trinor-18,19-tetradehydro-4,8-inter-m-phenylene PGI₂ methyl ester as a substrate to obtain 98 mg of the captioned compound.

IR (neat) ν: 3370, 1740, 1595, 970 cm⁻¹
Mass (m/e) 426 (M+)

The same procedure as in Example 58 except that 15-epi-11-dehydroxy-11-acetoxy-16-methyl-20-homo-5,6,7-trinor-18,19-tetradehydro-4,8-inter-m-phenyl PGI₂ methyl ester, 15-epi-11-dehydroxy-11-propionyloxy-16-methyl-20-homo-5,6,7-trinor-18,19-tetradehydro-4,8-inter-m-phenylene PGI₂ methyl ester, 15-epi-11-dehydroxy-11-butyroyloxy-16-methyl-20-homo-5,6,7-trinor-18,19-tetradehydro-4,8-inter-m-phenylene PGI₂ methyl ester, 15-epi-11-dehydroxy-11-octanoyloxy-16-methyl-20-homo-5,6,7-trinor-18,19-tetradehydro-4,8-inter-m-phenylene PGI₂ methyl ester, 15-epi-11-dehydroxy-11-decanoyloxy-16-methyl-20-homo-5,6,7-trinor-18,19-tetradehydro-4,8-inter-m-phenylene PGI₂ methyl ester, 15-epi-11-dehydroxy-11-valeroyloxy-16-methyl-20-homo-5,6,7-trinor-18,19-tetradehydro-4,8-inter-m-phenylene PGI₂ methyl ester, 15-epi-11-dehydroxy-11-benzoyloxy-16-methyl-20-homo-5,6,7-trinor-18,19-tetradehydro-4,8-inter-m-phenylene PGI₂ methyl ester, 15-epi-11-dehydroxy-11-(α-naphthoyloxy)-16-methyl-20-homo-5,6,7-trinor-18,19-tetradehydro-4,8-inter-m-phenylene PGI₂ methyl ester, 15-epi-11-dehydroxy-11-(β-naphthoyloxy)-16-methyl-20-homo-5,6,7-trinor-18,19-tetradehydro-4,8-inter-m-phenylene PGI₂ methyl ester, 15-epi-11-dehydroxy-11-(m-toluoyloxy)-16-methyl-20-homo-5,6,7-trinor-18,19-tetradehydro-4,8-inter-m-phenylene PGI₂ methyl ester, 15-epi-11-dehydroxy-11-(o-toluoyloxy)-16-methyl-20-homo-5,6,7-trinor-18,19-tetradehydro-4,8-inter-m-phenylene PGI₂ methyl ester or 15-epi-11-dehydroxy-11-(p-phenylbenzoyloxy)-16-methyl-20-homo-5,6,7-trinor-18,19-tetradehydro-4,8-inter-m-phenylene PGI₂ methyl ester is employed in place of 15-epi-11-dehydroxy-11-(p-toluoyloxy)-16-methyl-20-homo-5,6,7-trinor-18,19-tetradehydro-4,8-inter-m-phenylene PGI₂ methyl ester yields the captioned compound.

The same procedure as in Example 58 except that 15-epi-11-dehydroxy-11-acetoxy-16-methyl-20-homo-5,6,7-trinor-18,19-tetradehydro-4,8-inter-m-phenylene PGI₂ ethyl ester, 15-epi-11-dehydroxy-11-propionyloxy-16-methyl-20-homo-5,6,7-trinor-18,19-tetradehydro-4,8-inter-m-phenylene PGI₂ ethyl ester, 15-epi-11-dehydroxy-11-butyroyloxy-16-methyl-20-homo-5,6,7-trinor-18,19-tetradehydro-4,8-inter-m-phenylene PGI₂ ethyl ester, 15-epi-11-dehydroxy-11-octanoyloxy-16-methyl-20-homo-5,6,7-trinor-18,19-tetradehydro-4,8-inter-m-phenylene PGI₂ ethyl ester, 15-epi-11-dehydroxy-11-decanoyloxy-16-methyl-20-homo-5,6,7-trinor-18,19-tetradehydro-4,8-inter-m-phenylene PGI₂ ethyl ester, 15-epi-11-dehydroxy-11-valeroyloxy-16-methyl-20-homo-5,6,7-trinor-18,19-tetradehydro-4,8-inter-m-phenylene PGI₂ ethyl ester, 15-epi-11-dehydroxy-11-benzoyloxy-16-methyl-20-homo-5,6,7-trinor-18,19-tetradehydro-4,8-inter-m-phenylene PGI₂ ethyl ester, 15-epi-11-dehydroxy-11-(α-naphthoyloxy)-16-methyl-20-homo-5,6,7-trinor-18,19-tetradehydro-4,8-inter-m-phenylene PGI₂ ethyl ester, 15-epi-11-dehydroxy-11-(β-naphthoyloxy)-16-methyl-20-homo-5,6,7-trinor-18,19-tetradehydro-4,8-inter-m-phenylene PGI₂ ethyl ester, 15-epi-11-dehydroxy-11-(m-toluoyloxy)-16-methyl-20-homo-5,6,7-trinor-18,19-tetradehydro-4,8-inter-m-phenylene PGI₂ ethyl ester, 15-epi-11-dehydroxy-11-(o-toluoyloxy)-16-methyl-20-homo-5,6,7-trinor-18,19-tetradehydro-4,8-inter-m-phenylene PGI₂ ethyl ester or 15-epi-11-dehydroxy-11-(p-phenylbenzoyloxy)-16-methyl-20-homo-5,6,7-trinor-18,19-tetradehydro-4,8-inter-m-phenylene PGI₂ ethyl ester is employed in place of 15-epi-11-dehydroxy-11-(p-toluoyloxy)-16-methyl-20-homo-5,6,7-trinor-18,19-tetradehydro-4,8-inter-m-phenylene PGI₂ methyl ester yields 16-methyl-20-homo-5,6,7-trinor-18,19-tetradehydro-4,8-inter-m-phenylene PGI₂ ethyl ester.

INDUSTRIAL APPLICABILITY

By the present invention, a novel manufacturing process of m-phenylene type PGI₂ derivatives having excellent stereoselectivity and regiospecificity was provided. The method of the present invention decreases the number of steps in which a reaction at low temperature or column chromatography is required, and excells in ease of operation and reproducibility. Thus, by the process of the present invention, PGI₂ derivatives which are useful as an anti-thrombus agent, antiulcer drug, antiatherosclerotic drug and the like may be produced industrially in large scale.

We claim:

1. A process of preparing 5,6,7-trinor-4,8-inter-m-phenylene PGI₂ derivatives of the formula (VII)

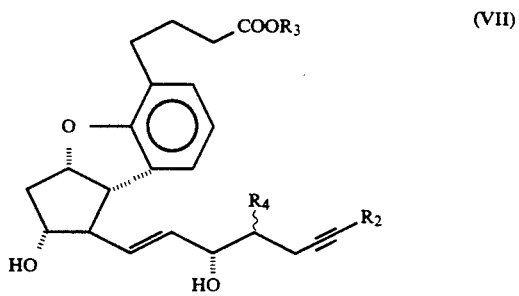

(wherein $R_2$ represents methyl or ethyl;
$R_3$ and $R_4$ represent hydrogen or methyl) comprising the steps of:
reacting 3,5-cis-dibromocyclopentene of the formula

with potassium salt of an o-halophenol to form 3,5-cis-bis(2-halophenoxy)cyclopentene of the formula 6

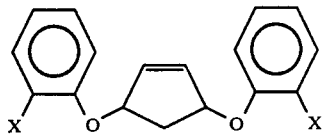

(wherein X represents chlorine, bromine or iodine); treating said compound of the formula 6 with magnesium metal to convert to a Grignard reagent; cyclizing said Grignard reagent in the presence of a metal catalyst to form a cyclopentabenzofuran of the formula 7;

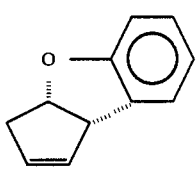

brominating said compound of the formula 7 to form a tetrabromide of the formula 8;

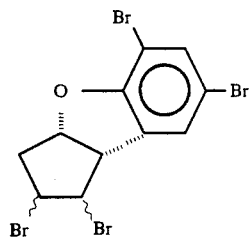

reductively removing the bromine of the 5-membered ring moiety of said compound of the formula 8 to form 3a,8b-cis-dihydro-3H-5,7-dibromocyclopenta[b]benzofuran of the formula 1

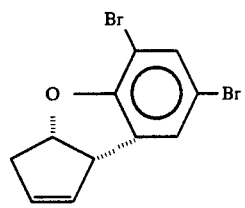

converting said compound by Prins reaction and hydrolysis to a diol of the formula 2;

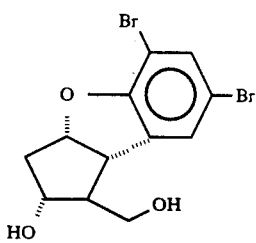

reacting said compound of the formula 2 with a Grignard reagent so as to carry out metal-halogen exchange;

reacting the resulting product with methyl 3-formyl propionate;

subjecting the resulting product to hydrogenolysis to give a diol ester of the formula 3;

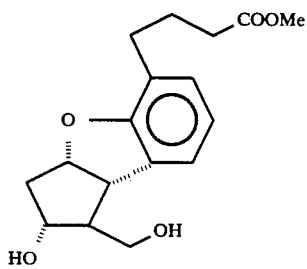

subjecting said compound of the formula 3 to protection of the primary hydroxyl group, esterification of the secondary hydroxyl group and removal of the protective group of primary hydroxyl group so as to convert said compound of the formula 3 to a compound of the formula (I);

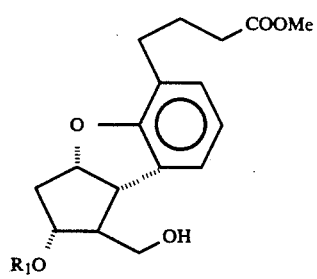

(wherein $R_1$ represents acetyl, p-toluoyl, o-toluoyl, benzoyl m-toluoyl, p-t-butylbenzoyl, p-phenylbenzoyl, 3,5-dinitrobenzoyl, N-phenylcarbamoyl, α-naphthoyl, β-naphtholyl or p-nitrobenzoyl);

converting said compound of the formula (I) to a compound of the formula (III)

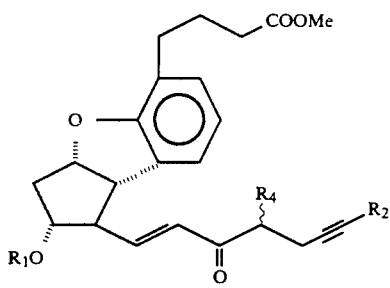
(III)

(wherein $R_1$, $R_2$ and $R_3$ represent the same meanings as mentioned above) by oxidizing said compound of the formula (I) and reacting the resulting product with a compound of the formula (II) in the presence of a strong base;

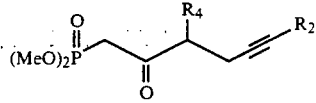
(II)

(wherein $R_2$ and $R_4$ represent the same meanings as mentioned above)

reducing said compound of the formula (III) with a reducing agent to form a compound of the formula (IV);

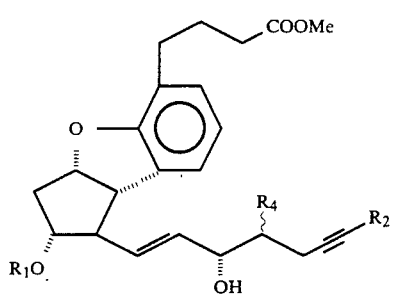
(IV)

(wherein $R_1$, $R_2$ and $R_4$ represent the same meanings as mentioned above) and solvolyzing or hydrolyzing said compound of the formula (IV) to form said compound of the formula (VII).

2. A process for preparing 3a,8b-cis-dihydro-3H-cyclopenta[b]benzofuran of the formula 7:

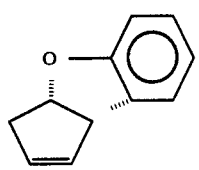
7 comprising the steps of:
converting a 3,5-cis-bis(2-halophenoxy)cyclopentene derivative of the formula 6:

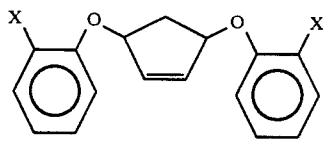
6

(wherein X represents Cl, Br or I) to a Grignard reagent using magnesium metal; and cyclizing the resulting product in the presence of a metal catalyst.

3. A process for preparing 3a,8b-cis-dihydro-3H-5,7-dibromocyclopenta[b]benzofuran of the formula 1

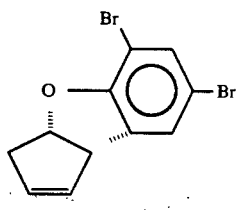
1 characterized by comprising the step of reductively debrominating a tetrabromocyclopenta[b]benzofuran derivative of the formula 8:

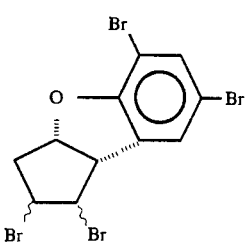
8 with sodium thiosulfate, sodium sulfide or zinc.

4. A tetrabromocyclopenta[b]benzofuran derivative of the formula 8

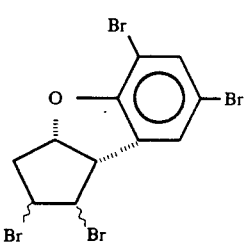
8

5. A process for preparing the tetrabromocyclopenta[b]benzofuran derivative of claim 4, characterized by comprising the step of brominating 3a,8b-cis-dihydro-3H-cyclopenta[b]benzofuran of the formula 7:

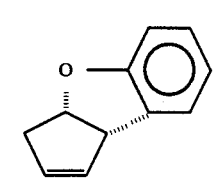
7

6. A process for preparing a compound of the formula (I):

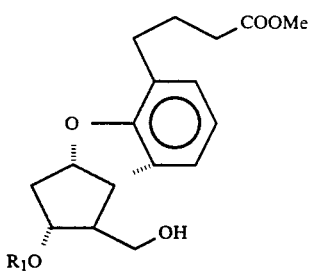

(I)

(wherein $R_1$ represents the same meaning as mentioned above) characterized by comprising the steps of:

forming 3,5-cis-bis(2-halophenoxy)cyclopentene of the formula 6:

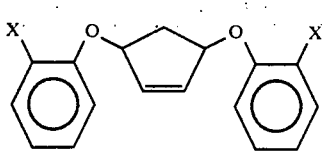

6

(wherein X represents chlorine, bromine or iodine) by reacting 3,5-cis-dibromocyclopentene of the formula 5:

5 with potassium salt of o-halophenol;

converting said compound of the formula 6 with magnesium metal to a Grignard reagent;

cyclizing the resulting product in the presence of a metal catalyst to form cyclopentabenzofuran of the formula 7;

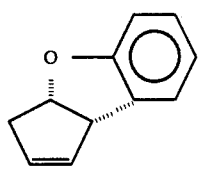

7 brominating said compound of the formula 7 to form a tetrabromide of the formula 8;

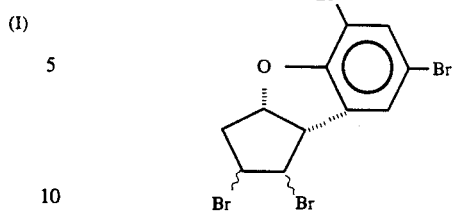

8 reductively removing the bromines on the 5-membered ring moiety of said compound of the formula 8 to form 3,a,8b-cis-dihydro-3H,5,7-dibromocyclopenta[b]benzofuran of the formula 1;

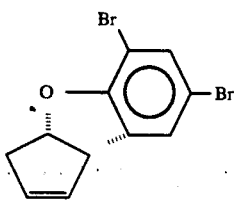

1 subjecting said compound of the formula 1 to Prins reaction and hydrolysis to convert the same to a diol of the formula 2;

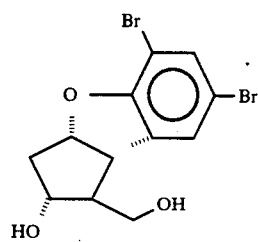

2 treating said compound of the formula 2 with a Grignard reagent so as to carry out metal-halogen exchange;

reacting the resulting product with methyl 3-formyl propionate;

subjecting the resulting product to hydrogenolysis to give a diol ester of the formula 3;

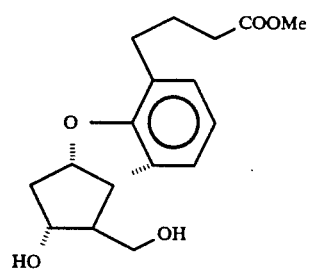

3 and subjecting said compound of the formula 3 to protection of the primary hydroxyl group, esterification of the secondary hydroxyl group and deprotection of the primary hydroxyl group so as to convert said compound of the formula 3 to said compound of the formula [I].

* * * * *

UNITED STATES PATENT AND TRADEMARK OFFICE
CERTIFICATE OF CORRECTION

PATENT NO. : 5,202,447                     Page 1 of 6
DATED     : April 13, 1993
INVENTOR(S) : Kiyotaka Ohno et al It is certified that error appears in the above-identified patent and that said Letters Patent is hereby corrected as shown below:

In Column 3, under the heading "CHART 2", starting at about line 33, please change

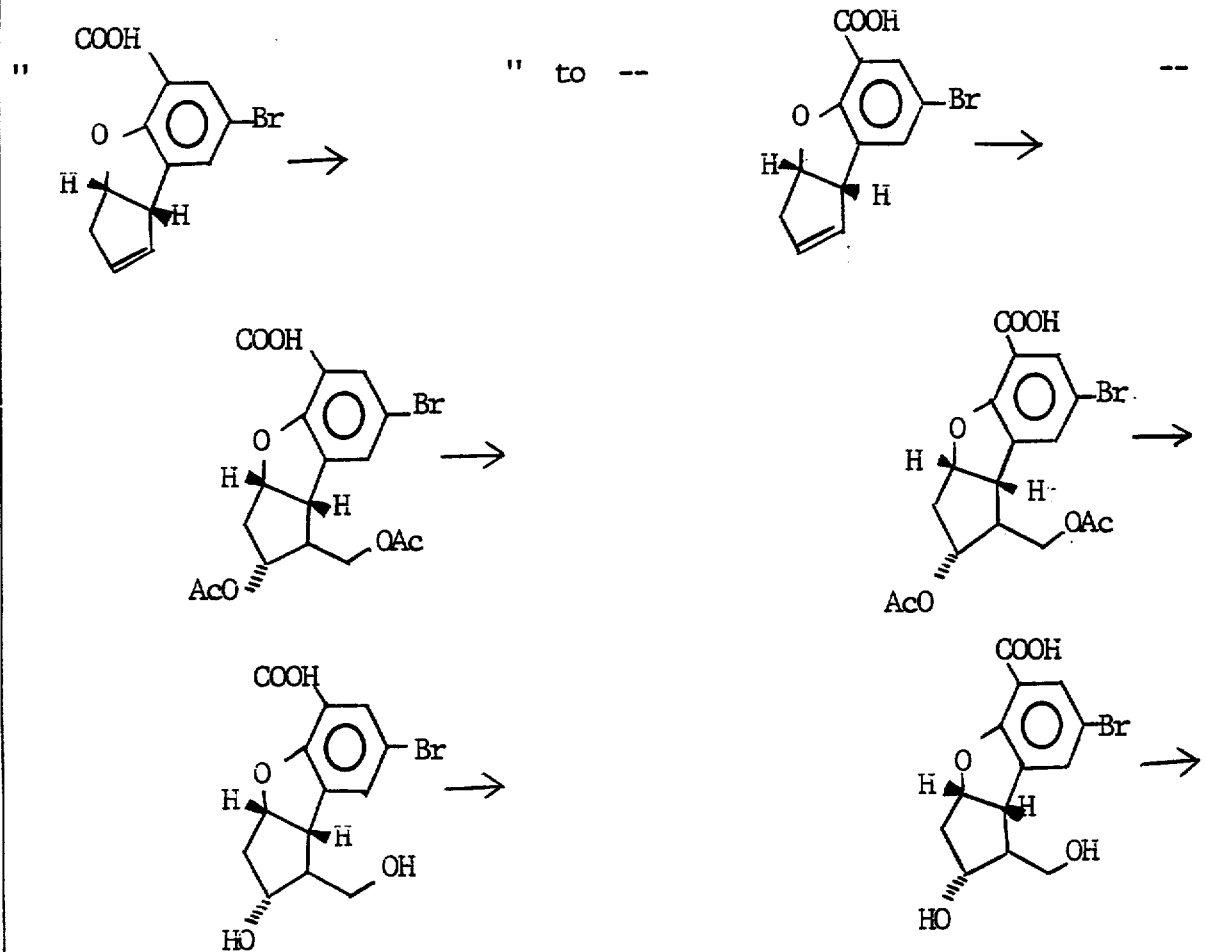

UNITED STATES PATENT AND TRADEMARK OFFICE
CERTIFICATE OF CORRECTION

PATENT NO. : 5,202,447

DATED : April 13, 1993

INVENTOR(S) : Kiyotaka Ohno et al

It is certified that error appears in the above-identified patent and that said Letters Patent is hereby corrected as shown below:

In Column 4, under the heading "CHART 2", starting at about line 5, please change

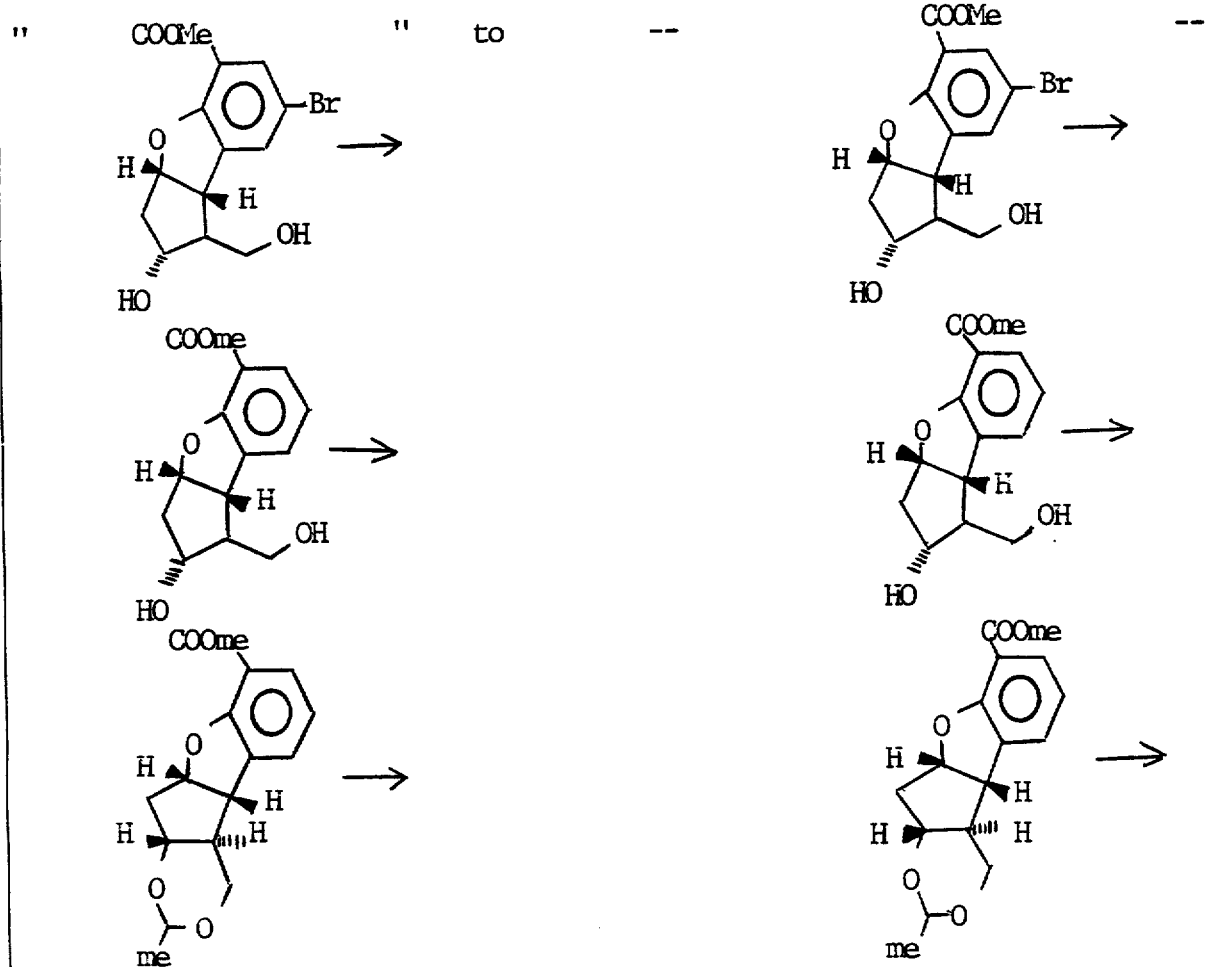

UNITED STATES PATENT AND TRADEMARK OFFICE
CERTIFICATE OF CORRECTION

PATENT NO. : 5,202,447

DATED : April 13, 1993

INVENTOR(S) : Kiyotaka Ohno et al

It is certified that error appears in the above-identified patent and that said Letters Patent is hereby corrected as shown below:

In Column 4, starting at about line 40, please change

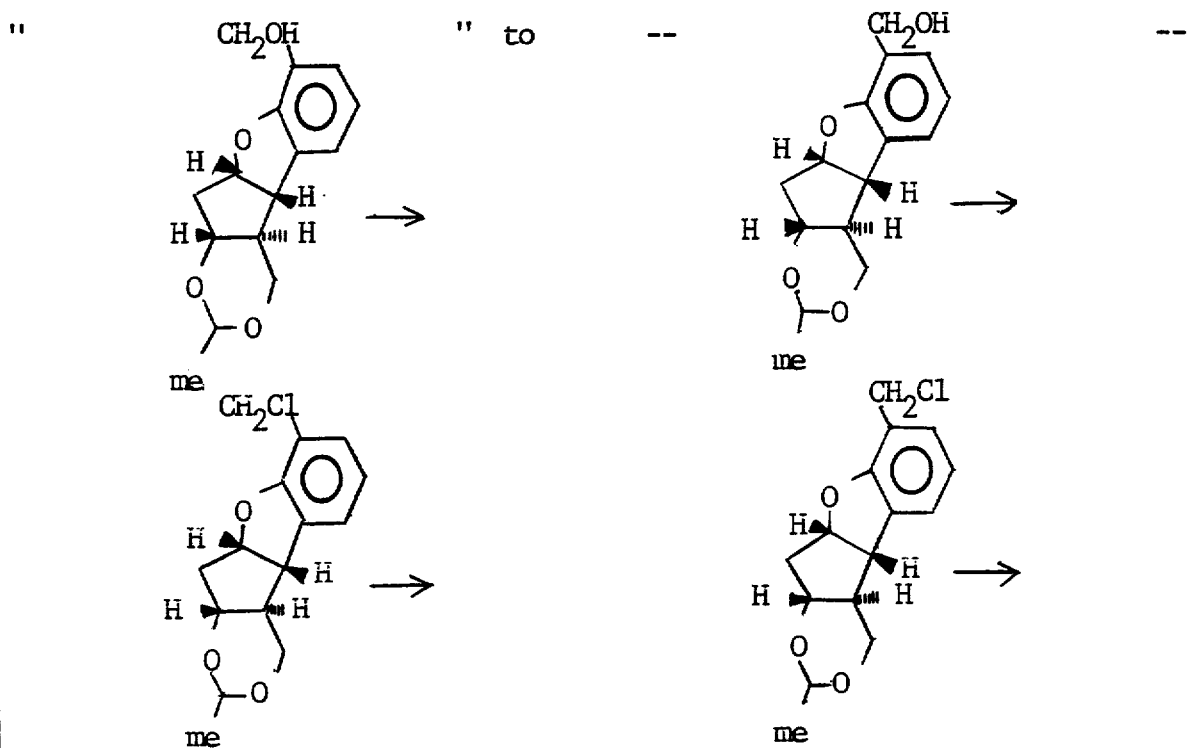

UNITED STATES PATENT AND TRADEMARK OFFICE
CERTIFICATE OF CORRECTION

PATENT NO. : 5,202,447
DATED : April 13, 1993
INVENTOR(S) : Kiyotaka Ohno et al

It is certified that error appears in the above-identified patent and that said Letters Patent is hereby corrected as shown below:

In Column 34, line 16, please change
"4-[2-endo-o-toloyloxy-1-exo-hydroxymethyl-3a,8b-cis-" to
--4-[2-endo-p-toloyloxy-1-exo-hydroxymethyl-3a,8b-cis---.

In Column 43, line 65, please change "wa" to --was--.

In Column 51, line 64, please change "silyloxy-5,6,7-trino-b" to --silyloxy-5,6,7-trinor--.

In Column 57, line 27, please change "1 9-2.5" to --1.9-2.5--.

In Column 58, beginning at about line 47, please change

"  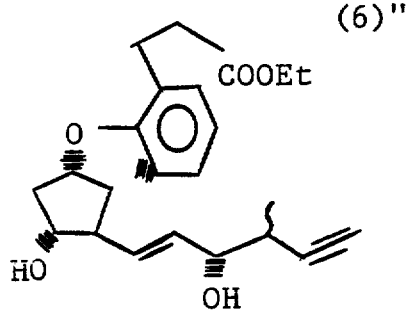  (6)"   to   --  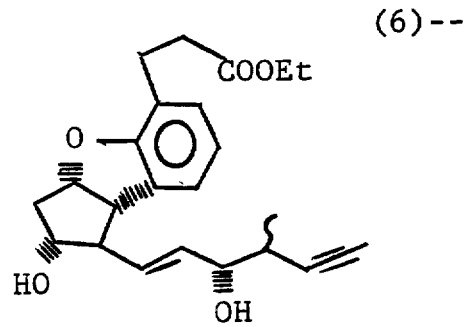  (6)--

UNITED STATES PATENT AND TRADEMARK OFFICE
CERTIFICATE OF CORRECTION

PATENT NO. : 5,202,447
DATED : April 13, 1993
INVENTOR(S) : Kiyotaka Ohno et al

It is certified that error appears in the above-identified patent and that said Letters Patent is hereby corrected as shown below:

In Column 60, starting at about line 7, please change

" 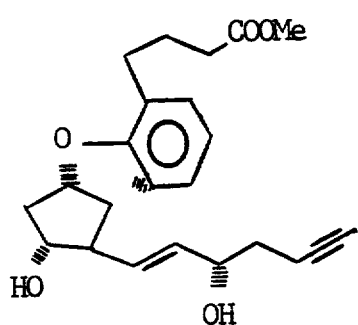 (7)" to -- 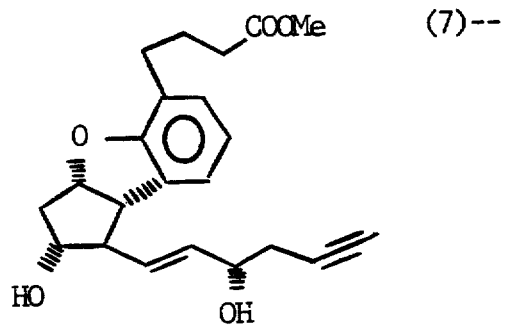 (7)--

In Column 63, starting at about line 33, please change

" 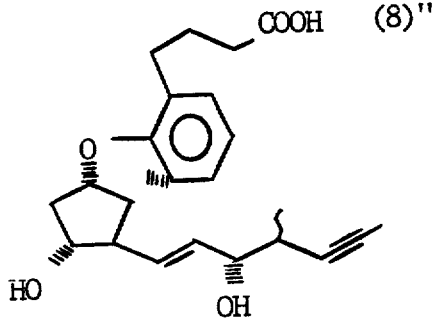 (8)" to -- 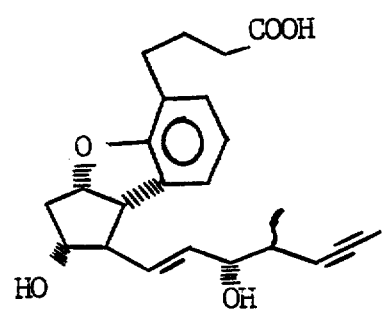 (8)--

UNITED STATES PATENT AND TRADEMARK OFFICE
CERTIFICATE OF CORRECTION

PATENT NO. : 5,202,447
DATED : April 13, 1993
INVENTOR(S) : Kiyotaka Ohno et al

It is certified that error appears in the above-identified patent and that said Letters Patent is hereby corrected as shown below:

In Column 69, starting at about line 6, please change

" 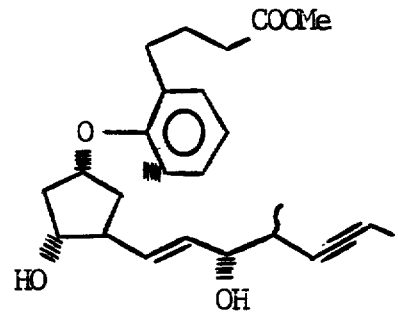 (9)" to -- 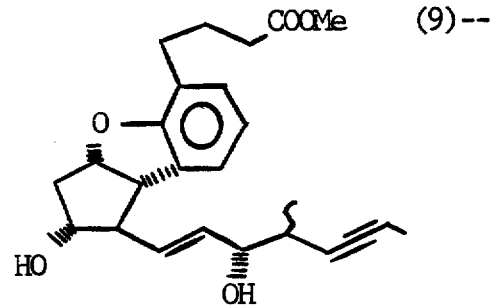 (9)--

Signed and Sealed this

Fourth Day of October, 1994

Attest:

BRUCE LEHMAN

Attesting Officer

Commissioner of Patents and Trademarks